US010918106B2

(12) United States Patent
Bayer et al.

(10) Patent No.: US 10,918,106 B2
(45) Date of Patent: Feb. 16, 2021

(54) METHODS FOR HYDRAULIC ENHANCEMENT OF CROPS

(71) Applicant: Sound Agriculture Company, Emeryville, CA (US)

(72) Inventors: Travis Scott Bayer, San Francisco, CA (US); Eric Alan Davidson, San Francisco, CA (US); Yonek Hleba, San Francisco, CA (US)

(73) Assignee: Sound Agriculture Company, Emeryville, CA (US)

( * ) Notice: Subject to any disclaimer, the term of this patent is extended or adjusted under 35 U.S.C. 154(b) by 0 days.

(21) Appl. No.: 15/568,716

(22) PCT Filed: Apr. 23, 2016

(86) PCT No.: PCT/US2016/029080
§ 371 (c)(1),
(2) Date: Oct. 23, 2017

(87) PCT Pub. No.: WO2016/172655
PCT Pub. Date: Oct. 27, 2016

(65) Prior Publication Data
US 2018/0310557 A1 Nov. 1, 2018

Related U.S. Application Data

(60) Provisional application No. 62/152,100, filed on Apr. 24, 2015, provisional application No. 62/152,555, filed on Apr. 24, 2015.

(51) Int. Cl.
| | | |
|---|---|---|
| *A01N 43/16* | (2006.01) | |
| *A01N 43/40* | (2006.01) | |
| *C07D 407/12* | (2006.01) | |
| *C07D 307/60* | (2006.01) | |
| *C07D 307/77* | (2006.01) | |
| *C07D 307/56* | (2006.01) | |
| *A01N 43/08* | (2006.01) | |
| *C07D 401/12* | (2006.01) | |
| *A01N 43/36* | (2006.01) | |

(52) U.S. Cl.
CPC ............ *A01N 43/16* (2013.01); *A01N 43/08* (2013.01); *A01N 43/36* (2013.01); *A01N 43/40* (2013.01); *C07D 307/56* (2013.01); *C07D 307/60* (2013.01); *C07D 307/77* (2013.01); *C07D 401/12* (2013.01); *C07D 407/12* (2013.01)

(58) Field of Classification Search
CPC ........ A01N 43/16; A01N 43/40; A01N 43/18; C07D 405/12; C07D 407/12; C07D 409/12
See application file for complete search history.

(56) References Cited

U.S. PATENT DOCUMENTS

| | | | |
|---|---|---|---|
| 3,954,806 A | * | 5/1976 | Sih ..................... C07D 307/93 549/299 |
| 7,038,064 B2 | | 5/2006 | Ishii et al. |
| 7,825,268 B2 | | 11/2010 | Stumpe et al. |
| 8,101,171 B2 | | 1/2012 | Becard et al. |
| 8,946,280 B2 | | 2/2015 | Lachia et al. |
| 9,131,685 B2 | | 9/2015 | Dahman et al. |
| 9,994,557 B2 | | 6/2018 | Davidson et al. |
| 2008/0318773 A1 | | 12/2008 | Becard et al. |
| 2010/0137373 A1 | * | 6/2010 | Hungenberg .......... A01N 43/08 514/341 |
| 2011/0207608 A1 | | 8/2011 | Zhu et al. |
| 2011/0230352 A1 | | 9/2011 | Rameau et al. |
| 2012/0046169 A1 | | 2/2012 | Dahman et al. |
| 2014/0287924 A1 | * | 9/2014 | Al-Babili ............. C07D 307/58 504/299 |
| 2015/0274690 A1 | | 10/2015 | Davidson et al. |

FOREIGN PATENT DOCUMENTS

| | | |
|---|---|---|
| CN | 1141952 A | 2/1997 |
| CN | 103068241 A | 4/2013 |
| CN | 103396390 A | 11/2013 |
| WO | WO-9831837 A1 | 7/1998 |
| WO | WO-2010125065 A2 | 11/2010 |
| WO | WO-2012057404 A1 | 5/2012 |
| WO | WO-2013092430 A1 | 6/2013 |
| WO | WO-2015061764 A1 | 4/2015 |
| WO | WO-2016172655 A1 | 10/2016 |

OTHER PUBLICATIONS

Siame, BA, et al., "Isolation of Strigol, a germination stimulant for Striga asiatica, from host plants" J Agricultural and Food Chemistry 41 (9): 1486-1491 (1993) (Year: 1993).*
Pepperman et al., "Strigol analogs as germination regulators in weed and crop seeds", Weed Science 36: 719-725 (1988) (Year: 1988).*
Mwakaboko et al., "Single step synthesis of strigolactone analogues from cyclic keto enols, germination stimulants for seeds of parasitic weeds", Bioorg Med Chem 19: 5006-5011 (2011) (Year: 2011).*
Agusti et al., "Strigolactone signaling is required for auxin-dependent stimulation of secondary growth in plants", Proc Natl Acad Sci USA 108: 20242-20247 (2011) (Year: 2011).*
Mwakaboko, et al. Single step synthesis of strigolactone analogues from cyclic keto enols, germination stimulants for seeds of parasitic weeds. Bioorg Med Chem. Aug. 15, 2011;19(16):5006-11.
Akiyama, et al. Strigolactones: chemical signals for fungal symbionts and parasitic weeds in plant roots. Ann Bot. Jun. 2006;97(6):925-31. Epub Mar. 30, 2006.

(Continued)

*Primary Examiner* — John Pak
(74) *Attorney, Agent, or Firm* — Wilson Sonsini Goodrich & Rosati

(57) ABSTRACT

Disclosed herein are compounds, salts, solvates of Formula (1), and any formulation thereof. Also disclosed are methods of eliciting hydraulic enhancement and/or increasing yield of a plant by contacting a plant with compounds, salts, solvates of Formula (1), or any formulation thereof.

31 Claims, 17 Drawing Sheets

(56) References Cited

OTHER PUBLICATIONS

Alder, et al. The path from β-carotene to carlactone, a strigolactone-like plant hormone. Science. Mar. 16, 2012;335(6074):1348-51. doi: 10.1126/science.1218094.
Besserer, et al. GR24, a synthetic analog of strigolactones, stimulates the mitosis and growth of the arbuscular mycorrhizal fungus *Gigaspora rosea* by boosting its energy metabolism. Plant Physiol. Sep. 2008;148(1):402-13. doi: 10.1104/pp.108.121400. Epub Jul. 9, 2008.
Bouwmeester, et al. Secondary metabolite signalling in host-parasitic plant interactions. Curr Opin Plant Biol. Aug. 2003;6(4):358-64.
Boyer, et al. Grain yields with limited water. J Exp Bot. Nov. 2004;55(407):2385-94. Epub Jul. 30, 2004.
Boyer, et al. New Strigolactone Analogs as Plant Hormones with Low Activities in the Rhizosphere. Molecular Plant Advance Access, published Dec. 26, 2013.
Boyer, et al. Structure-activity relationship studies of strigolactone-related molecules for branching inhibition in garden pea: molecule design for shoot branching. Plant Physiol. Aug. 2012;159(4):1524-44. doi: 10.1104/pp.112.195826. Epub Jun. 21, 2012.
Bruce, et al. Molecular and physiological approaches to maize improvement for drought tolerance. J Exp Bot. Jan. 2002;53(366):13-25.
CAS Registry No. 1401956-60-2, STN Entry Date Oct. 24, 2012.
Chadwick, et al. Sesquiterpenoids lactones: benefits to plants and people. Int J Mol Sci. Jun. 19, 2013;14(6):12780-805. doi: 10.3390/ijms140612780.
Chugh, et al. Differential antioxidative response of tolerant and sensitive maize (*Zea mays* L.) genotypes to drought stress at reproductive stage. Indian J Biochem Biophys. Apr. 2013;50(2):150-8.
Clark, et al. Agronomic, economic, and environmental comparison of pest management in conventional and alternative tomato and corn systems in northern California. Agriculture, Ecosystems & Environment. vol. 68, Issues 1-2, Mar. 1998, pp. 51-71.
Climate Stabilization Targets: Emissions, Concentrations, and Impacts over Decades to Millenina. 2011: The National Academies Press.
Cohen, et al. Structure-function relations of strigolactone analogs: activity as plant hormones and plant interactions. Mol Plant. Jan. 2013;6(1):141-52. doi: 10.1093/mp/sss134. Epub Dec. 8, 2012.
Eddy, et al. Optimizing Greenhouse Corn Prduction: Summary. Purdue Methods for Corn Growth, 2012.
Eddy, et al. Optimizing Greenhouse Corn Production: Materials and Methods. Purdue Methods for Corn Growth, 2010.
Eddy, et al. Optimizing Greenhouse corn Production: What is the Best Lighting and Plant Density? Purdue Methods for Corn Growth, 2010.
European search report and search opinion dated Jun. 8, 2017 for EP Application No. 14855263.1.
Gambrel, et al. Optimizing Greenhouse Corn Production: What Is the Best Pot Size? Purdue Methods for Corn Growth, 2010.
Gambrel, et al. Optimizing Greenhouse Corn Production: What Is the Best Root Medium? Purdue Methods for Corn Growth, 2010.
Goulet, et al. Climbing the branches of the strigolactones pathway one discovery at a time. Plant Physiol. Oct. 2010;154(2):493-6. doi: 10.1104/pp.110.161026.
Harrigan, et al. The forage and grain of MON 87460, a drought-tolerant corn hybrid, are compositionally equivalent to that of conventional corn. J Agric Food Chem. Oct. 28, 2009;57(20):9754-63. doi: 10.1021/jf9021515.
Harris, et al. Water-stress-induced changes in the abscisic acid content of guard cells and other cells of *Vicia faba* L. leaves as determined by enzyme-amplified immunoassay. Proc Natl Acad Sci USA. Apr. 1988;85(8):2584-8.
International search report and written opinion dated Jan. 16, 2015 for PCT Application No. US2014/062297.
Kim, et al. Guard cell signal transduction network: advances in understanding abscisic acid, CO2, and Ca2+ signaling. Annu Rev Plant Biol. 2010;61:561-91. doi: 10.1146/annurev-arplant-042809-112226.
Reilly, et al. Regulation of Biochemical Plant Growth Regulators at the U.S. Environmental Protection Agency. HortTechnology Jan.-Mar. 2002, vol. 12, No. 1, pp. 55-58.
Lawrence, B. Production of clary sage oil and sclareol in North America. In Proceedings of the 4th international symposium on medicinal and aromatic plants. 1994.
Leonberger, et al. Optimizing Greenhouse Corn Production: What Is the Best Open Pollination Method? Purdue Methods for Corn Growth, 2010.
Lopez-Raez, et al. Does abscisic acid affect strigolactone biosynthesis? New Phytol. Jul. 2010;187(2):343-54. doi: 10.1111/j.1469-8137.2010.03291.x. Epub May 10, 2010.
Lopez-Raez, et al. Strigolactones: ecological significance and use as a target for parasitic plant control. Pest Manag Sci. May 2009;65(5):471-7. doi: 10.1002/ps.1692.
Macias, et al. New Chemical Clues for Broomrape-Sunflower Host-Parasite Interactions: Synthesis of Guaianestrigolactones. Journal of agricultural and food chemistry 57.13 (2009): 5853-5864.
Magnus, et al. Tentative Molecular Mechanism for Germination Stimulation of Striga and Orobanche Seeds by Strigol and Its Synthetic Analogues. J. Agric. Food. Chem. 1992, 40 1066-1070.
Malik, et al. Aromatic A-ring analogues of orbanchol, new germinati on stimulants for seeds of parasitic weeds. Organic & Biomolecular Chemistry. Apr. 7, 2011. 9(7), pp. 2286-2293.
Mwakaboko, A. S. Synthesis and Biological Evaluation of new Strigolactone Analogues as Germination Stimulants for the Seeds of the Parasitic Weeds *Striga* and *Orobanche* spp. Thesis. Catholic University Nijmegen, Netherlands. Mar. 25, 2003.
Mwakaboko, et al. Strigolactone analogs derived from ketones using a working model for germination stimulants as a blueprint. Plant Cell Physiol. Apr. 2011;52(4):699-715. doi: 10.1093/pcp/per031. Epub Mar. 18, 2011.
Nielsen, R. Corn growth and development, what goes on from planting to harvest? Extension University, 1997.
O'Connor, C. Soil Matters: How the Federal Crop Insurance Program should be reformed to encourage low-risk farming methods with high-reward environmental outcomes. 2013.
Office action dated Apr. 17, 2017 for U.S. Appl. No. 14/856,908.
Office action dated Oct. 21, 2016 for U.S. Appl. No. 14/856,908.
Office action dated Dec. 14, 2017 for U.S. Appl. No. 14/856,908.
Okamoto, et al. Activation of dimeric ABA receptors elicits guard cell closure, ABA-regulated gene expression, and drought tolerance. Proc Natl Acad Sci U S A. Jul. 16, 2013;110(29):12132-7. doi: 10.1073/pnas.1305919110. Epub Jul. 1, 2013.
Peleg, et al. Hormone balance and abiotic stress tolerance in crop plants. Curr Opin Plant Biol. Jun. 2011;14(3):290-5. doi: 10.1016/j.pbi.2011.02.001. Epub Mar. 4, 2011.
Peppi, et al. Abscisic Acid Application Timing and Concentration Affect Firmness, Pigmentation, and Color of 'Flame Seedless' Grapes. HortScience Oct. 2006, vol. 41, No. 6, 1440-1445.
Pimentel, et al. Environmental and Economic Costs of Pesticide Use. BioScience, vol. 42, No. 10, 1992.
Prasch, et al. Simultaneous application of heat, drought, and virus to *Arabidopsis* plants reveals significant shifts in signaling networks. Plant Physiol. Aug. 2013;162(4):1849-66. doi: 10.1104/pp.113.221044. Epub Jun. 10, 2013.
Qin, et al. Sesquiterpene lactones from Inula hupehensis inhibit nitric oxide production in RAW264.7 macrophages. Planta Med. Jun. 2012;78(10):1002-9. doi: 10.1055/s-0031-1298621. Epub May 30, 2012.
Raupp, et al. New sesquiterpene lactones from sunflower root exudate as germination stimulants for Orobanche cumana. J Agric Food Chem. Nov. 6, 2013;61(44):10481-7. doi: 10.1021/jf402392e. Epub Oct. 24, 2013.
Ren, et al. Cytotoxic and NF-κB inhibitory sesquiterpene lactones from Piptocoma rufescens. Tetrahedron. Mar. 25, 2012;68(12):2671-2678. Epub Jan. 26, 2012.
Rink, et al. Optimizing Greenouse Corn Production: What is the Best Irrigation Strategy? Purdue Methods for Corn Growth, 2010.
Rivero, et al. Enhanced cytokinin synthesis in tobacco plants expressing PSARK::IPT prevents the degradation of photosynthetic

(56) References Cited

OTHER PUBLICATIONS protein complexes during drought. Plant Cell Physiol. Nov. 2010;51(11):1929-41. doi: 10.1093/pcp/pcq143. Epub Sep. 24, 2010.
Rungeler, et al. Germacranolides from Mikania guaco. Phytochemistry. Mar. 2001;56(5):475-89.
Ruyter-Spira, et al. Physiological effects of the synthetic strigolactone analog GR24 on root system architecture in *Arabidopsis*: another belowground role for strigolactones? Plant Physiol. Feb. 2011;155(2):721-34. doi: 10.1104/pp.110.166645. Epub Nov. 30, 2010.
Schoper, et al. Plant factors controlling seed set in maize : the influence of silk, pollen, and ear-leaf water status and tassel heat treatment at pollination. Plant Physiol. Jan. 1987;83(1):121-5.
Shin, et al. Sesquiterpenes and other constituents from *Dendranthema zawadskii* var. latilobum. Chem Pharm Bull (Tokyo). 2012;60(3):306-14.
CAS Registry No. 920959-02-0, STN Entry Date Feb. 14, 2007.
Stephanopoulous, G. Synthetic biology and metabolic engineering. ACS Synth Biol. Nov. 16, 2012;1(11):514-25. doi: 10.1021/sb300094q.
Tanaka, et al. Synthesis of 7-oxo-5-deoxystrigol, a 7-oxygenated strigolactone analog. Biosci Biotechnol Biochem. 2013;77(4):832-5. Epub Apr. 7, 2013.
Tarklason, et al. Effect of Nitrogen Application Timing on Corn Production Using Subsurface Drip Irrigation. Soil Science, Mar. 2009, vol. 174, Issue 3, pp. 174-179.
Tollefson, J. Drought-tolerant maize gets US debut. Nature. Jan. 13, 2011;469(7329):144. doi: 10.1038/469144a.
Tsuchiya, et al. Strigolactones: a new hormone with a past. Curr Opin Plant Biol. Oct. 2009;12(5):556-61. doi: 10.1016/j.pbi.2009.07.018. Epub Aug. 31, 2009.
United States Department of Agriculture, National Agricultural Statistics Service Crop production report released Sep. 2013.
United States Department of Agriculture, Risk Management Agency RMA Indemnities (As of Jul. 8, 2013). Accessed Sep. 26, 2013 from: http://www.rma.usda.gov/data/indemnity/2013/070813table.pdf.
Upar, et al. Efficient enantioselective synthesis of (+)-sclareolide and (+)-tetrahydroactinidiolide: chiral LBA-induced biomimetic cyclization. Tetrahedron: Asymmetry vol. 20, Issue 14, Jul. 29, 2009, pp. 1637-1640.
U.S. Appl. No. 14/856,908 Notice of Allowance dated Mar. 29, 2018.
Wigchert, et al. Dose-response of seeds of the parasitic weeds *Striga* and *Orobanche* toward the synthetic germination stimulants GR 24 and Nijmegen 1. J Agric Food Chem. Apr. 1999;47(4):1705-10.
Witt, et al. Metabolic and phenotypic responses of greenhouse-grown maize hybrids to experimentally controlled drought stress. Mol Plant. Mar. 2012;5(2):401-17. doi: 10.1093/mp/ssr102. Epub Dec. 15, 2011.
Xie, et al. Fabacyl acetate, a germination stimulant for root parasitic plants from Pisum sativum. Phytochemistry 70.2 (2009): 211-215.
Yoneyama, et al. Characterization of strigolactones exuded by *Asteraceae* plants. Plant growth regulation 65.3 (2011): 495-504.
Yoneyma, et al. Strigolactones as a new plant growth regulator. Presentation at the MARCO Symposium 2009, Tsukuba, Japan, on Oct. 6, 2009.
Yoshida, et al. Plants that attack plants: molecular elucidation of plant parasitism. Curr Opin Plant Biol. Dec. 2012;15(6):708-13. doi: 10.1016/j.pbi.2012.07.004. Epub Aug. 13, 2012.
Zwanenburg, et al. Structure and Activity of Strigolactones: New Plant Hormones with a Rich Future. Mol. Plant, vol. 6, Issue 1, pp. 38-62.
Zwanenburg, et al. Structure and function of natural and synthetic signalling molecules in parasitic weed germination. Pest Manag Sci 2009; 65: 478-491.
Co-pending U.S. Appl. No. 15/947,508, filed Apr. 6, 2018.
International Search Report and Written Opinion dated Sep. 14, 2016 for International Application No. PCT/US2016/029080.
Pubchem, Substance Record for SID 54096325 Create Date: Oct. 8, 2008 [retrieved on Aug. 16, 2016]. Retrieved from the Internet: https://pubchem.ncbi.nlm.nih.gov/substance/54096325.
Pubchem, Substance Record for SID 55052802 Create Date: Oct. 8, 2008 [retrieved on Jun. 1, 2016]. Retrieved from the Internet: https://pubchem.ncbi.nlm.nih.gov/substance/55052802.
Toh, et al. Thermoinhibition uncovers a role for strigolactones in *Arabidopsis* seed germination. Plant Cell Physiol. Jan. 2012;53(1):107-17.
Alinanuswe S. Mwakaboko, Binne Zwanenburg, "Single step synthesis of strigolactone analogues from cyclic keto enols. germination stimulants for seeds of parasitic weeds", Bioorganic & Medicinal Chemistry, vol. 19 (16), 2011, pp. 5006-5011.
Bupe A. Siame et al., "Isolation of strigol, a germination stimulant for Striga asiatica, from host plants", Journal Agricultural and Food Chemistry 41(9),1993, pp. 1486-1491.
Agusti, Javier et al. "Strigolactone signaling is required for auxin-dependent stimulation of secondary growth in plants." Proceedings of the National Academy of Sciences of the United States of America vol. 108,50 (2011): 20242-7. doi:10.1073/pnas.1111902108.
Pepperman, Armand B. et al., "Strigol analogs as germination regulators in weed and crop sedes", 1988, Weed Science 36:719-725.

\* cited by examiner

METHODS FOR HYDRAULIC ENHANCEMENT OF CROPS

CROSS-REFERENCE

This application is a U.S. National Stage Entry of PCT/US2016/029080, filed Apr. 23, 2016, which claims the benefit of U.S. Provisional Application No. 62/152,100, filed Apr. 24, 2015, and U.S. Provisional Application No. 62/152,555, filed Apr. 24, 2015, each of which is incorporated herein by reference in its entirety.

SUMMARY OF THE INVENTION

Disclosed herein is a compound of Formula (1):

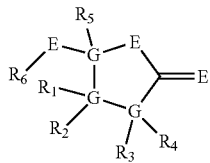

Formula (1)

or any salt or solvate thereof,
wherein:
each E is independently O, S, or —$NR_7$;
each G is independently C or N;
$R_1$, $R_4$, $R_5$, and $R_6$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —$OR_8$, —$C(O)R_8$,

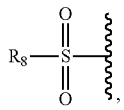

or a lone electron pair, wherein

indicates a single bond;
$R_2$ and $R_3$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, or a lone electron pair; or $R_2$ and $R_3$ together form a bond, or form a substituted or unsubstituted aryl; and
$R_7$ and $R_8$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl.

In some embodiments, $R_2$ and $R_3$ together form a bond. In some embodiments, the compound, salt, or solvate has a structure of Formula (2):

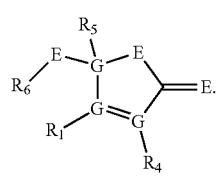

Formula (2)

In some embodiments, $R_4$ is alkyl. In some embodiments, $R_4$ is methyl. In some embodiments, each G is independently C. In some embodiments, each G is independently N. In some embodiments, each E is independently O. In some embodiments, each E is independently S. In some embodiments, each E is independently —$NR_7$. In some embodiments, $R_1$ and $R_5$ is each independently H.

In some embodiments, the compound, salt, or solvate has a structure of Formula (3):

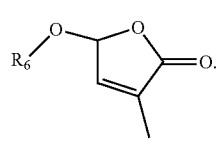

Formula (3)

In some embodiments, $R_6$ has a structure of Formula (4):

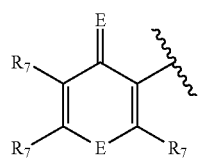

Formula (4)

wherein

indicates a single bond.

In some embodiments, each E of the compound, salt, or solvate is independently O, S, or —$NR_7$. In some embodiments, each E is independently O. In some embodiments, each $R_7$ is independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl. In some embodiments, each $R_7$ is independently H or substituted or unsubstituted alkyl. In some embodiments, each $R_7$ is independently H.

In some embodiments, the compound, salt, or solvate has a structure of Formula (5):

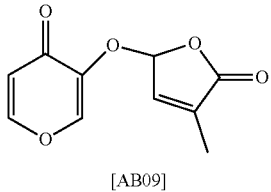

Formula (5)

[AB09]

In some embodiments, $R_6$ has a structure of Formula (6):

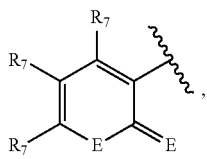

Formula (6)

wherein

indicates a single bond.

In some embodiments, $R_6$ has a structure selected from the group consisting of,

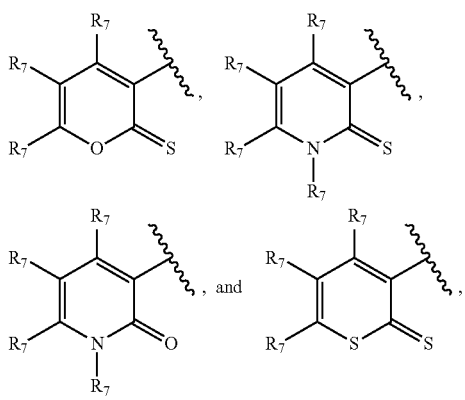

wherein

indicates a single bond.

In some embodiments, the compound, salt, or solvate has a structure selected from the group consisting of Formula (7), (8), (9), and (10):

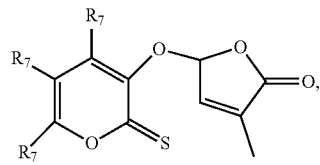

Formula (7)

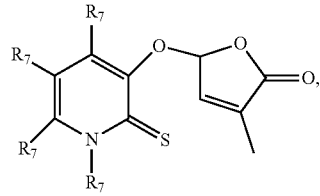

Formula (8)

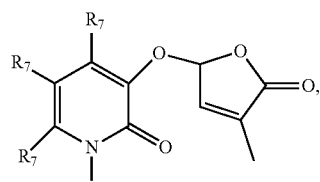

Formula (9)

and

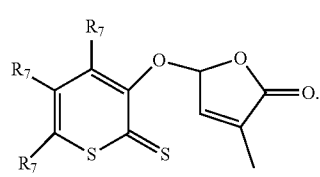

Formula (10)

In some embodiments, $R_6$ has a structure of Formula (11):

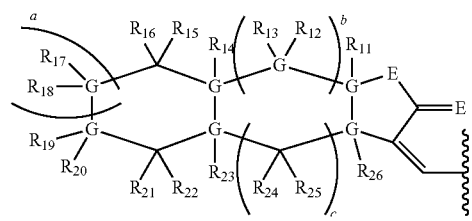

Formula (11)

wherein:

indicates a single bond;

a, b, c are each independently 0, 1, or 2;

$R_{15}$, $R_{16}$, $R_{21}$, $R_{22}$, $R_{24}$, and $R_{25}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —$OR_8$, —$C(O)R_8$, or

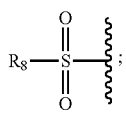

$R_{12}$, $R_{13}$, $R_{17}$, $R_{18}$, $R_{19}$, and $R_{20}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —$OR_8$, —$C(O)R_8$,

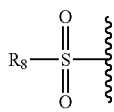

or a lone electron pair;

$R_{11}$ and $R_{26}$ are each independently H, alkyl, haloalkyl, amino, halo, lone electron pair, or —$OR_8$; or $R_{11}$ and $R_{26}$ together form a bond;

$R_{14}$ and $R_{23}$ are each independently H, alkyl, haloalkyl, amino, halo, lone electron pair, or —$OR_8$; or $R_{14}$ and $R_{23}$ together form a bond; and $R_8$ is each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl.

In some embodiments, the compound, salt, or solvate has a structure of Formula (12):

Formula (12)

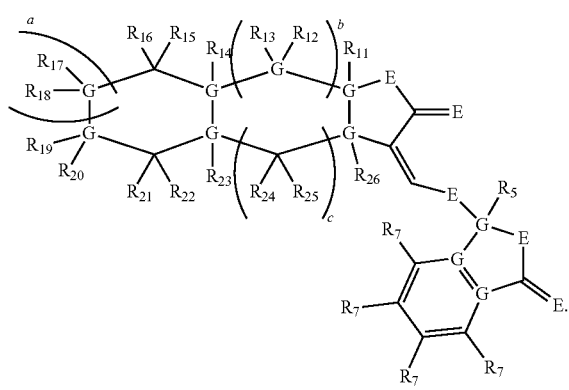

In some embodiments, a, b, c are each independently 0, 1, or 2. The compound, salt, or solvate may be a compound, salt, or solvate, wherein a is 0, b is 0, and c is 0. The compound, salt, or solvate may be a compound, salt, or solvate, wherein a is 0, b is 0, and c is 1. The compound, salt, or solvate may be a compound, salt, or solvate, wherein a is 0, b is 0, and c is 2. The compound, salt, or solvate may be a compound, salt, or solvate, wherein a is 0, b is 1, and c is 0. The compound, salt, or solvate may be a compound, salt, or solvate, wherein a is 0, b is 1, and c is 1. The compound, salt, or solvate may be a compound, salt, or solvate, wherein a is 0, b is 1, and c is 2. The compound, salt, or solvate may be a compound, salt, or solvate, wherein a is 0, b is 2, and c is 0. The compound, salt, or solvate may be a compound, salt, or solvate, wherein a is 0, b is 2, and c is 1. The compound, salt, or solvate may be a compound, salt, or solvate, wherein a is 0, b is 2, and c is 2. The compound, salt, or solvate may be a compound, salt, or solvate, wherein a is 1, b is 0, and c is 0. The compound, salt, or solvate may be a compound, salt, or solvate, wherein a is 1, b is 0, and c is 1. The compound, salt, or solvate may be a compound, salt, or solvate, wherein a is 1, b is 0, and c is 2. The compound, salt, or solvate may be a compound, salt, or solvate, wherein a is 1, b is 1, and c is 0. The compound, salt, or solvate may be a compound, salt, or solvate, wherein a is 1, b is 1, and c is 1. The compound, salt, or solvate may be a compound, salt, or solvate, wherein a is 1, b is 1, and c is 2. The compound, salt, or solvate may be a compound, salt, or solvate, wherein a is 1, b is 2, and c is 0. The compound, salt, or solvate may be a compound, salt, or solvate, wherein a is 1, b is 2, and c is 1. The compound, salt, or solvate may be a compound, salt, or solvate, wherein a is 1, b is 2, and c is 2. The compound, salt, or solvate may be a compound, salt, or solvate, wherein a is 2, b is 0, and c is 0. The compound, salt, or solvate may be a compound, salt, or solvate, wherein a is 2, b is 0, and c is 1. The compound, salt, or solvate may be a compound, salt, or solvate, wherein a is 2, b is 0, and c is 2. The compound, salt, or solvate may be a compound, salt, or solvate, wherein a is 2, b is 1, and c is 0. The compound, salt, or solvate may be a compound, salt, or solvate, wherein a is 2, b is 1, and c is 1. The compound, salt, or solvate may be a compound, salt, or solvate, wherein a is 2, b is 1, and c is 2. The compound, salt, or solvate may be a compound, salt, or solvate, wherein a is 2, b is 2, and c is 0. The compound, salt, or solvate may be a compound, salt, or solvate, wherein a is 2, b is 2, and c is 1. The compound, salt, or solvate may be a compound, salt, or solvate, wherein a is 2, b is 2, and c is 2. In one example, the compound, salt, or solvate is a compound, salt, or solvate, wherein a is 1, b is 2, and c is 0.

In some embodiments, $R_6$ has a structure of Formula (13) or (14):

Formula (13)

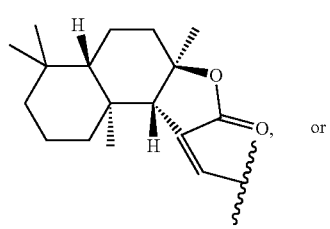

or

Formula (14)

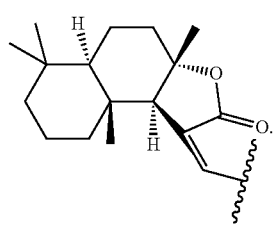

In some embodiments, the compound, salt, or solvate has a structure of Formula (15) or (16):

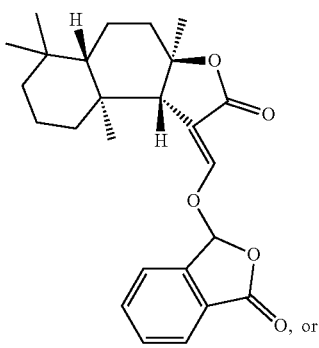

Formula (15)

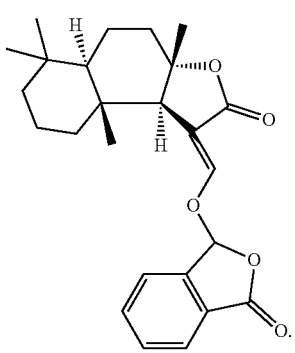

Formula (16)

In some embodiments, the compound, salt, or solvate is AB10, which has a structure of Formula (15) or (16).

In some embodiments, the compound, salt, or solvate is an isomer of the compound, salt, or solvate. In some embodiments, the compound, salt, or solvate is a stereoisomer of the compound, salt, or solvate.

In some embodiments, the compound, salt, or solvate is a diastereoisomer. In some embodiments, the compound, salt, or solvate is a diastereoisomer having a diastereomeric excess of at least about 50%, 60%, 70%, 80%, 85%, 90%, 95%, or from at least about 50% to 100%. The compound, salt, or solvate disclosed herein, may have a diastereomeric excess of at least about 15%, 20%, 30%, 40%, 50%, 60%, 70%, 80%, 85%, 90%, 95%, or 99%. The compound, salt, or solvate disclosed herein, may have a diastereomeric excess of about 15%-99%, 20%-99%, 30%-99%, 40%-99%, 50%-99%, 60%-99%, 70%-99%, 80%-99%, 90%-99%, 15%-90%, 20%-90%, 30%-90%, 40%-90%, 50%-90%, 60%-90%, 70%-90%, 80%-90%, 15%-80%, 20%-80%, 30%-80%, 40%-80%, 50%-80%, 60%-80%, 70%-80%, 15%-70%, 20%-70%, 30%-70%, 40%-70%, 50%-70%, 60%-70%, 15%-60%, 20%-60%, 30%-60%, 40%-60%, 50%-60%, 15%-50%, 20%-50%, 30%-50%, 40%-50%, 15%-40%, 20%-40%, 30%-40%, 15%-30%, 20%-30%, or 15%-20%. In one embodiment, the compound, salt, or solvate disclosed herein, may have a diastereomeric excess of from at least about 50% to 100%.

In some embodiments, the compound, salt, or solvate is an enantiomer. In some embodiments, the compound, salt, or solvate is an enantiomer having an enantiomeric excess of at least about 50%, 60%, 70%, 80%, 85%, 90%, 95%, or from at least about 50% to 100%. The compound, salt, or solvate disclosed herein, may have an enantiomeric excess of at least about 15%, 20%, 30%, 40%, 50%, 60%, 70%, 80%, 85%, 90%, 95%, or 99%. The compound, salt, or solvate disclosed herein, may have an enantiomeric excess of about 15%-99%, 20%-99%, 30%-99%, 40%-99%, 50%-99%, 60%-99%, 70%-99%, 80%-99%, 90%-99%, 15%-90%, 20%-90%, 30%-90%, 40-90%, 50-90%, 60-90%, 70-90%, 80-90%, 15%-80%, 20%-80%, 30%-80%, 40%-80%, 50%-80%, 60%-80%, 70%-80%, 15%-70%, 20%-70%, 30%-70%, 40-70%, 50-70%, 60-70%, 15%-60%, 20%-60%, 30%-60%, 40%-60%, 50%-60%, 15%-50%, 20%-50%, 30%-50%, 40-50%, 15%-40%, 20%-40%, 30%-40%, 15%-30%, 20%-30%, or 15-20%. In one embodiment, the compound, salt, or solvate disclosed herein, may have an enantiomeric excess of from at least about 50% to 100%.

In some embodiments, the compound, salt, or solvate has a structure of Formula (17):

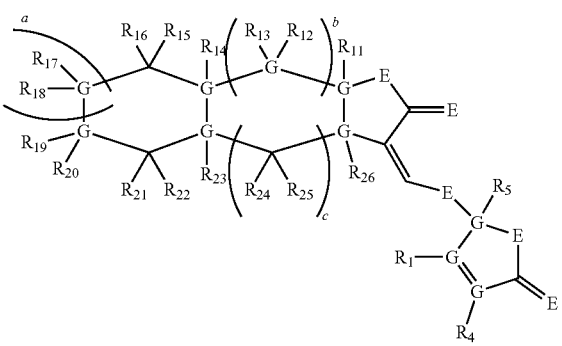

Formula (17)

wherein:

a, b, c are each independently 0, 1, or 2;

each E is independently O, S, or —$NR_7$;

each G is independently C or N;

$R_1$, $R_4$, $R_5$, $R_{15}$, $R_{16}$, $R_{21}$, $R_{22}$, $R_{24}$, and $R_{25}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —$OR_8$, —$C(O)R_8$, or

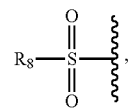

wherein

indicates a single bond;

$R_{12}$, $R_{13}$, $R_{17}$, $R_{18}$, $R_{19}$, and $R_{20}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —$OR_8$, —$C(O)R_8$,

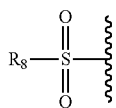

or a lone electron pair;

$R_{11}$ and $R_{26}$ are each independently H, alkyl, haloalkyl, amino, halo, lone electron pair, or —$OR_8$; or $R_{11}$ and $R_{26}$ together form a bond;

$R_{14}$ and $R_{23}$ are each independently H, alkyl, haloalkyl, amino, halo, lone electron pair, or —$OR_8$; or $R_{14}$ and $R_{23}$ together form a bond; and $R_7$ and $R_8$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl.

In some embodiments, a, b, c are each independently 0, 1, or 2. The compound, salt, or solvate may be a compound, salt, or solvate, wherein a is 0, b is 0, and c is 0. The compound, salt, or solvate may be a compound, salt, or solvate, wherein a is 0, b is 0, and c is 1. The compound, salt, or solvate may be a compound, salt, or solvate, wherein a is 0, b is 0, and c is 2. The compound, salt, or solvate may be a compound, salt, or solvate, wherein a is 0, b is 1, and c is 0. The compound, salt, or solvate may be a compound, salt, or solvate, wherein a is 0, b is 1, and c is 1. The compound, salt, or solvate may be a compound, salt, or solvate, wherein a is 0, b is 1, and c is 2. The compound, salt, or solvate may be a compound, salt, or solvate, wherein a is 0, b is 2, and c is 0. The compound, salt, or solvate may be a compound, salt, or solvate, wherein a is 0, b is 2, and c is 1. The compound, salt, or solvate may be a compound, salt, or solvate, wherein a is 0, b is 2, and c is 2. The compound, salt, or solvate may be a compound, salt, or solvate, wherein a is 1, b is 0, and c is 0. The compound, salt, or solvate may be a compound, salt, or solvate, wherein a is 1, b is 0, and c is 1. The compound, salt, or solvate may be a compound, salt, or solvate, wherein a is 1, b is 0, and c is 2. The compound, salt, or solvate may be a compound, salt, or solvate, wherein a is 1, b is 1, and c is 0. The compound, salt, or solvate may be a compound, salt, or solvate, wherein a is 1, b is 1, and c is 1. The compound, salt, or solvate may be a compound, salt, or solvate, wherein a is 1, b is 1, and c is 2. The compound, salt, or solvate may be a compound, salt, or solvate, wherein a is 1, b is 2, and c is 0. The compound, salt, or solvate may be a compound, salt, or solvate, wherein a is 1, b is 2, and c is 1. The compound, salt, or solvate may be a compound, salt, or solvate, wherein a is 1, b is 2, and c is 2. The compound, salt, or solvate may be a compound, salt, or solvate, wherein a is 2, b is 0, and c is 0. The compound, salt, or solvate may be a compound, salt, or solvate, wherein a is 2, b is 0, and c is 1. The compound, salt, or solvate may be a compound, salt, or solvate, wherein a is 2, b is 0, and c is 2. The compound, salt, or solvate may be a compound, salt, or solvate, wherein a is 2, b is 1, and c is 0. The compound, salt, or solvate may be a compound, salt, or solvate, wherein a is 2, b is 1, and c is 1. The compound, salt, or solvate may be a compound, salt, or solvate, wherein a is 2, b is 1, and c is 2. The compound, salt, or solvate may be a compound, salt, or solvate, wherein a is 2, b is 2, and c is 0. The compound, salt, or solvate may be a compound, salt, or solvate, wherein a is 2, b is 2, and c is 1. The compound, salt, or solvate may be a compound, salt, or solvate, wherein a is 2, b is 2, and c is 2. In one example, the compound, salt, or solvate is a compound, salt, or solvate, wherein a is 1, b is 2, and c is 0.

In some embodiments, the compound, salt, or solvate has a structure of Formula (18) or (19):

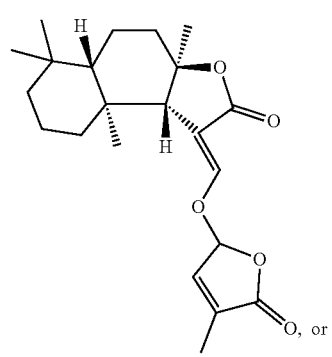

Formula (18)

Formula (19)

In some embodiments, the compound, salt, or solvate is AB01, which has a structure of Formula (18) or (19).

In some embodiments, $R_2$ and $R_3$ together form a substituted or unsubstituted aryl.

In some embodiments, the compound, salt, or solvate has a structure of Formula (20):

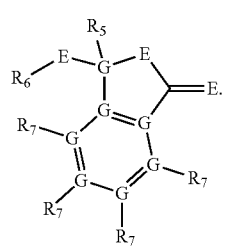

Formula (20)

In some embodiments, each $R_7$ is independently H. In some embodiments, each G is independently C. In some embodiments, each E is independently O. In some embodiments, $R_5$ is independently H.

In some embodiments, the compound, salt, or solvate has a structure of Formula (21):

Formula (21)

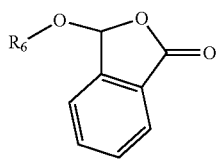

In some embodiments, $R_6$ has a structure selected from the group consisting of

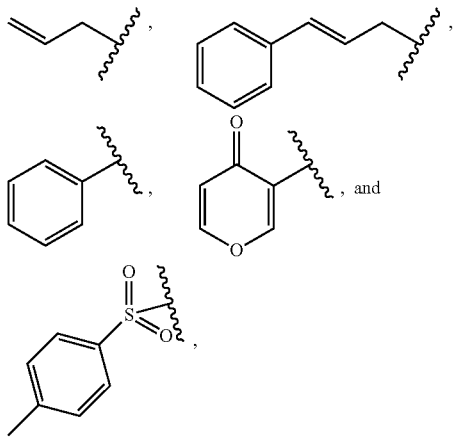

wherein

indicates a single bond.

In some embodiments, the compound, salt, or solvate has a structure selected from the group consisting of Formula (22), (23), (24), (25), and (26):

Formula (22)

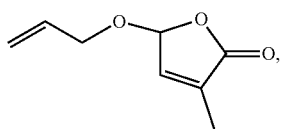

[AB06]

Formula (23)

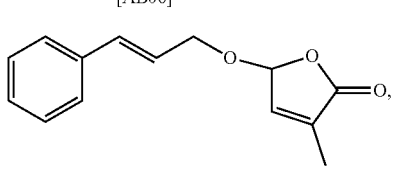

[AB07]

Formula (24)

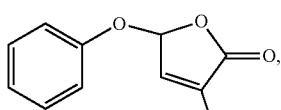

[AB08]

Formula (25)

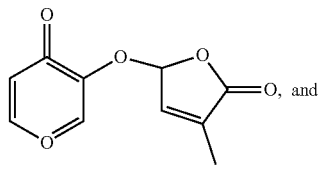

[AB09]

Formula (26)

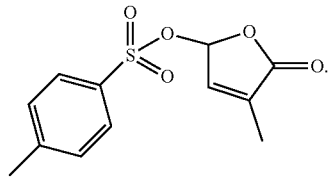

[AB12]

In some embodiments, the compound, salt, or solvate is an isomer of the compound, salt, or solvate. In some embodiments, the compound, salt, or solvate is a stereoisomer of the compound, salt, or solvate.

In some embodiments, the compound, salt, or solvate is a diastereoisomer. In some embodiments, the compound, salt, or solvate is a diastereoisomer having a diastereomeric excess of at least about 50%, 60%, 70%, 80%, 85%, 90%, 95%, or from at least about 50% to 100%. The compound, salt, or solvate disclosed herein, may have a diastereomeric excess of at least about 15%, 20%, 30%, 40%, 50%, 60%, 70%, 80%, 85%, 90%, 95%, or 99%. The compound, salt, or solvate disclosed herein, may have a diastereomeric excess of about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20%. In one embodiment, the compound, salt, or solvate disclosed herein, may have a diastereomeric excess of from at least about 50% to 100%.

In some embodiments, the compound, salt, or solvate is an enantiomer. In some embodiments, the compound, salt, or solvate is an enantiomer having an enantiomeric excess of at least about 50%, 60%, 70%, 80%, 85%, 90%, 95%, or from at least about 50% to 100%. The compound, salt, or solvate disclosed herein, may have an enantiomeric excess of at least about 15%, 20%, 30%, 40%, 50%, 60%, 70%, 80%, 85%, 90%, 95%, or 99%. The compound, salt, or solvate disclosed herein, may have an enantiomeric excess of about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20%. In one embodiment, the compound, salt, or solvate disclosed herein, may have an enantiomeric excess of from at least about 50% to 100%.

Also disclosed herein is a formulation comprising:
one or more compounds, salts, or solvates,
one or more strigolactones, or any salt or solvate thereof, one or more inhibitors of abscisic acid biosynthesis, or any salt or solvate thereof, one or more plant growth regulators, or any salt or solvate thereof, one or more excipients, or any combination thereof.

In some embodiments, the formulation comprises one or more compounds, salts, or solvates disclosed herein.

In some embodiments, the formulation comprises one or more compounds having a structure of Formula (17):

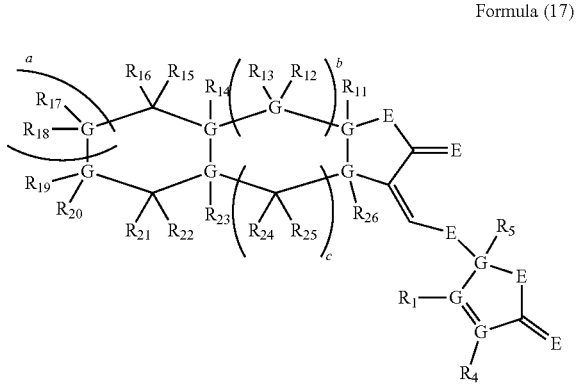

Formula (17)

wherein:

a, b, c are each independently 0, 1, or 2;

each E is independently O, S, or —$NR_7$;

each G is independently C or N;

$R_{15}$, $R_{16}$, $R_{21}$, $R_{22}$, $R_{24}$, and $R_{25}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —$OR_8$, —$C(O)R_8$, or

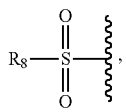

wherein

indicates a single bond;

$R_{12}$, $R_{13}$, $R_{17}$, $R_{18}$, $R_{19}$, and $R_{20}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —$OR_8$, —$C(O)R_8$,

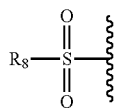

or a lone electron pair;

$R_{11}$ and $R_{26}$ are each independently H, alkyl, haloalkyl, amino, halo, lone electron pair, or —$OR_8$; or $R_{11}$ and $R_{26}$ together form a bond;

$R_{14}$ and $R_{23}$ are each independently H, alkyl, haloalkyl, amino, halo, lone electron pair, or —$OR_8$; or $R_{14}$ and $R_{23}$ together form a bond; and $R_8$ is each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl.

In some embodiments, the formulation comprises one or more compounds having a structure of Formula (18) or (19):

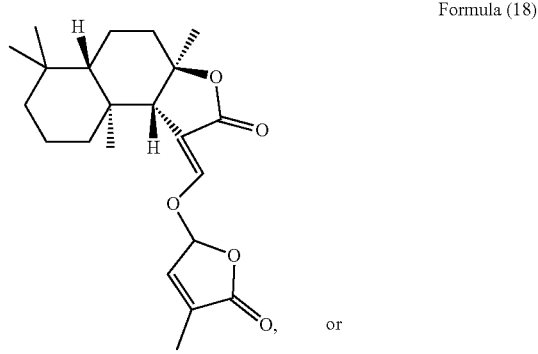

Formula (18)

or

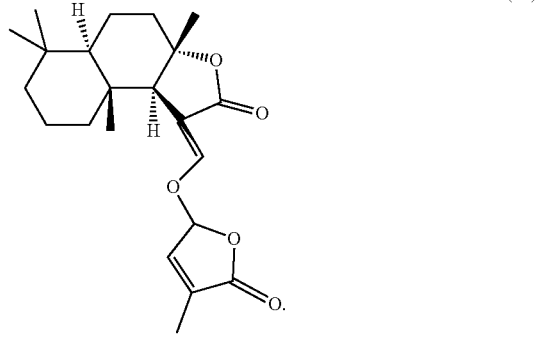

Formula (19)

In some embodiments, the formulation comprises one or more strigolactones, or any salt or solvate thereof. In some embodiments, the formulation comprises one or more strigolactones, or any salt or solvate thereof, wherein the one or more strigolactones comprise strigol, strigyl, strigyl acetate, orobanchol, orobanchyl acetate, 5-deoxystrigol, sorgolactone, 2'-epiorobanchol, sorgomol, solanacol, 7-oxoorobanchol, 7-oxoorobanchol acetate, fabacyl acetate, GR24; or any salt or solvate thereof.

In some embodiments, the formulation comprises one or more compounds, salts, or solvates disclosed herein and one or more strigolactones, or any salt or solvate thereof.

In some embodiments, the formulation comprises one or more inhibitors of abscisic acid biosynthesis, or any salt or solvate thereof. In some embodiments, the formulation comprises one or more inhibitors of abscisic acid biosynthesis, or any salt or solvate thereof, wherein the one or more inhibitors of abscisic acid biosynthesis comprise an inhibitor of phytoene destaturase, an inhibitor of 9-cis-epoxycarotenoid dioxygenase enzyme (NCED), an inhibitor of abscisic aldehyde oxidase (AAO); or any salt or solvate thereof. The one or more inhibitors of abscisic acid biosynthesis can comprise fluridone, nordihydroguaiaretic acid, abamine; or any salt or solvate thereof. The one or more inhibitors of abscisic acid biosynthesis can comprise one or more inhibitors of phytoene destaturase, or any salt or solvate thereof. The one or more inhibitors of phytoene destaturase can comprise fluridone, or any salt or solvate thereof.

In some embodiments, the formulation comprises one or more plant growth regulators, or any salt or solvate thereof. In some embodiments, the one or more plant growth regulators comprise one or more gibberellins, one or more cytokinins; or any salt or solvate thereof. In some embodiments, the one or more plant growth regulators comprise one or more gibberellins, or any salt or solvate thereof. In some embodiments, the one or more gibberellins comprise GA1, GA3, GA4, GA7, GA0, ent-gibberellane, ent-kaurene; or any salt or solvate thereof. In some embodiments, the one or more plant growth regulators comprise one or more cytokinins, or any salt or solvate thereof. In some embodiments, the one or more cytokinins comprise kinetin, zeatin, 6-benzylaminopurine, diphenylurea, thidiazuron; or any salt or solvate thereof. In some embodiments, the formulation comprises one or more gibberellins or any salt or solvate thereof and one or more cytokinins or any salt or solvate thereof. In some embodiments, the formulation comprises one or more gibberellins or any salt or solvate thereof and fluridone or any salt or solvate thereof. In some embodiments, the formulation comprises one or more cytokinins or any salt or solvate thereof and fluridone or any salt or solvate thereof. In some embodiments, the formulation comprises one or more gibberellins or any salt or solvate thereof, one or more cytokinins or any salt or solvate thereof, and fluridone or any salt or solvate thereof.

In some embodiments, the formulation comprises the excipient. In some embodiments, the excipient comprises water, a surfactant, an alcohol, or any combination thereof. In some embodiments, the surfactant comprises sulfosuccinate, naphthalene sulfonate, sulfated ester, phosphate ester, sulfated alcohol, alkyl benzene sulfonate, polycarboxylate, naphthalene sulfonate condensate, phenol sulfonic acid condensate, lignosulfonate, methyl oleyl taurate, polyvinyl alcohol, or any combination thereof. In some embodiments, the formulation comprises a fertilizer. In some embodiments, the fertilizer comprises nitrogen-containing fertilizer, phosphate-containing fertilizer, potassium-containing fertilizer, calcium-containing fertilizer, magnesium-containing fertilizer, sulfur-containing fertilizer, compound fertilizer, organic fertilizer, or any combination thereof. In some embodiments, the formulation comprises an insecticide, a fungicide, an herbicide, or any combination thereof. In some embodiments, the herbicide comprises a glyphosate. In some embodiments, the glyphosate comprises N-(phosphonomethyl)glycine.

In some embodiments, an amount of:
a compound, salt, or solvate,
a strigolactone, salt, or solvate thereof,
an inhibitor of abscisic acid biosynthesis, salt, or solvate thereof,
a plant growth regulator, salt, or solvate thereof, or
any combination thereof,
is respectively: each individually present, or is collectively present,
in an amount at least about 1 mg, 5 mg, 10 mg, 20 mg, 30 mg, 40 mg, 50 mg, 100 mg, 200 mg, 300 mg, 400 mg, 500 mg, 1 g, 5 g, 10 g, 50 g, 100 g, 500 g, 1 kg, 5 kg, 10 kg, 50 kg, 100 kg, or 1000 kg.

In some embodiments, an amount of:
a compound, salt, or solvate,
a strigolactone, salt, or solvate thereof,
an inhibitor of abscisic acid biosynthesis, salt, or solvate thereof,
a plant growth regulator, salt, or solvate thereof, or
any combination thereof,
is respectively: each individually present, or is collectively present,
in an amount from about 1 mg to about 1000 kg, for example, from about 1 mg to about 10 mg, from about 10 mg to about 50 mg, from about 50 mg to about 100 mg, from about 100 mg to about 500 mg, from about 500 mg to about 1 g, from about 1 g to about 10 g, from about 10 g to about 100 g, from about 100 g to about 500 g, from about 500 g to about 1 kg, from about 1 kg to about 10 kg, from about 10 kg to about 100 kg, from about 100 kg to about 500 kg, or from about 500 kg to about 1000 kg, or is collectively from about 1 mg to about 1000 kg, for example from about 1 mg to about 10 mg, from about 10 mg to about 50 mg, from about 50 mg to about 100 mg, from about 100 mg to about 500 mg, from about 500 mg to about 1 g, from about 1 g to about 10 g, from about 10 g to about 100 g, from about 100 g to about 500 g, from about 500 g to about 1 kg, from about 1 kg to about 10 kg, from about 10 kg to about 100 kg, from about 100 kg to about 500 kg, or from about 500 kg to about 1000 kg.

In some embodiments, an amount of:
a compound, salt, or solvate,
a strigolactone, salt, or solvate thereof,
an inhibitor of abscisic acid biosynthesis, salt, or solvate thereof,
a plant growth regulator, salt, or solvate thereof, or
any combination thereof,
is respectively: each individually present, or is collectively present,
in an amount about 1%, 5%, 10%, 20%, 30%, 40%, 50%, 60%, 70%, 80%, 90%, 95%, or 99% of the total weight of the formulation.

In some embodiments, an amount of:
a compound, salt, or solvate,
a strigolactone, salt, or solvate thereof,
an inhibitor of abscisic acid biosynthesis, salt, or solvate thereof,
a plant growth regulator, salt, or solvate thereof, or
any combination thereof,
is respectively: each individually present, or is collectively present,
in an amount about 1% to 100% of the total weight of the formulation, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the total weight of the formulation.

In some embodiments, the formulation is a powder formulation, a solid formulation, a gel, or a liquid formulation. In some embodiments, the formulation is a powder formulation. In some embodiments, the formulation is a solid formulation. In some embodiments, the formulation is a liquid formulation.

In another aspect, disclosed herein is a method comprising contacting a plant with the compound, salt, solvate, or formulation of any proceeding claim. Also disclosed herein is a method for eliciting hydraulic enhancement of a plant comprising contacting the plant with the compound, salt, solvate, or formulation, wherein a yield of the contacted plant is increased as compared to a substantially identical but otherwise uncontacted plant. Also disclosed herein is a method for increasing a yield of a plant comprising contacting the plant with the compound, salt, solvate, or formulation of any proceeding claim, wherein the yield of the contacted plant is increased as compared to a substantially identical but otherwise uncontacted plant. In some embodiments, the yield of the contacted plant is increased by at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to a substantially identical but otherwise uncontacted plant. In some embodiments, the yield of the contacted plant is increased by about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

Disclosed herein is a method for eliciting hydraulic enhancement of a plant comprising contacting the plant with the compound, salt, solvate, or formulation of any proceeding claim, wherein a transpiration of the contacted plant is increased as compared to a substantially identical but otherwise uncontacted plant. Disclosed herein is a method for increasing a transpiration of a plant comprising contacting the plant with the compound, salt, solvate, or formulation of any proceeding claim, wherein the transpiration of the contacted plant is increased as compared to a substantially identical but otherwise uncontacted plant.

In some embodiments, the transpiration of the plant is measured as peak stomatal conductance. In some embodiments, the transpiration of the plant is measured by using a leaf-porometer. In some embodiments, the transpiration of the contacted plant is increased by at least about 1%, 5%, 10%, 20%, 30%, 40%, 50%, 60%, 70%, 80%, 90%, 95%, or 99% as compared to a substantially identical but otherwise uncontacted plant. In some embodiments, the transpiration of the plant is measured as peak stomatal conductance. In some embodiments, the transpiration of the plant is measured by using a leaf-porometer. In some embodiments, the transpiration of the contacted plant is increased by about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

In some embodiments, the transpiration of the plant is measured as canopy temperature. In some embodiments, the transpiration of the plant is measured by using an infrared camera. In some embodiments, the canopy temperature of the contacted plant is decreased by at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, or 25° C. as compared to a substantially identical but otherwise uncontacted plant. In some embodiments, the transpiration of the plant is measured as canopy temperature. In some embodiments, the transpiration of the plant is measured by using an infrared camera. In some embodiments, the canopy temperature of the contacted plant is decreased by about 0.1 to about 1.0° C., about 1.0 to about 2.0° C., about 2.0 to about 5.0° C., or about 5.0 to about 10° C. as compared to a substantially identical but otherwise uncontacted plant.

In some embodiments, the transpiration of the plant is measured as transpired water volume. In some embodiments, the transpiration of the plant is measured by using an ex vivo hydraulic enhancement assay (xVHS). In some embodiments, the transpiration of the contacted plant is increased by at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, or 25 mL as compared to a substantially identical but otherwise uncontacted plant.

In some embodiments, the transpiration of the contacted plant is increased by at least about 0.1 to 0.2 mL, about 0.2 to 0.3 mL, about 0.3 to 0.4 mL, about 0.4 to 0.5 mL, about 0.5 to 0.6 mL, about 0.6 to 0.7 mL, about 0.7 to 0.8 mL, about 0.8 to 0.9 mL, about 0.9 to 1 mL, about 1 to 5 mL, or about 5 to 10 mL, as compared to a substantially identical but otherwise uncontacted plant. In some embodiments, the transpiration is increased by at least about 1%, 5%, 10%, 20%, 30%, 40%, 50%, 60%, 70%, 80%, 90%, 95%, or 99% as compared to a substantially identical but otherwise uncontacted plant. In some embodiments, the transpiration of the contacted plant is increased by about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

Disclosed herein is a method for eliciting hydraulic enhancement of a plant comprising contacting the plant with the compound, salt, solvate, or formulation, wherein a permanent wilting point of the contacted plant is decreased as compared to a substantially identical but otherwise uncontacted plant. Also disclosed herein is a method for decreased a permanent wilting point of a plant comprising contacting the plant with the compound, salt, solvate, or formulation, wherein the permanent wilting point of the contacted plant is decreased as compared to a substantially identical but otherwise uncontacted plant. In some embodiments, the permanent wilting point of the plant is measured as volumetric water content of soil ($m^3/m^3$). In some embodiments, the permanent wilting point of the contacted plant is decreased by at least about 0.005, 0010, 0.015, 0.020, 0.025, 0.030, 0.035, 0.040, 0.045, 0.050, 0.055, 0.060, 0.070, 0.080, 0.090, or 0.1 $m^3/m^3$, or from about 0.005 to about 0.1 $m^3/m^3$, for example about 0.005 to about 0.01, about 0.01 to about 0.02, about 0.02 to about 0.03, about 0.03 to about 0.04, about 0.04 to about 0.05, about 0.05 to about 0.06, about 0.06 to about 0.07, about 0.07 to about 0.08, about 0.08 to about 0.09, or about 0.09 to about 0.10, as compared to a substantially identical but otherwise uncontacted plant.

In some embodiments, the permanent wilting point of the contacted plant is decreased by at least about 1%, 5%, 10%, 20%, 30%, 40%, 50%, 60%, 70%, 80%, 90%, 95%, or 99% or from about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

Disclosed herein is a method for eliciting hydraulic enhancement of a plant comprising contacting the plant with the compound, salt, solvate, or formulation, wherein an average rate of cavitation in xylem of the contacted plant is decreased as compared to a substantially identical but otherwise uncontacted plant. Also disclosed herein is a method for decreased a permanent wilting point of a plant comprising contacting the plant with the compound, salt, solvate, or formulation, wherein the average rate of cavitation in xylem of the contacted plant is decreased as compared to a substantially identical but otherwise uncontacted plant. In some embodiments, the average rate of cavitation in xylem of the plant is measured by using an ultrasonic acoustic emission (UAE). In some embodiments, the average rate of cavitation in xylem of the contacted plant is decreased by at least about %, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

In some embodiments, the plant comprises a corn. In some embodiments, a production of the contacted corn is increased as compared to a substantially identical but otherwise uncontacted corn. In some embodiments, an average kernel mass (w/w) of the contacted corn is increased by at least about 1%, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-'70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted corn. In some embodiments, an average ear volume (v/v) of the contacted corn is increased by at least about 1%, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted corn.

In some embodiments, an average relative hydration of silks (w/w) of the contacted corn is increased by at least about 1%, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% as compared to a substantially identical but otherwise uncontacted corn. In some embodiments, an average mass of silks (w/w) of the contacted corn is increased by at least about 1%, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted corn.

In some embodiments, a life of the contacted plant is extended as compared to a substantially identical but otherwise uncontacted plant, a wilting of the contacted plant is reduced or delayed as compared to a substantially identical but otherwise uncontacted plant, a turgidity of the contacted plant is prolonged or maintained as compared to a substantially identical but otherwise uncontacted plant, a loss of one or more petals of the contacted plant is reduced or delayed as compared to a substantially identical but otherwise uncontacted plant, a chlorophyll content of the contacted plant is maintained as compared to a substantially identical but otherwise uncontacted plant, a loss of the chlorophyll content of the contacted plant is reduced or delayed as compared to a substantially identical but otherwise uncontacted plant, a chlorophyll content of the contacted plant is increased as compared to a substantially identical but otherwise uncontacted plant, a salinity tolerance of the contacted plant is increased as compared to a substantially identical but otherwise uncontacted plant, a water consumption of the contacted plant is reduced as compared to a substantially identical but otherwise uncontacted plant, a drought tolerance of the contacted plant is increased as compared to a substantially identical but otherwise uncontacted plant, a pest resistance of the contacted plant is increased as compared to a substantially identical but otherwise uncontacted plant, a pesticides consumption of the contacted plant is reduced as compared to a substantially identical but otherwise uncontacted plant, or any combination thereof.

In some embodiments, the yield of the contacted plant is increased under an adequately irrigated condition or a drought condition. In some embodiments, the contacting the plant comprises directly contacting the plant with the compound, salt, solvate, or formulation. In some embodiments, the contacting the plant comprises indirectly contacting the plant by contacting a soil surrounding the plant with the compound, salt, solvate, or formulation. In some embodiments, the contacting the plant comprises administering the compound, salt, solvate, or formulation as a spray. In some embodiments, the contacting the plant further comprises adding the compound, salt, solvate, or formulation to an irrigation water of the plant. In some embodiments, the contacting the plant comprises administering the compound, salt, solvate, or formulation as a spray. In some embodiments, the contacting the plant comprises administering the compound, salt, solvate, or formulation as a powder. In some embodiments, the plant is soybean, corn, rice, tomato, alfalfa, wheat, green algae or any combination thereof.

Also disclosed herein is a soil comprising the compound, salt, solvate, or formulation disclosed herein. Also disclosed herein is a plant grown in the soil, or an edible portion thereof. Also disclosed herein is a food comprising an ingredient from the plant, or an edible portion thereof. Also disclosed herein is a food comprising the compound, salt, solvate, or formulation.

Also disclosed herein is a method of making a formulation comprising contacting a compound, salt, or solvate of any proceeding claim with an excipient.

Also disclosed herein is a method of producing the compound, salt, or solvate of any proceeding claim, comprising reacting

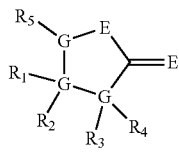

or a salt thereof. In some embodiments, the

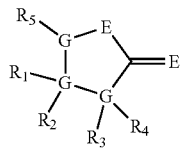

has a structure of

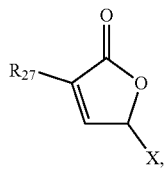

wherein $R_{27}$ is H, alkyl, halo, or haloalkyl, and X is Cl, Br, or I. In some embodiments, $R_{27}$ is alkyl. In some embodiments, $R_{27}$ is methyl. In some embodiments,

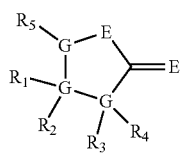

has a structure of

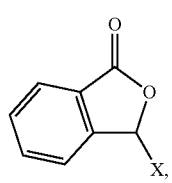

wherein X is Cl, Br, or I. In some embodiments, X is Cl.

Also disclosed herein are plants contacted by a compound, salt, solvate, or formulation disclosed herein, or an edible portion thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 7 shows improved silk tissue hydration with increasing AB01 dose.

FIG. 8 shows lower cumulative acoustic emission events (left) and lower event rate (rate) in hydraulic enhanced (AB01-treated) plants.

FIG. 9 shows field trial data from Fresno County, Calif. Hydraulic enhancement improved yield in both moderate and severe stress environments.

FIG. 10 shows field trial data from Brondal, South Africa. Hydraulic enhancement improved yield in unstressed environment.

FIG. 11 shows synthetic and natural strigolactones and AB01 for inducing hydraulic enhancement of crops.

FIG. 12 shows screen of AB compounds, including AB01, AB 06, AB07, AB08, Ab09, AB10, and AB12 for hydraulic enhancement.

FIG. 13 shows structure of AB09 and derivatives.

FIG. 14 shows abscisic acid inhibited hydraulic enhancement in a transpiration assay.

FIG. 15 shows application of the abscisic acid biosynthesis inhibitor fluridone (1 μg) improved hydraulic enhancement.

FIG. 16 shows application of the plant growth regulator gibberellic acid (GA) improved hydraulic enhancement.

FIG. 17 shows application of 1 μg cytokinin 6-benzylaminopurine (6-BAP) improved hydraulic enhancement.

DETAILED DESCRIPTION OF THE INVENTION

Definition

Unless defined otherwise, all technical and scientific terms used herein have the same meaning as commonly understood by one of the ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

The open terms for example "contain," "containing," "include," "including," and the like mean comprising.

The singular forms "a", "an", and "the" are used herein to include plural references unless the context clearly dictates otherwise.

Unless otherwise indicated, some embodiments herein contemplate numerical ranges. When a numerical range is provided, unless otherwise indicated, the range can include the range endpoints. Unless otherwise indicated, numerical ranges can include all values and subranges therein as if explicitly written out.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

The term "compounds" can refer to compounds encompassed by generic formulae disclosed herein, any subgenus of those generic formulae, and any specific compounds within those generic or subgeneric formulae. The compounds can be a specific specie, a subgenus or larger genus identified either by their chemical structure and/or chemical name. Further, compounds also include substitutions or modifications of any of such species, subgenuses or genuses, which are set forth herein. When the chemical structure and chemical name conflict, the chemical structure can bedeterminative of the identity of the compound. The compounds can contain one or more chiral centers and/or double bonds and therefore, can exist as stereoisomers, isomers, enantiomers or diastereomers. Accordingly, the chemical structures within the scope of the specification encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Further, when partial structures of the compounds are illustrated, asterisks indicate the point of attachment of the partial structure to the rest of the molecule. Enantiomeric and stereoisomeric mixtures can be resolved into their component enantiomers or stereoisomers using separation techniques or chiral synthesis techniques well known to the skilled artisan. The compounds can include any salt or solvate forms of the compounds. The compounds can include any derivatives of the compounds.

The term "derivative," which can be used interchangeably with the term "analog." Compound A can be a derivative or analog of compound B if 1, 2, 3, 4, or 5 atoms of compound A is replaced by another atom or a functional group (e.g., amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl) to form compound B.

to a chemical compound that is structurally similar to another but differs slightly in composition (as in the replacement of one atom by an atom of a different element or in the presence of a particular functional group)

The term "solvate" can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

Figure 1:
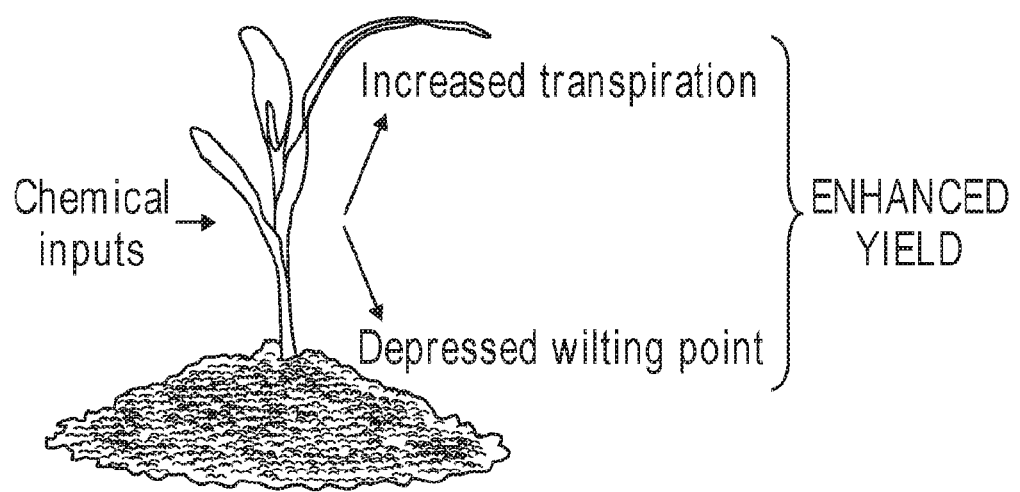
FIG. 1 shows hydraulic enhancement of crops results in plants with higher rates of transpiration and a lower permanent wilting point. The combined effects of these physiological outcomes can result in higher yield in environments with and/or without abiotic stress.

The term "salt" can include, but are not limited to, salts that retain one or more of the activities and properties of the free acids and bases and that are not undesirable. Illustrative examples of salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

Unless otherwise indicated, a chemical structure can refer to any compound having the chemical structure.

Unless otherwise indicated, formulations herein can be powdery.

Unless otherwise indicated, powder formulations herein can contain water in an amount from about 0% to about 15% w/w, for example 0-10%, 0-5%, or 0-1% w/w; or about: 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90% or 99% w/w, based on the weight of the formulation.

Unless otherwise indicated, whenever there is a stereocenter in a structure disclosed or illustrated herein, the stereocenter can be R or S in each case.

Unless otherwise indicated, whenever there is a symbol

when used as part of a molecular structure herein can refer to a single bond.

The term "amino" can refer to functional groups that contain
a basic nitrogen atom with a lone pair. For example, amino can include the radical

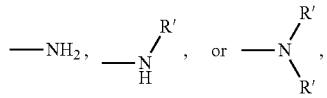

wherein each R' is independently H, halo, alkyl, aryl, heteroalkyl, arylalkyl, heteroaryl, heteroarylalkyl, cycloalkyl, or heterocycloalkyl.

The term "halo" or "halogen" can refer to fluorine, chlorine, bromine or iodine or a radical thereof.

The term "alkyl" can refer to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl; prop-1-en-2-yl, prop-2-en-1-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-di en-1-yl, buta-1,3-di en-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "aryl" can refer to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms.

The terms "heteroalkyl, heteroalkanyl, heteroalkenyl, heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to, —O—, —S—, —O—O', —S—S—, —O—S—, —NR'—, =N—N=, —N=N—, —N=N—NR'—, —PH—, —P(O)2-, —O—P(O)2-, —S(O)—, —S(O)2-, —SnH2- and the like, wherein R' is hydrogen, alkyl, substituted alkyl, cycloalkyl, substituted cycloalkyl, aryl or substituted aryl.

The term "heteroaryl" can refer to a monovalent heteroaromatic group derived by the removal of one hydrogen atom from a single atom of a parent heteroaromatic ring system. Typical heteroaryl groups include, but are not limited to, groups derived from acridine, arsindole, carbazole, O-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group is between 5-20 membered heteroaryl, and in other embodiments is between 5-10 membered heteroaryl. In certain embodiments heteroaryl groups are those derived from thiophene, pyrrole, benzothiophene, benzofuran, indole, pyridine, quinoline, imidazole, oxazole and pyrazine.

The term "arylalkyl" can refer to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$).

The term "heteroaryl" can refer to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group is between 5-20 membered heteroaryl, and in other embodiments is between 5-10 membered heteroaryl. In certain embodiments heteroaryl groups are those derived from thiophene, pyrrole, benzothiophene, benzofuran, indole, pyridine, quinoline, imidazole, oxazole and pyrazine.

The term "heteroarylalkyl" can refer to an acyclic alkyl group in which one of the hydrogen atoms bonded to a carbon atom, typically a terminal or $sp^a$ carbon atom, is replaced with a heteroaryl group. Where specific alkyl moieties are intended, the nomenclature heteroarylalkanyl, heteroarylalkenyl and/or heteroarylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl.

The term "cycloalkyl" can refer to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a certain embodiment, the cycloalkyl group is $(C_3-C_{10})$ cycloalkyl, or in certain embodiments $(C_3-C_6)$ cycloalkyl.

The term "heterocycloalkyl" can refer to a saturated or unsaturated cyclic alkyl group in which one or more carbon atoms (and any associated hydrogen atoms) are independently replaced with the same or different heteroatom. Typical heteroatoms to replace the carbon atom(s) include, but are not limited to, N, P, O, S, and Si. Typical heterocycloalkyl groups include, but are not limited to, groups derived from epoxides, imidazolidine, morpholine, piperazine, piperidine, pyrazolidine, pyrrolidine, quinuclidine, and the like.

The term "diastereomeric excess" (DE) can refer to the difference between the relative abundance of two diastereomers. For instance, if there are two diastereomers and their mole or weight percentages are A and B, then DE can be calculated as: $DE=[(A-B)/(A+B)]*100\%$. For example, if a mixture contains 75% of one diastereomer and 25% of the other diastereomer, the diastereomeric excess is 50%. In another example, if a mixture that is 95% of one diastereomer, the diastereomeric excess is 90%.

The term "enantiomeric excess" (EE) can refer to the difference between the relative abundance of two enantiomers. For instance, if there are two enantiomers and their mole or weight percentages are A and B, then EE can be calculated as: $EE=[(A-B)/(A+B)]*100\%$. For example, if a mixture contains 75% of one enantiomer and 25% of the other enantiomer, the enantiomeric excess is 50%. In another example, if a mixture that is 95% of one enantiomer, the enantiomeric excess is 90%.

The term "substituted" can refer to a group in which one or more hydrogen atoms are each independently replaced with the same or different substituent(s). Typical substituents include, but are not limited to halo, alkyl, aryl, heteroalkyl, arylalkyl, heteroaryl, heteroarylalkyl, cycloalkyl, and heterocycloalkyl.

Unless otherwise indicated, "treated" can refer to "contacted." Similarly, "untreated" can refer to "uncontacted."

The term "substantially identical plant" can refer to a plant of the same species as an earlier referenced plant. For example, a substantially identical but otherwise uncontacted plant belongs to the same species as a contacted plant. The substantially identical but otherwise uncontacted plant can have a height of about 80% to 120% of the contacted plant (as measured from the surrounding soil to the highest point of the plant) and/or can have a mass of about 80% to 120% of the contacted plant.

The term "drought" can mean conditions with less than 20 inches, 15 inches, 10 inches, or 5 inches of rainfall within the past 12 months. The term "drought" can also mean conditions with a Palmer Drought Severity Index (PDSI) of less than −1.0. The term "adequately irrigated condition" can mean a condition with more than 20 inches of rainfall within the past 12 months. The term "adequately irrigated condition" can mean a condition with a PDSI of more than −1.0.

The term "plant" can be used interchangeably with the term "crop" and can include, but is not limited to any crop, cultivated plant, fungus, or alga that is harvested for food, clothing, livestock fodder, biofuel, medicine, or other uses. For example, plants include field and greenhouse crops, including but not limited to broad acre crops, fruits and vegetables, perennial tree crops, and ornamentals. Plants include, but are not limited to sugarcane, pumpkin, maize (corn), wheat, rice, cassava, soybeans, hay, potatoes, cotton, tomato, alfalfa, and green algae. Plants also include, but are not limited to any vegetable, such as cabbage, turnip, turnip, carrot, parsnip, beetroot, lettuce, beans, broad beans, peas, potato, eggplant, tomato, cucumber, pumpkin, squash, onion, garlic, leek, pepper, spinach, yam, sweet potato, and cassava.

Introduction

Compounds, salts, solvates, and/or formulations described herein can be applied to a plant (e.g., to the seed, roots, or canopy of the plant). Compounds, salts, solvates, and/or formulations described herein can elicit hydraulic enhancement of a plant in stressed (e.g., drought) or unstressed environments. Hydraulic enhancement can be a physiological state where transpiration is increased and/or the wilting point of the crop is depressed. Hydraulic enhancement can promote tolerance of a plant to abiotic stress. Hydraulic enhancement can increase harvest yield in both stressed and unstressed environments. Disclosed herein are the compounds and formulations that can elicit hydraulic enhancement of the plant. Also disclosed herein are methods of making the compounds and/or formulations and methods of using the compounds and/or formulations.

AB Compounds

Disclosed herein are AB compounds comprise a compound of Formula (1):

Formula (1)

or any salt or solvate thereof,
wherein:
each E is independently O, S, or —NR$_7$;
each G is independently C or N;
R$_1$, R$_4$, R$_5$, and R$_6$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —OR$_8$, —C(O)R$_8$, or a lone electron pair, wherein indicates a single bond;
R$_2$ and R$_3$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, or a lone electron pair; or R$_2$ and R$_3$ together form a bond, or form a substituted or unsubstituted aryl; and
R$_7$ and R$_8$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or unsubstituted heterocycloalkyl.

In some embodiments, R$_2$ and R$_3$ together form a bond. In some embodiments, the compound, salt, or solvate has a structure of Formula (2):

Formula (2)

In some embodiments, R$_4$ is alkyl. In some embodiments, R$_4$ is methyl. In some embodiments, each G is independently C. In some embodiments, each G is independently N. In some embodiments, each E is independently O. In some embodiments, each E is independently S. In some embodiments, each E is independently —NR$_7$. In some embodiments, R$_1$ and R$_5$ is each independently H.

In some embodiments, the compound, salt, or solvate has a structure of Formula (3):

Formula (3)

In some embodiments, R$_6$ has a structure of Formula (4):

Formula (4)

wherein indicates a single bond.

In some embodiments, each E of the compound, salt, or solvate is independently O, S, or —NR$_7$. In some embodiments, each E is independently O. In some embodiments, each R$_7$ is independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl. In some embodiments, each R$_7$ is independently H or substituted or unsubstituted alkyl. In some embodiments, each R$_7$ is independently H.

In some embodiments, the compound, salt, or solvate has a structure of Formula (5):

Formula (5) [AB09]

In some embodiments, R_6 has a structure of Formula (6):

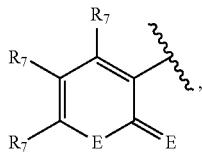

Formula (6)

wherein

indicates a single bond.

In some embodiments, R_6 has a structure selected from the group consisting of,

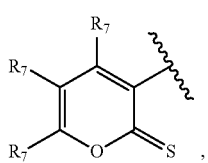 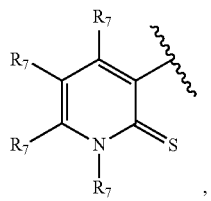

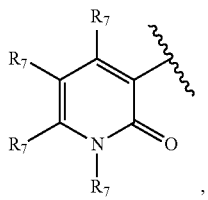 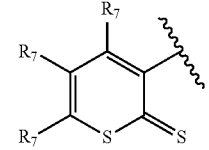

wherein

indicates a single bond.

In some embodiments, the compound, salt, or solvate has a structure selected from the group consisting of Formula (7), (8), (9), and (10):

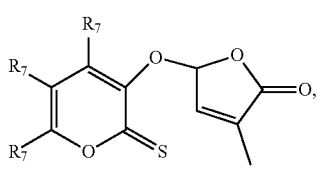

Formula (7)

Formula (8)

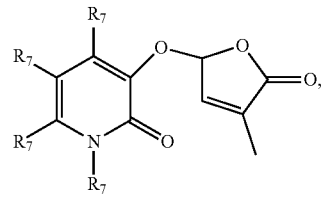

Formula (9)

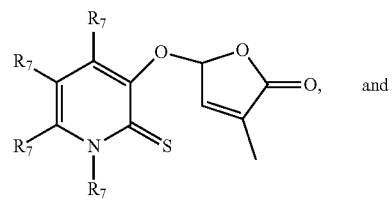

and

Formula (10)

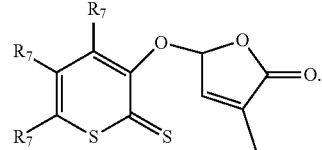

In some embodiments, R_6 has a structure of Formula (11):

Formula (11)

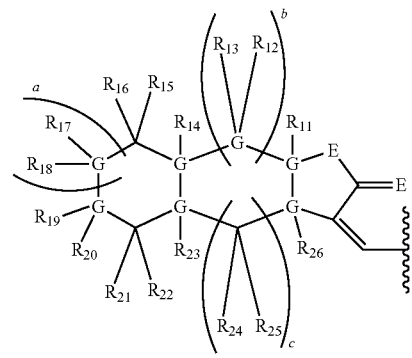

wherein:

indicates a single bond;

a, b, c are each independently 0, 1, or 2;

$R_{15}$, $R_{16}$, $R_{21}$, $R_{22}$, $R_{24}$, and $R_{25}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —OR_8, —C(O)R_8, or

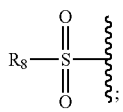

$R_{12}$, $R_{13}$, $R_{17}$, $R_{18}$, $R_{19}$, and $R_{20}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —$OR_8$, —$C(O)R_8$,

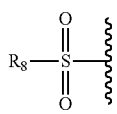

or a lone electron pair;

$R_{11}$ and $R_{26}$ are each independently H, alkyl, haloalkyl, amino, halo, lone electron pair, or —$OR_8$; or $R_{11}$ and $R_{26}$ together form a bond;

$R_{14}$ and $R_{23}$ are each independently H, alkyl, haloalkyl, amino, halo, lone electron pair, or —$OR_8$; or $R_{14}$ and $R_{23}$ together form a bond; and $R_8$ is each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl.

In some embodiments, the compound, salt, or solvate has a structure of Formula (12):

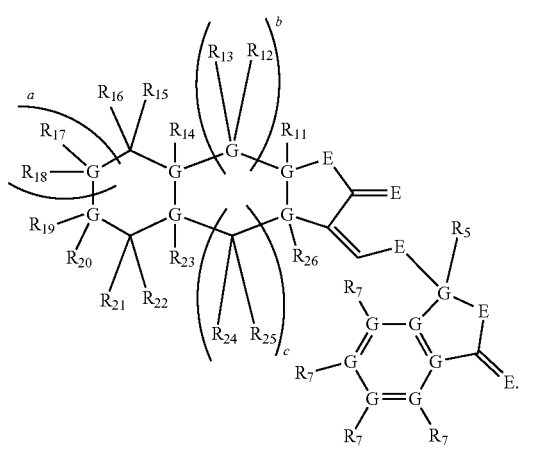

Formula (12)

In some embodiments, a, b, c are each independently 0, 1, or 2. The compound, salt, or solvate may be a compound, salt, or solvate, wherein a is 0, b is 0, and c is 0. The compound, salt, or solvate may be a compound, salt, or solvate, wherein a is 0, b is 0, and c is 1. The compound, salt, or solvate may be a compound, salt, or solvate, wherein a is 0, b is 0, and c is 2. The compound, salt, or solvate may be a compound, salt, or solvate, wherein a is 0, b is 1, and c is 0. The compound, salt, or solvate may be a compound, salt, or solvate, wherein a is 0, b is 1, and c is 1. The compound, salt, or solvate may be a compound, salt, or solvate, wherein a is 0, b is 1, and c is 2. The compound, salt, or solvate may be a compound, salt, or solvate, wherein a is 0, b is 2, and c is 0. The compound, salt, or solvate may be a compound, salt, or solvate, wherein a is 0, b is 2, and c is 1. The compound, salt, or solvate may be a compound, salt, or solvate, wherein a is 0, b is 2, and c is 2. The compound, salt, or solvate may be a compound, salt, or solvate, wherein a is 1, b is 0, and c is 0. The compound, salt, or solvate may be a compound, salt, or solvate, wherein a is 1, b is 0, and c is 1. The compound, salt, or solvate may be a compound, salt, or solvate, wherein a is 1, b is 0, and c is 2. The compound, salt, or solvate may be a compound, salt, or solvate, wherein a is 1, b is 1, and c is 0. The compound, salt, or solvate may be a compound, salt, or solvate, wherein a is 1, b is 1, and c is 1. The compound, salt, or solvate may be a compound, salt, or solvate, wherein a is 1, b is 1, and c is 2. The compound, salt, or solvate may be a compound, salt, or solvate, wherein a is 1, b is 2, and c is 0. The compound, salt, or solvate may be a compound, salt, or solvate, wherein a is 1, b is 2, and c is 1. The compound, salt, or solvate may be a compound, salt, or solvate, wherein a is 1, b is 2, and c is 2. The compound, salt, or solvate may be a compound, salt, or solvate, wherein a is 2, b is 0, and c is 0. The compound, salt, or solvate may be a compound, salt, or solvate, wherein a is 2, b is 0, and c is 1. The compound, salt, or solvate may be a compound, salt, or solvate, wherein a is 2, b is 0, and c is 2. The compound, salt, or solvate may be a compound, salt, or solvate, wherein a is 2, b is 1, and c is 0. The compound, salt, or solvate may be a compound, salt, or solvate, wherein a is 2, b is 1, and c is 1. The compound, salt, or solvate may be a compound, salt, or solvate, wherein a is 2, b is 1, and c is 2. The compound, salt, or solvate may be a compound, salt, or solvate, wherein a is 2, b is 2, and c is 0. The compound, salt, or solvate may be a compound, salt, or solvate, wherein a is 2, b is 2, and c is 1. The compound, salt, or solvate may be a compound, salt, or solvate, wherein a is 2, b is 2, and c is 2. In one example, the compound, salt, or solvate is a compound, salt, or solvate, wherein a is 1, b is 2, and c is 0.

In some embodiments, $R_6$ has a structure of Formula (13) or (14):

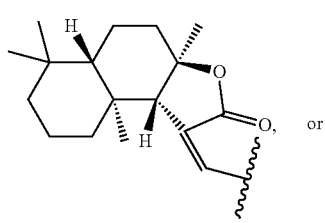

Formula (13)

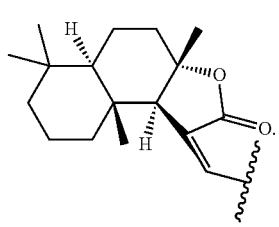

Formula (14)

In some embodiments, the compound, salt, or solvate has a structure of Formula (15) or (16):

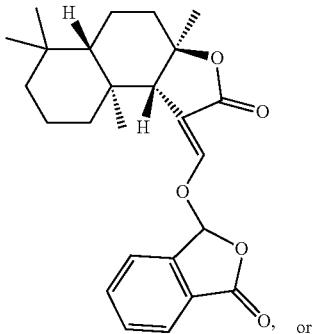

Formula (15)

or

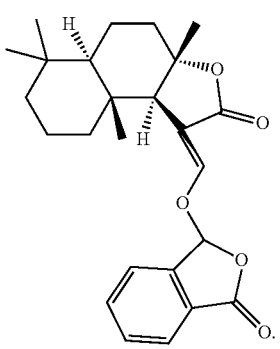

Formula (16)

In some embodiments, the compound, salt, or solvate is AB10, which has a structure of Formula (15) or (16).

In some embodiments, the compound, salt, or solvate is an isomer. In some embodiments, the compound, salt, or solvate is a stereoisomer.

In some embodiments, the compound, salt, or solvate is a diastereoisomer. In some embodiments, the compound, salt, or solvate is a diastereoisomer having a diastereomeric excess of at least about 50%, 60%, 70%, 80%, 85%, 90%, 95%, or from at least about 50% to 100%. The compound, salt, or solvate disclosed herein, may have a diastereomeric excess of at least about 15%, 20%, 30%, 40%, 50%, 60%, 70%, 80%, 85%, 90%, 95%, or 99%. The compound, salt, or solvate disclosed herein, may have a diastereomeric excess of about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20%. In one embodiment, the compound, salt, or solvate disclosed herein, may have a diastereomeric excess of from at least about 50% to 100%.

In some embodiments, the compound, salt, or solvate is an enantiomer. In some embodiments, the compound, salt, or solvate is an enantiomer having an enantiomeric excess of at least about 50%, 60%, 70%, 80%, 85%, 90%, 95%, or from at least about 50% to 100%. The compound, salt, or solvate disclosed herein, may have an enantiomeric excess of at least about 15%, 20%, 30%, 40%, 50%, 60%, 70%, 80%, 85%, 90%, 95%, or 99%. The compound, salt, or solvate disclosed herein, may have an enantiomeric excess of about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20%. In one embodiment, the compound, salt, or solvate disclosed herein, may have an enantiomeric excess of from at least about 50% to 100%.

In some embodiments, the compound, salt, or solvate has a structure of Formula (17):

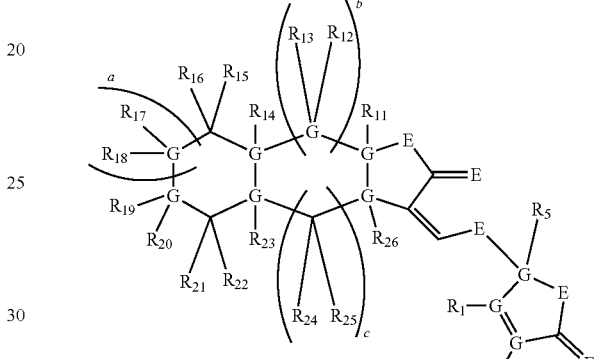

Formula (17)

wherein:
a, b, c are each independently 0, 1, or 2;
each E is independently 0, S, or —$NR_7$;
each G is independently C or N;
$R_1$, $R_4$, $R_5$, $R_{15}$, $R_{16}$, $R_{21}$, $R_{22}$, $R_{24}$, and $R_{25}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —$OR_8$, —$C(O)R_8$,

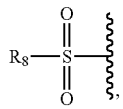

or wherein

indicates a single bond;
$R_{12}$, $R_{13}$, $R_{17}$, $R_{18}$, $R_{19}$, and $R_{20}$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, substituted or unsubstituted heterocycloalkyl, —OR$_8$, —C(O)R$_8$,

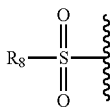

or a lone electron pair;

R$_{11}$ and R$_{26}$ are each independently H, alkyl, haloalkyl, amino, halo, lone electron pair, or —OR$_8$; or R$_{11}$ and R$_{26}$ together form a bond;

R$_{14}$ and R$_{23}$ are each independently H, alkyl, haloalkyl, amino, halo, lone electron pair, or —OR$_8$; or R$_{14}$ and R$_{23}$ together form a bond; and R$_7$ and R$_8$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl.

In some embodiments, a, b, c are each independently 0, 1, or 2. The compound, salt, or solvate may be a compound, salt, or solvate, wherein a is 0, b is 0, and c is 0. The compound, salt, or solvate may be a compound, salt, or solvate, wherein a is 0, b is 0, and c is 1. The compound, salt, or solvate may be a compound, salt, or solvate, wherein a is 0, b is 0, and c is 2. The compound, salt, or solvate may be a compound, salt, or solvate, wherein a is 0, b is 1, and c is 0. The compound, salt, or solvate may be a compound, salt, or solvate, wherein a is 0, b is 1, and c is 1. The compound, salt, or solvate may be a compound, salt, or solvate, wherein a is 0, b is 1, and c is 2. The compound, salt, or solvate may be a compound, salt, or solvate, wherein a is 0, b is 2, and c is 0. The compound, salt, or solvate may be a compound, salt, or solvate, wherein a is 0, b is 2, and c is 1. The compound, salt, or solvate may be a compound, salt, or solvate, wherein a is 0, b is 2, and c is 2. The compound, salt, or solvate may be a compound, salt, or solvate, wherein a is 1, b is 0, and c is 0. The compound, salt, or solvate may be a compound, salt, or solvate, wherein a is 1, b is 0, and c is 1. The compound, salt, or solvate may be a compound, salt, or solvate, wherein a is 1, b is 0, and c is 2. The compound, salt, or solvate may be a compound, salt, or solvate, wherein a is 1, b is 1, and c is 0. The compound, salt, or solvate may be a compound, salt, or solvate, wherein a is 1, b is 1, and c is 1. The compound, salt, or solvate may be a compound, salt, or solvate, wherein a is 1, b is 1, and c is 2. The compound, salt, or solvate may be a compound, salt, or solvate, wherein a is 1, b is 2, and c is 0. The compound, salt, or solvate may be a compound, salt, or solvate, wherein a is 1, b is 2, and c is 1. The compound, salt, or solvate may be a compound, salt, or solvate, wherein a is 1, b is 2, and c is 2. The compound, salt, or solvate may be a compound, salt, or solvate, wherein a is 2, b is 0, and c is 0. The compound, salt, or solvate may be a compound, salt, or solvate, wherein a is 2, b is 0, and c is 1. The compound, salt, or solvate may be a compound, salt, or solvate, wherein a is 2, b is 0, and c is 2. The compound, salt, or solvate may be a compound, salt, or solvate, wherein a is 2, b is 1, and c is 0. The compound, salt, or solvate may be a compound, salt, or solvate, wherein a is 2, b is 1, and c is 1. The compound, salt, or solvate may be a compound, salt, or solvate, wherein a is 2, b is 1, and c is 2. The compound, salt, or solvate may be a compound, salt, or solvate, wherein a is 2, b is 2, and c is 0. The compound, salt, or solvate may be a compound, salt, or solvate, wherein a is 2, b is 2, and c is 1. The compound, salt, or solvate may be a compound, salt, or solvate, wherein a is 2, b is 2, and c is 2. In one example, the compound, salt, or solvate is a compound, salt, or solvate, wherein a is 1, b is 2, and c is 0.

In some embodiments, the compound, salt, or solvate has a structure of Formula (18) or (19):

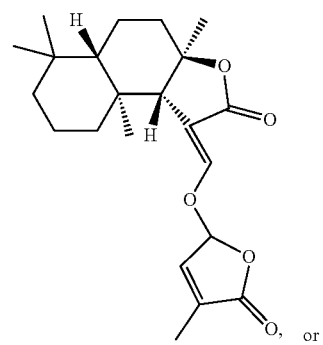

Formula (18)

, or

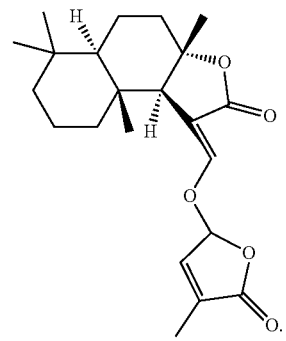

Formula (19)

In some embodiments, the compound, salt, or solvate is AB01, which has a structure of Formula (18) or (19).

In some embodiments, R$_2$ and R$_3$ together form a substituted or unsubstituted aryl.

In some embodiments, the compound, salt, or solvate has a structure of Formula (20):

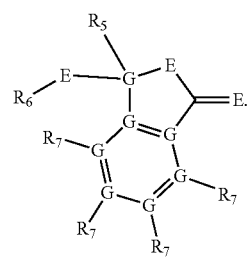

Formula (20)

In some embodiments, each R$_7$ is independently H. In some embodiments, each G is independently C. In some embodiments, each E is independently O. In some embodiments, R$_5$ is independently H.

In some embodiments, the compound, salt, or solvate has a structure of Formula (21):

Formula (21)

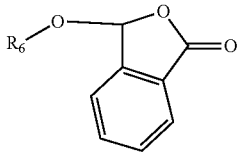

In some embodiments, $R_6$ has a structure selected from the group consisting of

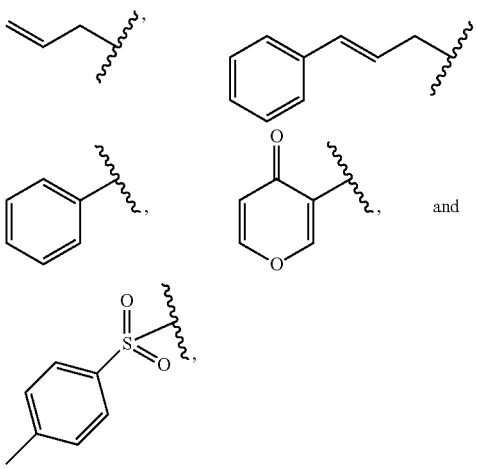

wherein

indicates a single bond.

In some embodiments, the compound, salt, or solvate has a structure selected from the group consisting of Formula (22), (23), (24), (25), and (26):

Formula (22) [AB06]

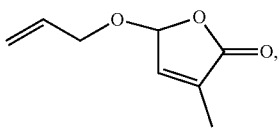

Formula (23) [AB07]

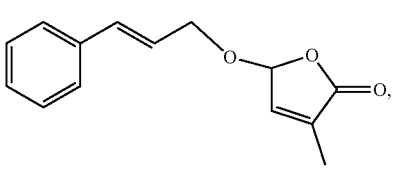

Formula (24) [AB08]

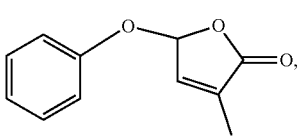

-continued

Formula (25) [AB09]

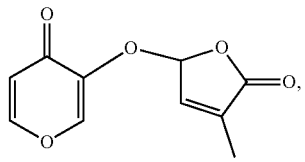

and

Formula (26) [AB12]

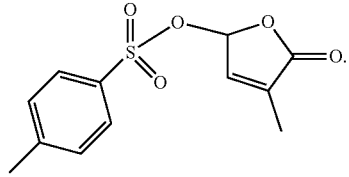

In some embodiments, the compound, salt, or solvate is an isomer. In some embodiments, the compound, salt, or solvate is a stereoisomer.

In some embodiments, the compound, salt, or solvate is a diastereoisomer. In some embodiments, the compound, salt, or solvate is a diastereoisomer having a diastereomeric excess of at least about 50%, 60%, 70%, 80%, 85%, 90%, 95%, or from at least about 50% to 100%. The compound, salt, or solvate disclosed herein, may have a diastereomeric excess of at least about 15%, 20%, 30%, 40%, 50%, 60%, 70%, 80%, 85%, 90%, 95%, or 99%. The compound, salt, or solvate disclosed herein, may have a diastereomeric excess of about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20%. In one embodiment, the compound, salt, or solvate disclosed herein, may have a diastereomeric excess of from at least about 50% to 100%.

In some embodiments, the compound, salt, or solvate is an enantiomer. In some embodiments, the compound, salt, or solvate is an enantiomer having an enantiomeric excess of at least about 50%, 60%, 70%, 80%, 85%, 90%, 95%, or from at least about 50% to 100%. The compound, salt, or solvate disclosed herein, may have an enantiomeric excess of at least about 15%, 20%, 30%, 40%, 50%, 60%, 70%, 80%, 85%, 90%, 95%, or 99%. The compound, salt, or solvate disclosed herein, may have an enantiomeric excess of about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20%. In one embodiment, the compound, salt, or solvate disclosed herein, may have an enantiomeric excess of from at least about 50% to 100%.

In one embodiment, the compound, salt, or solvate disclosed herein is not (+)-Strigol

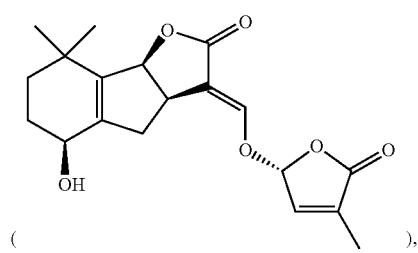 [SMILES: CC1=C[C@H](O/C=C2/C(=O)O[C@@H]3C4=C(C[C@H]23)[C@@H](O)CCC4(C)C)OC1=O]

(+)-Strigyl acetate

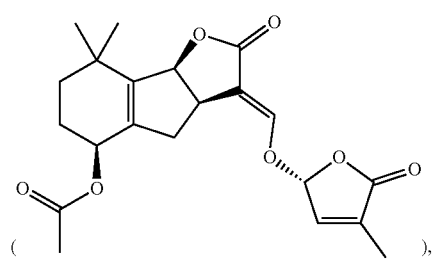 [SMILES: CC(=O)O[C@H]1CCC(C)(C)C2=C1C[C@@H]1/C(=C\O[C@H]3C=C(C)C(=O)O3)C(=O)O[C@H]21]

(+)-Orobanchol

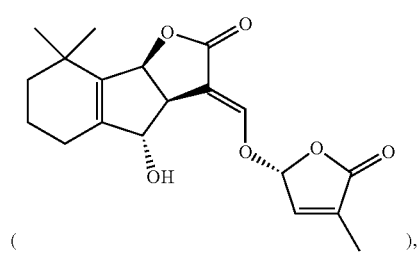 [SMILES: CC1=C[C@H](O/C=C2/C(=O)O[C@@H]3C4=C(CCCC4(C)C)[C@@H](O)[C@H]23)OC1=O]

(+)-Orobanchyl acetate

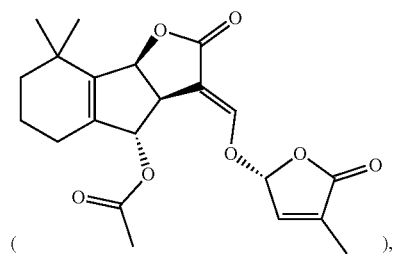 [SMILES: CC(=O)O[C@@H]1C2=C([C@H]3OC(=O)/C(=C/O[C@H]4C=C(C)C(=O)O4)[C@@H]13)C(C)(C)CCC2]

(+)-5-Deoxystrigol

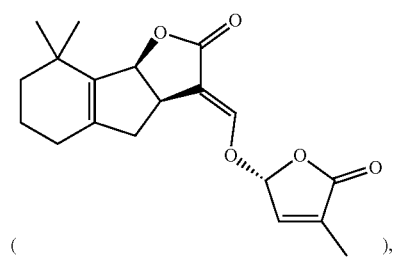 [SMILES: CC1=C[C@H](O/C=C2/C(=O)O[C@@H]3C4=C(CCCC4(C)C)C[C@H]23)OC1=O]

Sorgolactone

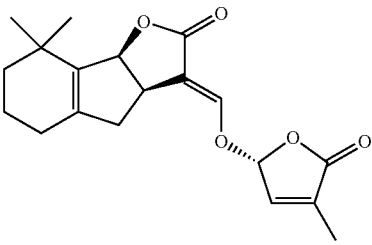

or any combination thereof.

Formulations

Also disclosed herein are formulations comprising:
one or more AB compounds, salts or solvates,
one or more strigolactones, salts, or solvates,
one or more inhibitors of abscisic acid biosynthesis, or any salt or solvate thereof,
one or more plant growth regulators, or any salt or solvate thereof,
or any combination thereof.

The formulation can be as a seed treatment, soil drench, granule formulation, or foliar spray to improve the productivity of a wide variety of crops.

AB Compounds

Further disclosed herein are formulations comprising one or more AB compounds, salts or solvates. The one or more AB compounds, salts or solvates can elicit hydraulic enhancement of a plant. The one or more AB compounds, salts or solvates can increase harvest yield of the plant. The one or more AB compounds, salts or solvates can comprise AB01, AB06, AB07, AB08, AB09, AB10, AB10, AB12, or any salt, solvate, or derivative thereof. The one or more AB compounds, salts or solvates thereof can comprise AB09, or any salt, solvate, or derivative thereof.

The formulation comprising one or more AB compounds, salts or solvates can further comprise one or more strigolactones, salts, or solvates. The formulation comprising one or more AB compounds, salts or solvates can further comprise one or more plant growth regulators (PGRs), salts or solvates. The formulation comprising one or more AB compounds, salts or solvates can further comprise one or more inhibitors of abscisic acid (ABA) biosynthesis, or any salt or solvate thereof. The formulation comprising one or more AB compounds, salts or solvates can further comprise one or more strigolactones, salts, or solvates and one or more plant growth regulators (PGRs), salts, or solvates. The formulation comprising one or more AB compounds, salts or solvates can further comprise one or more strigolactones, salts, or solvates and one or more inhibitors of abscisic acid (ABA) biosynthesis, or any salt or solvate thereof. The formulation comprising one or more AB compounds, salts or solvates can further comprise one or more plant growth regulators (PGRs), salts, or solvates and one or more inhibitors of abscisic acid (ABA) biosynthesis, or any salt or solvate thereof.

The formulations may comprise at least about 0.1% (w/w) of an AB compound, salt or solvate, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the AB compound, salt or solvate.

The formulations may comprise less than about 95% (w/w) of an AB compound, salt or solvate, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the AB compound, salt or solvate.

The formulations may comprise about 0.1%-100% (w/w) of an AB compound, salt or solvate, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%40%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of the AB compound, salt or solvate.

AB01

The formulations may comprise at least about 0.1% (w/w) of AB01, or any salt or solvate thereof, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of AB01, or any salt or solvate thereof.

The formulations may comprise less than about 95% (w/w) of AB01, or any salt or solvate thereof, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of AB01, or any salt or solvate thereof.

The formulations may comprise about 0.1%-100% (w/w) of AB01, or any salt or solvate thereof, for example, about 0.1%-1%, 0.1%-5%, about 0.1-10%, about 0.1%-20%, about 0.5%-1%, about 0.5%-5%, about 0.5%40%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of AB01, or any salt or solvate thereof.

AB09

The formulations may comprise at least about 0.1% (w/w) of AB09, or any salt or solvate thereof, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of AB09, or any salt or solvate thereof.

The formulations may comprise less than about 95% (w/w) of AB09, or any salt or solvate thereof, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of AB09, or any salt or solvate thereof.

The formulations may comprise about 0.1%-100% (w/w) of AB09, or any salt or solvate thereof, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of AB09, or any salt or solvate thereof.

AB09 Derivatives

The formulations may comprise at least about 0.1% (w/w) of an AB09 derivative, or any salt or solvate thereof, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the AB09 derivative, or any salt or solvate thereof.

The formulations may comprise less than about 95% (w/w) of an AB09 derivative, or any salt or solvate thereof, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the AB09 derivative, or any salt or solvate thereof.

The formulations may comprise about 0.1%-100% (w/w) of an AB09 derivative, or any salt or solvate thereof, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the AB09 derivative, or any salt or solvate thereof.

Strigolactones

Further disclosed herein are formulations comprising one or more strigolactones, salts, or solvates. The one or more strigolactones, salts, or solvates can elicit hydraulic enhancement of a plant. The one or more strigolactones, salts, or solvates can increase harvest yield of the plant. The one or more strigolactones, salts, or solvates can comprise one or more natural strigolactones, salts, or solvates. The one or more strigolactones, salts, or solvates can comprise one or more synthetic strigolactones, salts, or solvates. The one or more strigolactones, salts, or solvates can comprise a mixture of natural and synthetic strigolactones, salts, or solvates. The one or more strigolactones, salts, or solvates can comprise strigol, strigyl, strigyl acetate, orobanchol, orobanchyl acetate, 5-deoxystrigol, sorgolactone, 2'-epi-orobanchol, sorgomol, solanacol, 7-oxoorobanchol, 7-oxoorobanchol acetate, fabacyl acetate, or GR24. The formulation can comprise a mixture of strigolactones, salts, or solvates. The mixture of strigolactones, salts, or solvates may comprise two or more strigolactones, salts, or solvates selected from the group consisting of strigol, strigyl, strigyl acetate, orobanchol, orobanchyl acetate, 5-deoxystrigol, sorgolactone, 2'-epiorobanchol, sorgomol, so-lanacol, 7-oxoorobanchol, 7-oxoorobanchol acetate, fabacyl acetate, or GR24.

The formulation comprising one or more strigolactones, salts, or solvates can further comprise one or more AB compounds, salts or solvates. The formulation comprising one or more strigolactones, salts, or solvates can further comprise one or more plant growth regulators (PGRs), salts, or solvates. The formulation comprising one or more strigolactones, salts, or solvates can further comprise one or more inhibitors of abscisic acid (ABA) biosynthesis, or any salt or solvate thereof. The formulation comprising one or more strigolactones, salts, or solvates can further comprise one or more AB compounds, salts or solvates and one or more plant growth regulators (PGRs), salts, or solvates. The formulation comprising one or more strigolactones, salts, or solvates can further comprise one or more AB compounds, salts or solvates and one or more inhibitors of abscisic acid (ABA) biosynthesis, or any salt or solvate thereof. The formulation comprising one or more strigolactones, salts, or solvates can further comprise one or more plant growth regulators (PGRs), salts, or solvates and one or more inhibitors of abscisic acid (ABA) biosynthesis, or any salt or solvate thereof.

The formulations may comprise at least about 0.1% (w/w) of a strigolactone, salt, or solvate, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the strigolactone, salt, or solvate.

The formulations may comprise less than about 95% (w/w) of a strigolactone, salt, or solvate, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the strigolactone, salt, or solvate.

The formulations may comprise about 0.1%-100% (w/w) of a strigolactone, salt, or solvate, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the strigolactone, salt, or solvate.

Strigol

The formulations may comprise at least about 0.1% (w/w) of strigol, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of strigol.

The formulations may comprise less than about 95% (w/w) of strigol, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of strigol.

The formulations may comprise about 0.1%-100% (w/w) of strigol, for example, about 0.1%-1%, 0.1%-5%, about 0.1%-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of strigol.

Strigyl

The formulations may comprise at least about 0.1% (w/w) of strigyl, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of strigyl.

The formulations may comprise less than about 95% (w/w) of strigyl, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of strigyl.

The formulations may comprise about 0.1%-100% (w/w) of strigyl, for example, about 0.1%-1%, 0.1%-5%, about 0.1%-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of strigyl.

Strigyl Acetate

The formulations may comprise at least about 0.1% (w/w) of strigyl acetate, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of strigyl acetate.

The formulations may comprise less than about 95% (w/w) of strigyl acetate, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of strigyl acetate.

The formulations may comprise about 0.1%-100% (w/w) of strigyl acetate, for example, about 0.1%-1%, 0.1%-5%, about 0.1%-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of strigyl acetate.

Orobanchol

The formulations may comprise at least about 0.1% (w/w) of orobanchol, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of orobanchol.

The formulations may comprise less than about 95% (w/w) of orobanchol, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of orobanchol.

The formulations may comprise about 0.1%-100% (w/w) of orobanchol, for example, about 0.1%-1%, 0.1%-5%, about 0.1%-10%, about 0.1%-20%, about 0.5%-1%, about 0.5%-5%, about 0.5%40%, about 0.5%-20%, about 1%-5%, about 1%40%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of orobanchol.

Orobanchyl Acetate

The formulations may comprise at least about 0.1% (w/w) of orobanchyl acetate, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of orobanchyl acetate.

The formulations may comprise less than about 95% (w/w) of orobanchyl acetate, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of orobanchyl acetate.

The formulations may comprise about 0.1%-100% (w/w) of orobanchyl acetate, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-'70%, about 60%-'70%, about 60%-80%, about 70%-80%, about 70%-90%, about 80%-90%, about 80%-95%, about 90%-95%, about 90%-99%, about 90%-100%, about 95%-99%, or about 99%-100% of orobanchyl acetate.

5-Deoxystrigol

The formulations may comprise at least about 0.1% (w/w) of 5-deoxystrigol, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of 5-deoxystrigol.

The formulations may comprise less than about 95% (w/w) of 5-deoxystrigol, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of 5-deoxystrigol.

The formulations may comprise about 0.1%-100% (w/w) of 5-deoxystrigol, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of 5-deoxystrigol.

Sorgolactone

The formulations may comprise at least about 0.1% (w/w) of sorgolactone, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of sorgolactone.

The formulations may comprise less than about 95% (w/w) of sorgolactone, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of sorgolactone.

The formulations may comprise about 0.1%-100% (w/w) of sorgolactone, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of sorgolactone.

2'-Epiorobanchol

The formulations may comprise at least about 0.1% (w/w) of 2'-epiorobanchol, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of 2'-epiorbanchol.

The formulations may comprise less than about 95% (w/w) of 2'-epiorbanchol, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of 2'-epiorbanchol.

The formulations may comprise about 0.1%-100% (w/w) of 2'-epiorbanchol, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of 2'-epiorbanchol.

Sorgomol

The formulations may comprise at least about 0.1% (w/w) of sorgomol, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of sorgomol.

The formulations may comprise less than about 95% (w/w) of sorgomol, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of sorgomol.

The formulations may comprise about 0.1%-100% (w/w) of sorgomol, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of sorgomol.

Solanacol

The formulations may comprise at least about 0.1% (w/w) of solanacol, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of solanacol.

The formulations may comprise less than about 95% (w/w) of solanacol, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of solanacol.

The formulations may comprise about 0.1%-100% (w/w) of solanacol, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of solanacol.

7-Oxoorobanchol

The formulations may comprise at least about 0.1% (w/w) of 7-oxoorobanchol, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of 7-oxoorobanchol.

The formulations may comprise less than about 95% (w/w) of 7-oxoorobanchol, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of 7-oxoorobanchol.

The formulations may comprise about 0.1%-100% (w/w) of 7-oxoorobanchol, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of 7-oxoorobanchol.

7-Oxoorobanchol Acetate

The formulations may comprise at least about 0.1% (w/w) of 7-oxoorobanchol acetate, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of 7-oxoorobanchol acetate.

The formulations may comprise less than about 95% (w/w) of 7-oxoorobanchol acetate, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of 7-oxoorobanchol acetate.

The formulations may comprise about 0.1%-100% (w/w) of 7-oxoorobanchol acetate, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of 7-oxoorobanchol acetate.

Fabacyl Acetate

The formulations may comprise at least about 0.1% (w/w) of fabacyl acetate, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of fabacyl acetate.

The formulations may comprise less than about 95% (w/w) of fabacyl acetate, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of fabacyl acetate.

The formulations may comprise about 0.1%-100% (w/w) of fabacyl acetate, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of fabacyl acetate.

GR24

The formulations may comprise at least about 0.1% (w/w) of GR24, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of GR24.

The formulations may comprise less than about 95% (w/w) of GR24, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of GR24.

The formulations may comprise about 0.1%-100% (w/w) of GR24, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of GR24.

ABA Biosynthesis Inhibitors

The formulation can comprise one or more inhibitors of abscisic acid (ABA) biosynthesis, or any salt or solvate thereof. The inhibitors of abscisic acid biosynthesis, or any salt or solvate thereof can elicit hydraulic enhancement of a plant. The inhibitors of abscisic acid biosynthesis, or any salt or solvate thereof can increase harvest yield of the plant. For example, Inhibitors of phytoene destaturase can elicit hydraulic enhancement of a plant and/or increase harvest yield of the plant. Therefore, the formulation can comprise one or more inhibitors of phytoene destaturase, such as fluridone or any one of its derivatives. Additional ABA biosynthetic inhibitors can include inhibitors of phytoene desaturase, inhibitors of 9-cis-epoxycarotenoid dioxygenase enzyme (NCED), and inhibitors of abscisic aldehyde oxidase (AAO). The formulation can comprise one or more such compounds such as nordihydroguaiaretic acid, abamine, or any one of their derivatives.

The formulation comprising one or more inhibitors of abscisic acid (ABA) biosynthesis, or any salt or solvate thereof can further comprise one or more AB compounds, salts or solvates. The formulation comprising one or more inhibitors of abscisic acid (ABA) biosynthesis, or any salt or solvate thereof can further comprise one or more strigolactones, salts, or solvates. The formulation comprising one or more inhibitors of abscisic acid (ABA) biosynthesis, or any salt or solvate thereof can further comprise one or more plant growth regulators (PGRs), salts, or solvates. The formulation comprising one or more inhibitors of abscisic acid (ABA) biosynthesis, or any salt or solvate thereof can further comprise one or more AB compounds, salts or solvates and one or more strigolactones, salts, or solvates. The formulation comprising one or more inhibitors of abscisic acid (ABA) biosynthesis, or any salt or solvate thereof can further comprise one or more AB compounds, salts or solvates and one or more plant growth regulators (PGRs), salts, or solvates. The formulation comprising one or more inhibitors of abscisic acid (ABA) biosynthesis, or any salt or solvate thereof can further comprise one or more strigolactones, salts, or solvates and one or more plant growth regulators (PGRs), salts, or solvates.

The formulations may comprise at least about 0.1% (w/w) of an inhibitor of abscisic acid (ABA) biosynthesis, or any salt or solvate thereof, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the inhibitor of abscisic acid (ABA) biosynthesis, or any salt or solvate thereof.

The formulations may comprise less than about 95% (w/w) of an inhibitor of abscisic acid (ABA) biosynthesis, or any salt or solvate thereof, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the inhibitor of abscisic acid (ABA) biosynthesis, or any salt or solvate thereof.

The formulations may comprise about 0.1%-100% (w/w) of an inhibitor of abscisic acid (ABA) biosynthesis, or any salt or solvate thereof, for example, about 0.1%-1%, 0.1%-5%, about 0.1-10%, about 0.1%-20%, about 0.5%4%, about 0.5%-5%, about 0.5%40%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the inhibitor of abscisic acid (ABA) biosynthesis, or any salt or solvate thereof.

Fluridone

The formulations may comprise at least about 0.1% (w/w) of fluridone, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of fluridone.

The formulations may comprise less than about 95% (w/w) of fluridone, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of fluridone.

The formulations may comprise about 0.1%-100% (w/w) of fluridone, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%40%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of fluridone.

Nordihydroguaiaretic Acid

The formulations may comprise at least about 0.1% (w/w) of nordihydroguaiaretic acid, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of nordihydroguaiaretic acid.

The formulations may comprise less than about 95% (w/w) of nordihydroguaiaretic acid, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of nordihydroguaiaretic acid.

The formulations may comprise about 0.1%-100% (w/w) of nordihydroguaiaretic acid, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-'70%, about 60%-'70%, about 60%-80%, about 70%-80%, about 70%-90%, about 80%-90%, about 80%-95%, about 90%-95%, about 90%-99%, about 90%400%, about 95%-99%, or about 99%-100% of nordihydroguaiaretic acid.

Abamine

The formulations may comprise at least about 0.1% (w/w) of abamine, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of abamine.

The formulations may comprise less than about 95% (w/w) of abamine, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of abamine.

The formulations may comprise about 0.1%-100% (w/w) of abamine, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of abamine.

Plant Growth Regulators (PGRs)

The formulation can comprise one or more plant growth regulators (PGRs), salts, or solvates. PGRs can be numerous chemical substances that can influence the growth and/or differentiation of plant cells, tissues, or organs. Plant growth regulators can function as chemical messengers for intercellular communication. PGRs can include auxins, gibberellins, cytokinins, abscisic acid (ABA) and ethylene, brassinosteroids, and polyamines. They can work together coordinating the growth and/or development of cells. PGRs can elicit hydraulic enhancement of a plant. PGRs can increase the harvest yield of a plant. Auxins can comprise indole-3-acetic acid (IAA) or its derivative or chemical analog.

The formulation comprising one or more plant growth regulators (PGRs), salts, or solvates can further comprise one or more AB compounds, salts or solvates. The formulation comprising one or more plant growth regulators (PGRs), salts, or solvates can further comprise one or more strigolactones, salts, or solvates. The formulation comprising one or more plant growth regulators (PGRs), salts, or solvates can further comprise one or more inhibitors of abscisic acid (ABA) biosynthesis, or any salt or solvate thereof. The formulation comprising one or more plant growth regulators (PGRs), salts, or solvates can further comprise one or more AB compounds, salts or solvates and one or more strigolactones, salts, or solvates. The formulation comprising one or more plant growth regulators (PGRs), salts, or solvates can further comprise one or more AB compounds, salts or solvates and one or more inhibitors of abscisic acid (ABA) biosynthesis, or any salt or solvate thereof. The formulation comprising one or more plant growth regulators (PGRs), salts, or solvates can further comprise one or more strigolactones, salts, or solvates and one or more inhibitors of abscisic acid (ABA) biosynthesis, or any salt or solvate thereof.

The formulations may comprise at least about 0.1% (w/w) of a plant growth regulator (PGR), salt, or solvate, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the PGR, salt, or solvate.

The formulations may comprise less than about 95% (w/w) of a PGR, salt, or solvate, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the PGR, salt, or solvate.

The formulations may comprise about 0.1%-100% (w/w) of a PGR, salt, or solvate, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-'70%, about 60%-80%, about 70%-80%, about 70%-90%, about 80%-90%, about 80%-95%, about 90%-95%, about 90%-99%, about 90%-100%, about 95%-99%, or about 99%-100% of the PGR, salt, or solvate.

Auxins (e.g., IAA)

The formulations may comprise at least about 0.1% (w/w) of an auxin (e.g., IAA), for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the auxin (e.g., IAA).

The formulations may comprise less than about 95% (w/w) of an auxin (e.g., IAA), for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the auxin (e.g., IAA).

The formulations may comprise about 0.1%-100% (w/w) of an auxin (e.g., IAA), for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the auxin (e.g., IAA).

Gibberellins

The formulations may comprise one or more gibberellins, such as GA1, GA3, GA4, GA7, GAO, ent-gibberellane, ent-kaurene, their derivatives and chemical analogs. The formulations may comprise at least about 0.1% (w/w) of a gibberellin, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the gibberellin.

The formulations may comprise less than about 95% (w/w) of a gibberellin, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the gibberellin.

The formulations may comprise about 0.1%-100% (w/w) of a gibberellin, for example, about 0.1%-1%, 0.1%-5%, about 0.1-10%, about 0.1%-20%, about 0.5%-1%, about 0.5%-5%, about 0.5%40%, about 0.5%-20%, about 1%-5%, about 1%40%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% of the gibberellin.

Cytokinins

The formulations may comprise one or more cytokinins, such as kinetin, zeatin, 6-benzylaminopurine, diphenylurea, thidiazuron, their derivatives and chemical analogs. The formulations may comprise at least about 0.1% (w/w) of a cytokinin, for example, at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the cytokinin.

The formulations may comprise less than about 95% (w/w) of a cytokinin, for example, less than about 0.1%, less than about 0.2%, less than about 0.3%, less than about 0.4%, less than about 0.5%, less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% of the cytokinin.

The formulations may comprise about 0.1%-100% (w/w) of a cytokinin, for example, about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%400%, about 95%-99%, or about 99%-100% of the cytokinin.

Excipients

The formulations disclosed herein may further comprise one or more excipients. The one or more excipients can be one or more pesticides, one or more stabilizers, one or more additives, one or more carriers, one or more dispersants, one or more fertilizer, or any combination thereof. In one example, one or more excipients comprise acetone.

The formulations disclosed herein may further comprise one or more pesticides. The pesticide may be a biopesticide. A biopesticide may be a form of a pesticide that can be based on microorganisms or natural products. A biopesticide may include naturally occurring substances that control pests (biochemical pesticides), microorganisms that control pests (microbial pesticides), and pesticidal substances produced by plants containing added genetic material (plant-incorporated protectants) or PIPs. Examples of biopesticides can include, but are not limited to, gluocosinolate, chitosan, spinosad, alkaloids, terpenoids, phenolics, pyrethroids, rotenoids, nicotinoids, strychnine, scilliroside, canola oil and baking soda. The pesticide may be an organophosphate pesticide, carbamate pesticide, organochlorine insecticide, pyrethroid pesticide, sulfonylurea pesticides, or a combination thereof. The pesticide may be a herbicide, algicide, avidicide, bactericide, fungicide, insecticide, miticide, molluscicide, nematicide, rodenticide, virucide, or a combination thereof.

The formulations may further comprise one or more stabilizers and/or other additives. The stabilizers and/or additives can include, but are not limited to, penetration agents, adhesives, anticaking agents, dyes, dispersants, wetting agents, emulsifying agents, defoamers, antimicrobials, antifreeze, pigments, colorants, buffers, and carriers. The formulations may further comprise surfanctans and/or adjuvants.

The formulations may further comprise one or more carriers. Examples of carriers include, but are not limited to, solid carriers, sponges, textiles, and synthetic materials. The synthetic material may be a porous synthetic material. Additional carriers can include organic carriers, such as waxes, linolin, paraffin, dextrose granules, sucrose granules and maltose-dextrose granules. Alternatively, the carrier can be an anorganic carrier such as natural clays, kaolin, pyrophyllite, bentonite, alumina, montmorillonite, kieselguhr, chalk, diatomaceous earths, calcium phosphates, calcium and magnesium carbonates, sulphur, lime, flours or talc. The formulation may be adsorbed into the carrier. The carrier may be characterized by enabling release of the compound, salt, solvate, or formulation.

The formulations may further comprise one or more dispersants. The dispersant may be an negatively charged anion dispersant. The dispersant may be a nonionic dispersant.

The formulations may further comprise fertilizer. The fertilizer may be a chemical fertilizer. The fertilizer may be an organic fertilizer. The fertilizer may be an inorganic fertilizer. The fertilizer may be a granulated or powdered fertilizers. The fertilizer may be a liquid fertilizer. The fertilizer may be a slow-release fertilizer.

The formulations disclosed herein may be formulated as a dry sprayable formulation. Examples of dry sprayable formulations can include, but are not limited to, wettable powders and water dispersible granules. Wettable powders may comprise compounds, salts, solvates, that have been microionized to powder form. Wettable powders may be applied as suspended particles after dispertion into water. Water dispersible granules may consist of granules that are applied after disintegration or dispersion in water. The water dispersible granules may comprise particles within the range of 0.2 to 4 mm. Water dispersible granules may be formed by agglomeration, spray drying, or extrusion techniques.

The formulations may be formulated as a liquid sprayable formulation. Examples of liquid sprayable formulations can include, but are not limited to, soluble concentrates, suspension concentrates, emulsifiable concentrates, microemulsions, oil dispersions, and microencapsulated particles. Suspension concentrates may comprise a stable suspension of the compound, salt, solvate, or formulation in a fluid usually intended for dilution with water before use. Emulsifiable concentrates may comprise a compound, salt, solvate, or formulation with an emulsifying agent in a water insoluble organic solvate which will form an emulsion when added to water. Microemulsions may comprise a compound, salt, solvate, or formulation with an emulsifying agent in a water insoluble organic solvate which will form a solution/emulsion when added to water.

The formulations may be formulated as a dry spreadable granule formulation. The dry spreadable granule formulation may comprise soil applied granule on inert or fertilizer carriers.

The formulations may be formulated as a seed treatment or seed dressing.

The formulations may be formulated for rapid release. The formulations may be formulated for slow release.

Methods of Eliciting Hydraulic Enhancement and Increasing Yield

Also disclosed herein are methods of eliciting hydraulic enhancement and/or increasing yield of a plant. The methods can comprise contacting the plant with the compounds, salts, solvates, or formulations disclosed herein. As shown in FIG. 1, hydraulic enhancement can be a physiological state where transpiration of the contacted plant is increased and/or the wilting point of the plant is decreased, as compared to a substantially identical but otherwise uncontacted plant. Hydraulic enhancement can lead to increased harvest yield in the contacted plant, as compared to a substantially identical but otherwise uncontacted plant. The method can be used in both stressed and non-stressed agronomic conditions. Hydraulic enhancement of plants can render them more resistant to abiotic stress and can result in higher yield in stressful conditions, as well as results in higher yields in unstressed conditions (e.g., with adequate water).

The compounds, salts, solvates, and formulations can be applied in multiple ways using application methods common in the crop protection input field to induce hydraulic enhancement of crops. For example, they can be applied as seed treatments, seed coatings, soil drench, top- or side-dressed granules, foliar sprays, or any combination of these application methods. The compounds can also be applied as co-formulations with crop inputs such as fertilizers, insecticides, herbicides, fungicides, micronutrients, and plant growth regulators. In addition, they can be applied via irrigation water (commonly referred to as 'chemigation').

Transpiration, the process of water movement through plants and its evaporation at the leaf-air interface, can be important to plant water physiology and hydraulics. Increased transpiration can lead to increased harvest yield. The control of water flux through the plant can be achieved by stomata, which regulate the entry of $CO_2$ into the plant for fixation by photosynthesis and/or the loss of water from the plant to the atmosphere.

Transpiration can be measured in a variety of ways. One simple method can be the use of a porometer (e.g., a hand-held leaf porometer), a device that can measure stomatal conductance via water vapor in a fixed chamber. The porometer can be used to measure the stomatal conductance of a plant. For example, the porometer can be used to measure the difference in transpiration between two corn plants (e.g., hybrid Dekalb 68-05), one contacted with a compound, salt, solvate, or formulation disclosed herein (e.g., AB01) and one that was uncontacted. Hydraulic enhancement via treatment can result in increased transpiration at all points throughout a 12-hour daylight cycle.

Increased transpiration can also have secondary effects on plant physiology, one of which can be a lower canopy temperature. Higher transpiration can result in better evaporative cooling of the leaf and/or canopy structures of a plant. To measure this phenomena, an infrared camera can be used to image plants that had been treated a compound, salt, solvate, or formulation disclosed herein (e.g., AB01). For example, AB01-treated corn and soy can reduce leaf temperatures as compared to an untreated plant.

Another method to measure increased transpiration due to hydraulic enhancement can be a screen called ex vivo hydraulic enhancement (xVHS). xVHS can be a simple assay that can be used to quantitate the increased transpiration in plant seedlings upon application of a compound, salt, solvate, or formulation disclosed herein (e.g., AB01) that can induce hydraulic enhancement.

Another effect of hydraulic enhancement on plant physiology can be the lowering of the permanent wilting point. The permanent wilting point (PWP) can be defined as the minimal amount of soil moisture (typically measured as volumetric water content) required for a plant not to wilt. In some cases, a plant will wilt and will not be able to recover turgidity below this threshold (e.g., in dryer soil). The value of a PWP can be highly dependent on crop species and/or soil type.

Hydraulic enhancement can lower the PWP of treated plants. PWP can be measured by recording the volumetric water content of soil over time and monitoring the wilting of a plant. In an example where irrigation is stopped, the monitored plants can transpire the available water and then reach the PWP. The reduction of PWP can have increase plant yield. In a field, the water available to a plant (the 'plant available water') can be defined as the difference between the soil moisture at field capacity (the amount of water in a field after excess water has drained away) and the soil moisture at PWP. Thus, decreasing the PWP can increase the plant available water. Hydraulic enhanced plants can access more of the total water in the soil. The increase in plant available water can also result in increased yield of the plant.

The combination of the physiological outcomes of hydraulic enhancement—higher transpiration and lower PWP—can drive yield increases in treated plants over untreated plants. Increased stomatal conductance can allow a plant to take in and fix more $CO_2$, which can lead to higher levels of photosynthate for grain fill. A lower PWP can allow a rapidly transpiring plant to continue transpiration where untreated (e.g., non-hydraulic enhanced) plants would encounter water limitation stress.

There can be secondary physiological effects of hydraulic enhancement in plants. For example, one secondary physiological effect of hydraulic enhancement can be the increased hydration of plant tissues, such as during periods of drought stress.

Another physiological outcome of hydraulic enhancement can be the more efficient fluid flow in the xylem of the plant. The negative pressure of the xylem water column (e.g., caused by the evapotranspirative force pulling water through the plant) can result in the formation of vapor bubbles, which can cause cavitation and turbulent flow. These cavitation events can also result in an embolism in the xylem, which can impede the flow of water up the plant ability of the plant to effectively transpire. Hydraulic enhanced plants can also show reduced rates of cavitation. Cavitation in the xylem can be measured by ultrasonic acoustic emission (UAE). For example, the formation and/or destruction of vapor bubbles can create ultrasonic events that can be recorded using a microphone attached to the xylem. The rate of UAE events can be proportional to the amount of cavitation in the xylem.

The compounds, salts, solvates, and formulations disclosed herein may be used in agriculture. The compounds, salts, solvates, and formulations may be used to promote plant growth. The compounds, salts, solvates, and formulations disclosed herein may be used for enhancing shoot stability in plants. The compounds, salts, solvates, and formulations may be used for increasing transport capacity in plants. The compounds, salts, solvates, and formulations may be used for increasing drought tolerance of a plant.

Further disclosed herein are methods of improving agriculture comprising applying a formulation comprising a compound, salt, solvate, or formulation to a plant, thereby improving agriculture. Improving agriculture may comprise promoting plant growth. Improving agriculture may comprise enhancing shoot stability in plants. Improving agriculture may comprise increasing transport capacity in plants. Improving agriculture may comprise increasing drought tolerance. Improving agriculture may comprise reducing an application of one or more pesticides. Improving agriculture may comprise terminating application of one or more pesticides. Improving agriculture may comprise reducing watering amounts applied to the plants. Improving agriculture may comprise reducing watering frequency to the plants. Improving agriculture may comprise controlling phytopathogenic fungi. Improving agriculture may comprise controlling unwanted plant growth. Improving agriculture may comprise controlling unwanted insect or mite infestation. Improving agriculture may comprise regulating growth of the plant. Improving agriculture may comprise promoting or stimulating activity in one or more fungi.

Further disclosed herein are methods of controlling phytopathogenic fungi and/or unwanted plant growth and/or unwanted insect or mite infestation and/or for regulating the growth of plants. The methods may comprise use of a formulation comprising a compound, salt, solvate, or formulation disclosed herein to act on the respective pests, their habitat or the plants to be protected from the respective pest, to the soil and/or to unwanted plants and/or the crop plants and/or their habitat.

The compounds, salts, solvates, may increase plant growth by at least about 5%. The compounds, salts, solvates, may increase plant growth by at least about 10%. The compounds, salts, solvates, may increase plant growth by at least about 15%. The compounds, salts, solvates, may increase plant growth by at least about 20%. The compounds, salts, solvates, may increase plant growth by at least about 25%. The compounds, salts, solvates, may increase plant growth by at least about 30%. The compounds, salts, solvates, may increase plant growth by at least about 50%. The compounds, salts, solvates, may increase plant growth by at least about 60%, 70%, 80%, 90%, 95%, 100% or more.

The compounds, salts, solvates, may increase plant growth by at least about 1.5, 2, 3, 4, 5, 6, 7, 8, 9, 10, 11, 12, 13, 14, 15, 16, 17, 18, 19, 20, 25, 30, 40, 50-fold or more. The compounds, salts, solvates, may increase plant growth by at least about 1.5-fold or more. The compounds, salts, solvates, may increase plant growth by at least about 2-fold or more. The compounds, salts, solvates, may increase plant growth by at least about 3-fold or more. The compounds, salts, solvates, may increase plant growth by at least about 5-fold or more. The compounds, salts, solvates, may increase plant growth by at least about 10-fold or more. Plant growth may comprise secondary plant growth.

The compounds, salts, solvates, may enhance shoot growth by at least about 5%. The compounds, salts, solvates, may enhance shoot growth by at least about 10%. The compounds, salts, solvates, may enhance shoot growth by at least about 15%. The compounds, salts, solvates, may enhance shoot growth by at least about 20%. The compounds, salts, solvates, may enhance shoot growth by at least about 25%. The compounds, salts, solvates, may enhance shoot growth by at least about 30%. The compounds, salts, solvates, may enhance shoot growth by at least about 50%. The compounds, salts, solvates, may enhance shoot growth by at least about 60%, 70%, 80%, 90%, 95%, 100% or more. The compounds, salts, solvates, may enhance shoot growth by at least about 1.5, 2, 3, 4, 5, 6, 7, 8, 9, 10, 11, 12, 13, 14, 15, 16, 17, 18, 19, 20, 25, 30, 40, 50-fold or more.

The compounds, salts, solvates, may enhance shoot growth by at least about 1.5-fold or more. The compounds, salts, solvates, may enhance shoot growth by at least about 2-fold or more. The compounds, salts, solvates, may enhance shoot growth by at least about 3-fold or more. The compounds, salts, solvates, may enhance shoot growth by at least about 5-fold or more. The compounds, salts, solvates, may enhance shoot growth by at least about 10-fold or more.

The compounds, salts, solvates, may increase transport capacity in plants by at least about 5%. The compounds, salts, solvates, may increase transport capacity in plants by at least about 10%. The compounds, salts, solvates, may increase transport capacity in plants by at least about 15%. The compounds, salts, solvates, may increase transport capacity in plants by at least about 20%. The compounds, salts, solvates, may increase transport capacity in plants by at least about 25%. The compounds, salts, solvates, may increase transport capacity in plants by at least about 30%. The compounds, salts, solvates, may increase transport capacity in plants by at least about 50%. The compounds, salts, solvates, may increase transport capacity in plants by at least about 60%, 70%, 80%, 90%, 95%, 100% or more.

The compounds, salts, solvates, may increase transport capacity in plants by at least about 1.5, 2, 3, 4, 5, 6, 7, 8, 9, 10, 11, 12, 13, 14, 15, 16, 17, 18, 19, 20, 25, 30, 40, 50-fold or more. The compounds, salts, solvates, may increase transport capacity in plants by at least about 1.5-fold or more. The compounds, salts, solvates, may increase transport capacity in plants by at least about 2-fold or more. The compounds, salts, solvates, may increase transport capacity in plants by at least about 3-fold or more. The compounds, salts, solvates, may increase transport capacity in plants by at least about 5-fold or more. The compounds, salts, solvates, may increase transport capacity in plants by at least about 10-fold or more.

The compounds, salts, solvates, may increase drought tolerance in plants by at least about 5%. The compounds, salts, solvates, may increase drought tolerance in plants by at least about 10%. The compounds, salts, solvates, may increase drought tolerance in plants by at least about 15%. The compounds, salts, solvates, may increase drought tolerance in plants by at least about 20%. The compounds, salts, solvates, may increase drought tolerance in plants by at least about 25%. The compounds, salts, solvates, may increase drought tolerance in plants by at least about 30%. The compounds, salts, solvates, may increase drought tolerance in plants by at least about 50%. The compounds, salts, solvates, may increase drought tolerance in plants by at least about 60%, 70%, 80%, 90%, 95%, 100% or more.

The compounds, salts, solvates, may increase drought tolerance in plants by at least about 1.5, 2, 3, 4, 5, 6, 7, 8, 9, 10, 11, 12, 13, 14, 15, 16, 17, 18, 19, 20, 25, 30, 40, 50-fold or more. The compounds, salts, solvates, may increase drought tolerance in plants by at least about 1.5-fold or more. The compounds, salts, solvates, may increase drought tolerance in plants by at least about 2-fold or more. The compounds, salts, solvates, may increase drought tolerance in plants by at least about 3-fold or more. The compounds, salts, solvates, may increase drought tolerance in plants by at least about 5-fold or more. The compounds, salts, solvates, may increase drought tolerance in plants by at least about 10-fold or more.

The compounds, salts, solvates, may reduce the application of one or more pesticides. Reducing the application of one or more pesticides may comprise reducing an amount of the one or more pesticides that are applied to the plant. The amount of the one or more pesticides applied to the plant may be reduced by at least about 1%, 5%, 10%, 15%, 20%, 25%, 30%, 35%, 40%, 50%, 60%, 70%, 80%, 90%, 95%, or 100%. The amount of the one or more pesticides applied to the plant may be reduced by at least about 10%. The amount of the one or more pesticides applied to the plant may be reduced by at least about 20%. The amount of the one or more pesticides applied to the plant may be reduced by at least about 30%. The amount of the one or more pesticides applied to the plant may be reduced by at least about 50%.

Alternatively, or additionally, reducing the application of the one or more pesticides may comprise reducing a frequency of which the one or more pesticides are applied to the plant. The frequency of which the one or more pesticides are applied to the plant may be reduced by at least about 1%, 5%, 10%, 15%, 20%, 25%, 30%, 35%, 40%, 50%, 60%, 70%, 80%, 90%, 95%, or 100%. The frequency of which the one or more pesticides are applied to the plant may be reduced by at least about 10%. The frequency of which the one or more pesticides are applied to the plant may be reduced by at least about 20%. The frequency of which the one or more pesticides are applied to the plant may be reduced by at least about 30%. The frequency of which the one or more pesticides are applied to the plant may be reduced by at least about 40%. The frequency of which the one or more pesticides are applied to the plant may be reduced by at least about 50%.

Use of the compounds, salts, solvates, may allow a reduction in the amount of water applied to the plants. The amount of the water applied to the plant may be reduced by at least about 1%, 5%, 10%, 15%, 20%, 25%, 30%, 35%, 40%, 50%, 60%, 70%, 80%, 90%, 95%, or 100%. The amount of the water applied to the plant may be reduced by at least about 10%. The amount of the water applied to the plant may be reduced by at least about 20%. The amount of the water applied to the plant may be reduced by at least about 30%. The amount of the water applied to the plant may be reduced by at least about 50%.

Use of the compounds, salts, solvates, may allow a reduction in the frequency of which the water is applied to the plant. The frequency of which the water is applied to the plant may be reduced by at least about 1%, 5%, 10%, 15%, 20%, 25%, 30%, 35%, 40%, 50%, 60%, 70%, 80%, 90%, 95%, or 100%. The frequency of which the water is applied to the plant may be reduced by at least about 10%. The frequency of which the water is applied to the plant may be reduced by at least about 20%. The frequency of which the water is applied to the plant may be reduced by at least about 30%. The frequency of which the water is applied to the plant may be reduced by at least about 40%. The frequency of which the water is applied to the plant may be reduced by at least about 50%.

The compound, salt, solvate, formulation disclosed herein may be used to control phytopathogenic fungi. Improving agriculture may comprise controlling unwanted plant growth. Controlling unwanted plant growth may comprise stimulating germination activity of the unwanted plant. The unwanted plant may be a parasitic plant. The unwanted plant may be a root parasitic plant. Examples of parasitic plants can include, but are not limited to, witchweeds (*Striga* spp.), broomrapes (Orobanche spp, Phelipanche spp), Alectra, dodders, and mistletoes. The unwanted plant may belong to the family Orobanchaceae. The unwanted plant may be witchweed. The unwanted plant may be Orobanche spp. The compound, salt, solvate, or formulation may be applied directly to the unwanted plant. The compound, salt, solvate, or formulation may be applied indirectly to the unwanted plant.

The compound, salt, solvate, or formulation disclosed herein may be used to control unwanted insect or mite infestation. Examples of insects and mites can include, but are not limited to spiders, gnats, mealybugs, whiteflies, predator mites, spider mites and aphids.

The compound, salt, solvate, or formulation disclosed herein may be used to regulate growth of the plant. Regulating plant growth may comprise regulating plant breeding. Regulating plant growth may comprise inhibiting shoot branching. Regulating plant growth may comprise regulating one or more plant products. Regulating plant growth may comprise inhibiting root development.

The compound, salt, solvate, or formulation disclosed herein may be used to promote or stimulate activity in fungi. The compound, salt, solvate, or formulation may stimulate hyphal branching activity of one or more fungi. The compound, salt, solvate, or formulation may induce spore germination of one or more fungi. The one or more fungi may be arbuscular mycorrhizal (AM) fungi.

Further disclosed herein are methods of preserving or extending the life of a plant. Generally, the method may comprise contacting the plant with a compound, salt, solvate, or formulation disclosed herein. The compound, salt, solvate, or formulation for use in preserving or extending the life of a plant may be produced by any of the methods disclosed herein. The compound, salt, solvate, or formulation may be produced by chemical synthesis. For example, the compound, salt, solvate, or formulation can be produced by conducting a condensation reaction on a sesquiterpene lactone, salt, solvate, polymorph, stereoisomer, isomer or derivative thereof. The compound, salt, solvate, or formulation may be produced by conducting a hydroxymethylation on a sesquiterpene lactone, salt, solvate, polymorph, stereoisomer, isomer or derivative thereof. The compound, salt, solvate, or formulation may be produced by (a) conducting a hydroxymethylation on a sesquiterpene lactone, salt, solvate, polymorph, stereoisomer, isomer or derivative thereof to produce a first product; and (b) conducting an alkylation reaction on the first product. Alternatively, the compound, salt, solvate, or formulation can be produced by biological synthesis. Biological synthesis may comprise the use of one or more cells, genes, or vectors disclosed herein.

The compound, salt, solvate, or formulation may be used to preserve or extend the life of a cut plant. The cut plant may be a flower. The cut plant may be a tree. The cut plant may be bush or shrub. The cut plant may be a vegetable. The compound, salt, solvate, or formulation may be used to preserve or extend the life of an uncut plant. The uncut plant may be a flower. The uncut plant may be a tree. The uncut plant may be bush or shrub. The uncut plant may be a vegetable. The compound, salt, solvate, or formulation may be used to preserve or extend the life of a potted plant. The potted plant may be a flower. The potted plant may be a tree. The potted plant may be bush or shrub. The potted plant may be a vegetable.

The compound, salt, solvate, or formulation may be used to preserve or extend the life of a flower. Examples of flowers can include, but are not limited to, lilies, daisies, roses, marigolds, Angel's trumpet, phlox, vinca, snapdragons, toadflax, orchids, ferns, black-eyed Susans, blood flowers, blue lobelias, morning glories, poppies, calendulas, geraniums, impatiens, lantanas, larkspurs, calla lilies, hyacinths, azaleas, pointsettias, and begonias.

The compound, salt, solvate, or formulation may be used to preserve or extend the life of a bush or shrub. Examples of bushes and shrubs can include, but are not limited to, forsynthia, fuchsia, hibiscus, currant, lilac, rose, hydrangea, willow, magnolia, thyme, snowberry, dogwood and holly.

The compound, salt, solvate, or formulation may be used to preserve or extend the life of a tree. Examples of trees can include, but are not limited to, cypress, poinsettia, palm, fir, pine, spruce, cedar, oak, mulberry, chestnut, hawthorn, poplar, and maple. The tree may be a fir tree. The fir tree may be a Douglas, Balsam or Fraser fir tree. The tree may be a pine tree. The pine tree may be a Scotch or White pine tree. The tree may be a spruce tree. The spruce tree may be a White, Norway or Blue spruce tree. The tree may be a cedar tree. The cedar tree may be a *Deodara* or Eastern red cedar. The tree may be a cypress tree. The cypress tree may be an Arizona or Leland cypress tree.

The plant may be contacted with a compound, salt, solvate, or formulation disclosed herein, thereby extending or preserving the life of the plant. Contacting the plant with the compound, salt, solvate, or formulation may comprise administering the compound, salt, solvate, or formulation as a spray. Contacting the plant with the compound, salt, solvate, or formulation may comprise adding the plant growth material to the irrigation water of the plant. Contacting the plant with the compound, salt, solvate, or formulation may comprise applying the compound, salt, solvate, or formulation to the habitat of the plant. Contacting the plant with the compound, salt, solvate, or formulation may comprise adding the compound, salt, solvate, or formulation to a plant container (e.g., vase) and placing the plant in the plant container. Contacting the plant with the compound, salt, solvate, or formulation may comprise adding the compound, salt, solvate, or formulation to soil.

The life of the plant may be extended by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The life of the plant may be extended by at least about 20% as compared to an untreated plant. The life of the plant may be extended by at least about 30% as compared to an untreated plant. The life of the plant may be extended by at least about 40% as compared to an untreated plant. The life of the plant may be extended by at least about 50% as compared to an untreated plant. The life of the plant may be extended by at least about 55% as compared to an untreated plant. The life of the plant may be extended by at least about 60% as compared to an untreated plant. The life of the plant may be extended by at least about 65% as compared to an untreated plant. The life of the plant may be extended by at least about 70% as compared to an untreated plant. The life of the plant may be extended by at least about 75% as compared to an untreated plant. The life of the plant may be extended by at least about 80% as compared to an untreated plant. The life of the plant can be determined by measuring the growth time between initial planting of a seed of the plant to the death of the plant.

The life of the plant may be extended by at least about 6, 12, 24, 30, 36, 42, 48, 54, 60, 66, 72, 78, 84, 90, 96, 102, 108, 114, or 120 hours as compared to an untreated plant. The life of the plant may be extended by at least about 24 hours as compared to an untreated plant. The life of the plant may be extended by at least about 36 hours as compared to an untreated plant. The life of the plant may be extended by at least about 48 hours as compared to an untreated plant. The life of the plant may be extended by at least about 72 hours as compared to an untreated plant. The life of the plant may be extended by at least about 96 hours as compared to an untreated plant.

The life of the plant may be extended by at least about 1, 1.5, 2, 2.5, 3, 3.5, 4, 4.5, 5, 5.5, 6, 6.5, or 7 days as compared to an untreated plant. The life of the plant may be extended by at least about 8, 9, 10, 11, 12, 13, 14, 15, 16, 17, 18, 19, or 20 days as compared to an untreated plant. The life of the plant may be extended by at least about 1 day as compared to an untreated plant. The life of the plant may be extended by at least about 2 days as compared to an untreated plant. The life of the plant may be extended by at least about 2.5 days as compared to an untreated plant. The life of the plant may be extended by at least about 3 days as compared to an untreated plant. The life of the plant may be extended by at least about 3.5 days as compared to an untreated plant. The life of the plant may be extended by at least about 4 days as compared to an untreated plant. The life of the plant may be extended by at least about 4.5 days as compared to an untreated plant.

The life of the plant may be extended by at least about 1, 1.5, 2, 2.5, 3, 3.5, 4, 4.5, 5, 5.5, 6, 6.5, or 7 weeks as compared to an untreated plant. The life of the plant may be extended by at least about 8, 9, 10, 11, 12, 13, 14, 15, 16, 17, 18, 19, or 20 weeks as compared to an untreated plant. The life of the plant may be extended by at least about 1, 1.5, 2, 2.5, 3, 3.5, 4, 4.5, 5, 5.5, 6, 6.5, or 7 months as compared to an untreated plant. The life of the plant may be extended by at least about 8, 9, 10, 11, 12, 13, 14, 15, 16, 17, 18, 19, or 20 months as compared to an untreated plant.

Preserving or extending the life of the plant may comprise reducing wilting of the plant. Reducing wilting of the plant may comprise reducing flower or leaf rolling of the plant. The wilting of the plant may be reduced by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The wilting of the plant may be reduced by at least about 10% as compared to an untreated plant. The wilting of the plant may be reduced by at least about 30% as compared to an untreated plant. The wilting of the plant may be reduced by at least about 50% as compared to an untreated plant. The wilting of the plant may be reduced by at least about 70% as compared to an untreated plant. The wilting of the plant may be reduced by at least about 80% as compared to an untreated plant.

A sign of plant stress may include wilting of the plant. For example, stressed plants may have rolled leaves or petals. The plant growth materials disclosed herein may promote the life of the plant by reducing the wilting of the plant. Reducing the wilting of the plant may comprise delaying the wilting of the plant as compared to an untreated plant. For example, an untreated cut plant may show signs of wilting within 36 hours of being cut, however, a cut plant treated with a plant growth material may have delayed wilting. The wilting of the plant may be delayed by at least about 2, 3, 4, 5, 6, 7, 8, 9, 10, 11, 12, 13, 14, 15, 16, 17, 18, 19, 20, 21, 22, 23, or 24 hours as compared to an untreated plant. The wilting of the plant may be delayed by at least about 12 hours as compared to an untreated plant. The wilting of the plant may be delayed by at least about 24 hours as compared to an untreated plant. The wilting of the plant may be delayed by at least about 36 hours as compared to an untreated plant. The wilting of the plant may be delayed by at least about 48 hours as compared to an untreated plant.

An additional sign of plant stress may include reduced turgidity. Turgidity may refer to pressure caused by the osmotic flow of water from an area of low solute concentration outside of the cell into the cell cell's vacuole. Turgidity may be used by plants to maintain rigidity. Often, healthy plants are turgid, whereas, unhealthy plants are less turgid. Preserving or extending the life of the plant may comprise prolonging or maintaining the turgidity of the plant. The turgidity of the plant may be greater than the turgidity of an untreated plant. The turgidity of the plant may be at least about 1%, 5%, 10%, 15%, 20%, 25%, 30%, 35%, 40%, 45%, 50%, 55%, 60%, 65%, 70%, 75%, 80%, 85%, 90%, 95%, or 97% greater than the turgidity of an untreated plant. The turgidity of the plant may be at least about 10% greater than the turgidity of an untreated plant. The turgidity of the plant may be at least about 15% greater than the turgidity of an untreated plant. The turgidity of the plant may be at least about 25% greater than the turgidity of an untreated plant. The turgidity of the plant may be at least about 35% greater than the turgidity of an untreated plant. The turgidity of the plant may be at least about 45% greater than the turgidity of an untreated plant. The turgidity of the plant may be at least about 60% greater than the turgidity of an untreated plant. The turgidity of the plant may be at least about 75% greater than the turgidity of an untreated plant.

A stressed plant may also show a reduction in the turgid state. The turgid state may refer to a period of time in which the plant maintains its rigidity. The rigidity of the plant may refer to the rigidity of the stem of the plant. For example, as cut plants die, the stem of the plant may be less rigid, thereby causing the cut plant to fall over or bend. A stressed plant may be unable to hold itself upright. Preserving or extending the life of the plant may comprise prolonging the turgid state of the plant. The turgid state of the plant may be increased by at least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to an untreated plant. The turgid state of the plant may be increased by at least about 20% as compared to an untreated plant. The turgid state of the plant may be increased by at least about 30% as compared to an untreated plant. The turgid state of the plant may be increased by at least about 40% as compared to an untreated plant. The turgid state of the plant may be increased by at least about 50% as compared to an untreated plant.

The turgid state of the plant may be increased by at least about 2, 3, 4, 5, 6, 7, 8, 9, 10, 11, 12, 13, 14, 15, 16, 17, 18, 19, 20, 21, 22, 23, or 24 hours as compared to an untreated plant. The turgid state of the plant may be increased by at least about 6 hours as compared to an untreated plant. The turgid state of the plant may be increased by at least about 12 hours as compared to an untreated plant. The turgid state of the plant may be increased by at least about 24 hours as compared to an untreated plant.

A stressed plant may lose leaves or petals. Contacting a plant with a plant growth material may reduce or delay the loss of one or more petals or leaves of the plant. For example, an untreated plant may lose 50% of its leaves or petals, whereas a treated plant may lose 10-25% of its leaves or petals. The loss of the one or more petals of the plant may be reduced by least about 1%, 5%, 10%, 15%, 20%, 25%, 30%, 35%, 40%, 45%, 50%, 55%, 60%, 65%, 70%, 75%, 80%, 85%, 90%, 95%, or 97% as compared to the loss of the one or more petals of an untreated plant. The loss of the one or more petals of the plant may be reduced by least about 10% as compared to the loss of the one or more petals of an untreated plant. The loss of the one or more petals of the plant may be reduced by least about 20% as compared to the loss of the one or more petals of an untreated plant. The loss of the one or more petals of the plant may be reduced by least about 35% as compared to the loss of the one or more petals of an untreated plant. The loss of the one or more petals of the plant may be reduced by least about 50% as compared to the loss of the one or more petals of an untreated plant. The loss of the one or more petals of the plant may be reduced by least about 60% as compared to the loss of the one or more petals of an untreated plant. The loss of the one or more petals of the plant may be reduced by least about 70% as compared to the loss of the one or more petals of an untreated plant.

The loss of the one or more petals of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of one or more petals of an untreated plant. The loss of the one or more petals of the plant may be delayed by at least about 25, 30, 35, 40, 45, 50, 55, 60, 65, 70, 75, 80, 85, 90, 95 or 100 hours as compared to the loss of one or more petals of an untreated plant. The loss of the one or more petals of the plant may be delayed by at least about 6 hours as compared to the loss of one or more petals of an untreated plant. The loss of the one or more petals of the plant may be delayed by at least about 12 hours as compared to the loss of one or more petals of an untreated plant. The loss of the one or more petals of the plant may be delayed by at least about 18 hours as compared to the loss of one or more petals of an untreated plant. The loss of the one or more petals of the plant may be delayed by at least about 36 hours as compared to the loss of one or more petals of an untreated plant. The loss of the one or more petals of the plant may be delayed by at least about 48 hours as compared to the loss of one or more petals of an untreated plant. The loss of the one or more petals of the plant may be delayed by at least about 60 hours as compared to the loss of one or more petals of an untreated plant. The loss of the one or more petals of the plant may be delayed by at least about 72 hours as compared to the loss of one or more petals of an untreated plant. The loss of the one or more petals of the plant may be delayed by at least about 96 hours as compared to the loss of one or more petals of an untreated plant.

A stressed plant may show signs of discoloration. The stressed plant may appear brownish. Alernatively, or additionally, the stressed plant shows a reduction in the appearance of green leaves. The chlorohyll content of the stressed plant may also be reduced. Preserving or extending the life of the plant may comprise maintaining the chlorophyll content of the plant. For example, a reduction in the chlorophyll content of an untreated plant may appear within 48 hours of being cut. However, a reduction in the chlorophyll content of a treated plant may appear after 60 hours of being cut. The chlorophyll content of the plant may be maintained for at least about 2, 3, 4, 5, 6, 7, 8, 9, 10, 11, 12, 13, 14, 15, 16, 17, 18, 19, 20, 21, 22, 23, or 24 hours. The chlorophyll content of the plant may be maintained for at least about 6 hours. The chlorophyll content of the plant may be maintained for at least about 12 hours. The chlorophyll content of the plant may be maintained for at least about 24 hours.

Preserving or extending the life of the plant may comprise reducing or delaying the loss of the chlorophyll content of the plant. The chlorophyll content of the plant may be greater than the chlorophyll content of an untreated plant. The chlorophyll content of the plant may be at least about 1%, 5%, 10%, 15%, 20%, 25%, 30%, 35%, 40%, 45%, or 50% greater than the content of an untreated plant. The chlorophyll content of the plant may be at least about 55%, 60%, 65%, 70%, 75%, 80%, 85%, 90%, 95% or 97% greater than the content of an untreated plant. The chlorophyll content of the plant may be at least about 20% greater than the content of an untreated plant. The chlorophyll content of the plant may be at least about 30% greater than the content of an untreated plant. The chlorophyll content of the plant may be at least about 40% greater than the content of an untreated plant. The chlorophyll content of the plant may be at least about 50% greater than the content of an untreated plant. The chlorophyll content of the plant may be at least about 60% greater than the content of an untreated plant. The chlorophyll content of the plant may be at least about 1.5, 2, 2.5, 3, 3.5, 4, 4.5, 5, 5.5, 6, 6.5, 7, 8, 9, or 10-fold greater than the content of an untreated plant. The chlorophyll content of the plant may be at least about 11, 12, 13, 14, 15, 16, 17, 18, 19, 20, 25, 30, 35, 40, 45, 50, 55, 60, 65, 70, 75, 80, 85, 90, 95 or 100-fold greater than the content of an untreated plant. The chlorophyll content of the plant may be at least about 2-fold greater than the content of an untreated plant. The chlorophyll content of the plant may be at least about 3-fold greater than the content of an untreated plant. The chlorophyll content of the plant may be at least about 4-fold greater than the content of an untreated plant. The chlorophyll content of the plant may be at least about 5-fold greater than the content of an untreated plant. The chlorophyll content of the plant may be at least about 10-fold greater than the content of an untreated plant.

The loss of the chlorophyll content of the plant may be delayed by at least about 2, 3, 4, 5, 6, 7, 8, 9, 10, 11, 12, 13, 14, 15, 16, 17, 18, 19, 20, 21, 22, 23, or 24 hours as compared to the loss of the chlorophyll content of an untreated plant. The loss of the chlorophyll content of the plant may be delayed by at least about 30, 35, 40, 45, 50, 55, 60, 65, 70, 75, 80, 85, 90, 95, or 100 hours as compared to the loss of the chlorophyll content of an untreated plant. The loss of the chlorophyll content of the plant may be delayed by at least about 6 hours as compared to the loss of the chlorophyll content of an untreated plant. The loss of the chlorophyll content of the plant may be delayed by at least about 12 hours as compared to the loss of the chlorophyll content of an untreated plant. The loss of the chlorophyll content of the plant may be delayed by at least about 24 hours as compared to the loss of the chlorophyll content of an untreated plant. The loss of the chlorophyll content of the plant may be delayed by at least about 36 hours as compared to the loss of the chlorophyll content of an untreated plant. The loss of the chlorophyll content of the plant may be delayed by at least about 48 hours as compared to the loss of the chlorophyll content of an untreated plant. The loss of the chlorophyll content of the plant may be delayed by at least about 60 hours as compared to the loss of the chlorophyll content of an untreated plant. The loss of the chlorophyll content of the plant may be delayed by at least about 72 hours as compared to the loss of the chlorophyll content of an untreated plant.

The loss of the chlorophyll content of the plant may be less than the loss of the chlorophyll content of an untreated plant. The loss of the chlorophyll content of the plant may be at least about 1%, 5%, 10%, 15%, 20%, 25%, 30%, 35%, 40%, 45%, 50%, 55%, or 60% less than the loss of the chlorophyll content of an untreated plant. The loss of the chlorophyll content of the plant may be at least about 65%, 70%, 72%, 75%, 77%, 80%, 85%, 90%, 92%, 95%, or 97% less than the loss of the chlorophyll content of an untreated plant. The loss of the chlorophyll content of the plant may be at least about 5% less than the loss of the chlorophyll content of an untreated plant. The loss of the chlorophyll content of the plant may be at least about 10% less than the loss of the chlorophyll content of an untreated plant. The loss of the chlorophyll content of the plant may be at least about 20% less than the loss of the chlorophyll content of an untreated plant. The loss of the chlorophyll content of the plant may be at least about 30% less than the loss of the chlorophyll content of an untreated plant. The loss of the chlorophyll content of the plant may be at least about 40% less than the loss of the chlorophyll content of an untreated plant. The loss of the chlorophyll content of the plant may be at least about 50% less than the loss of the chlorophyll content of an untreated plant. The loss of the chlorophyll content of the plant may be at least about 60% less than the loss of the chlorophyll content of an untreated plant.

The loss of the chlorophyll content of the plant may be at least about 1.5, 2, 2.5, 3, 3.5, 4, 4.5, 5, 5.5, 6, 6.5, 7, 7.5, 8, 8.5, 9, 9.5, or 10-fold less than the loss of the chlorophyll content of an untreated plant. The loss of the chlorophyll content of the plant may be at least about 11, 12, 13, 14, 15, 16, 17, 18, 19, 20, 25, 30, 35, 40, 45, 50, 55, 60, 65, 70, 75, 80, 85, 90, 95 or 100-fold less than the loss of the chlorophyll content of an untreated plant. The loss of the chlorophyll content of the plant may be at least about 2-fold less than the loss of the chlorophyll content of an untreated plant. The loss of the chlorophyll content of the plant may be at least about 3-fold less than the loss of the chlorophyll content of an untreated plant. The loss of the chlorophyll content of the plant may be at least about 5-fold less than the loss of the chlorophyll content of an untreated plant. The loss of the chlorophyll content of the plant may be at least about 10-fold less than the loss of the chlorophyll content of an untreated plant.

The compound, salt, solvate, or formulation may be applied directly to the plant. The compound, salt, solvate, or formulation may be applied to one or more parts of the plant. The one or more parts of the plant may comprise a terminal bud, flower, lateral bud, leaf blade, leaf axil, node, internode, petiole, primary root, lateral root, root hair, root cap, or a combination thereof. The formulations may be applied to the leaf blade of the plant. The formulations may be applied to the root of the plant.

Alternatively, or additionally, the compound, salt, solvate, or formulation can be applied indirectly to the plant. The formulation may be applied to an area around the plant. The area around the plant may comprise soil. The area around the plant may comprise an adjacent plant.

The compound, salt, solvate, or formulation may be applied to a plant that is susceptible to a parasitic weed. Examples of plants include, but are not limited to, corn, rice, sorghum, millets, and sugar cane. The plant may be corn. The plant may be tobacco. The plant may be rice.

The compound, salt, solvate, or formulation may be applied as a seed coating. The compound, salt, solvate, or formulation may be applied as a seed treatment. The compound, salt, solvate, or formulation may be applied as a seed dressing. The compound, salt, solvate, or formulation may be applied as a spray. The compound, salt, solvate, or formulation may be applies as a foliar spray. The compound, salt, solvate, or formulation may be applied as a powder.

The compound, salt, solvate, or formulation may be applied 1, 2, 3, 4, 5, 6, 7, 8, 9, 10 or more times a day. The compound, salt, solvate, or formulation may be applied once a day. The compound, salt, solvate, or formulation may be applied twice a day. The compound, salt, solvate, or formulation may be applied 1, 2, 3, 4, 5, 6, 7, 8, 9, 10 or more times per week. The compound, salt, solvate, or formulation may be applied once a week. The compound, salt, solvate, or formulation may be applied twice a week. The compound, salt, solvate, or formulation may be applied three times a week. The compound, salt, solvate, or formulation may be applied four times a week. The formulations may be applied 1, 2, 3, 4, 5, 6, 7, 8, 9, 10 or more times a month. The formulations may be applied once a month. The compound, salt, solvate, or formulation may be applied twice a month. The compound, salt, solvate, or formulation may be applied three times a month. The compound, salt, solvate, or formulation may be applied four times a month. The formulations may be applied ten times a month. The compound, salt, solvate, or formulation may be applied 15 times a month. The formulations may be applied 20 times a month.

In some embodiments, the measurement described herein can be made at a temperature of about 1, 2, 3, 4, 5, 6, 7, 8, 9, 10, 11, 12, 13, 14, 15, 16, 17, 18, 19, 20, 21, 22, 23, 24, 25, 6, 27, 28, 29, 30, 31, 32, 33, 34, 35, 36, 37, 38, 39, or 40° C.

EXAMPLES

Measurement of Transpiration Using a Porometer

Figure 2:
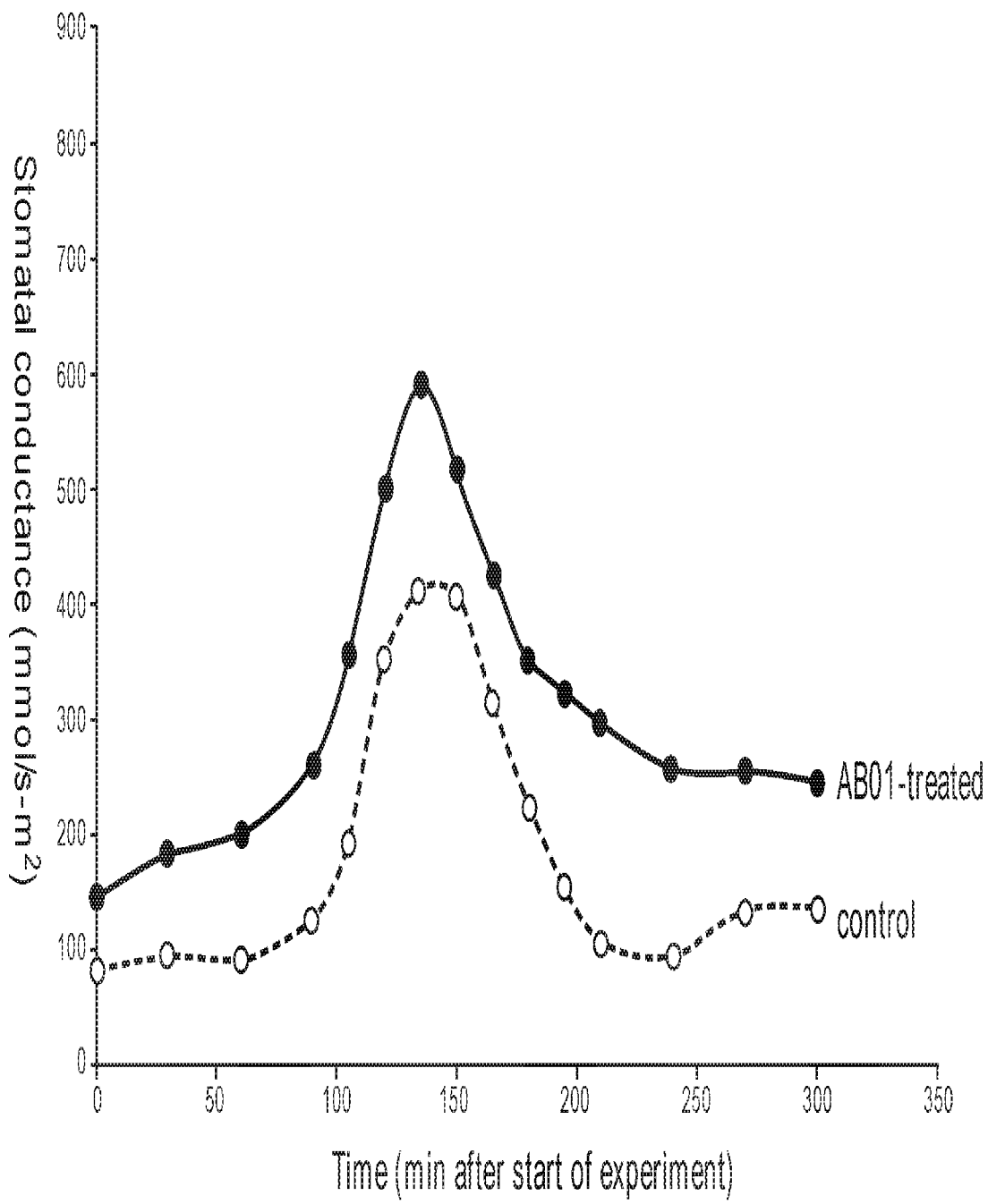
FIG. 2 shows increased transpiration in a hydraulic enhanced plant.

Transpiration was measured using a hand-held leaf porometer, a device that measures stomatal conductance via water vapor in a fixed chamber. The porometer was used to measure the difference in transpiration between two corn plants (hybrid Dekalb 68-05), one treated with AB01 and one that was untreated (FIG. 2). It was found that hydraulic enhancement via AB01 treatment resulted in increased transpiration at all points throughout a 12-hour daylight cycle.

Measurement of transpiration using an infrared camera

Figure 3:
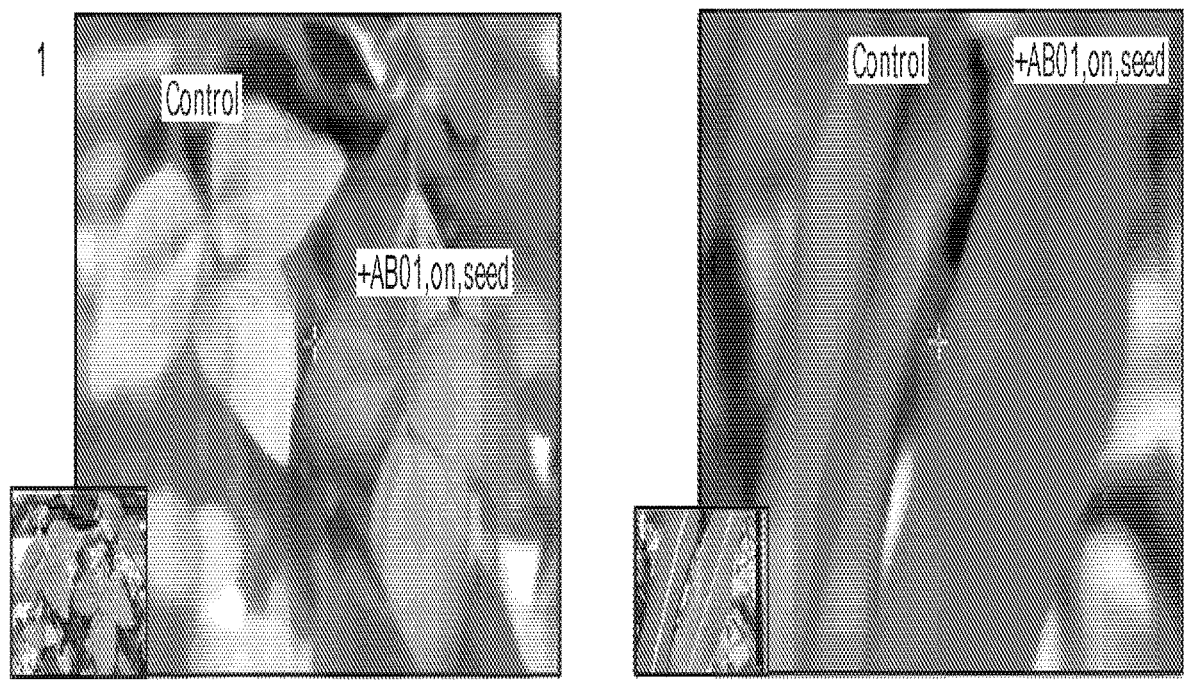
FIG. 3 shows hydraulic enhanced plants having lower leaf and canopy temperatures.

In this experiment, increased transpiration exhibited a lower canopy temperature because higher transpiration resulted in better evaporative cooling of the leaf and canopy structures. This phenomenon was demonstrated using an infrared camera to image plants that had been treated with AB01. It was found that AB01-treated corn and soy had leaf temperatures at least 1 degree cooler than untreated plants (FIG. 3).

Measurement of Transpiration Using xVHS Assay

Figure 4A:
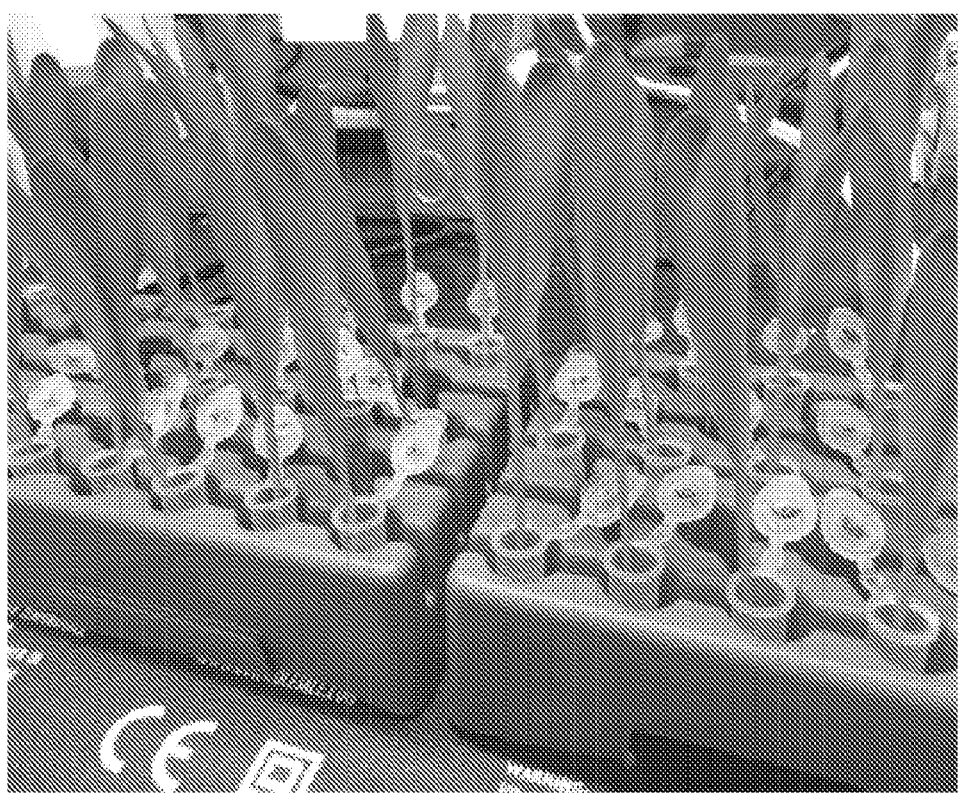
FIG. 4A shows the experimental setup of xVHS assay.
Figure 4B:
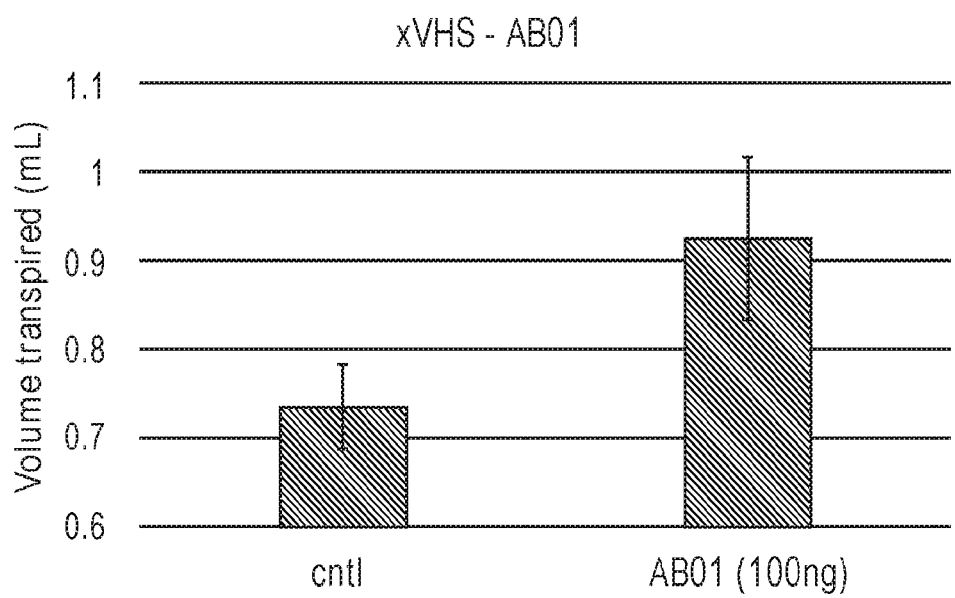
FIG. 4B shows increased transpiration in hydraulic enhanced (100 ng AB01-treated) plants.

In this experiment, xVHS was used to quantitate the increased transpiration in plant seedlings upon application of chemistry or other inputs that can induce hydraulic enhancement. In this assay with corn (Zea mays), seedlings were grown in defined potting soil (in this case, Sunshine Mix #4) for 2 weeks until they were approximately 15 to 20 centimeters tall. Seedlings were then cut at the base of the stem and placed in individual tubes with defined volume of water (FIG. 4A). Hydraulic enhancing chemistry (for example, AB01) was present in the defined volume of water at various concentrations. Excised seedlings were placed in a defined temperature and humidity environment under continuous illumination, and water use was measured after 12, 18, or 24 hours. Using this assay, chemistry or other inputs that induce hydraulic enhancement can be tested and discovered. Results from the xVHS assay on AB01 were shown in FIG. 4B. In this assay, 100 ng of AB01 in acetone was added to 2 week old corn seedlings and water use was monitored over 24 hours. Hydraulic enhancement via AB01 addition resulted in 20-30% increase in water use via transpiration.

Measurement of PWP

Figure 5:
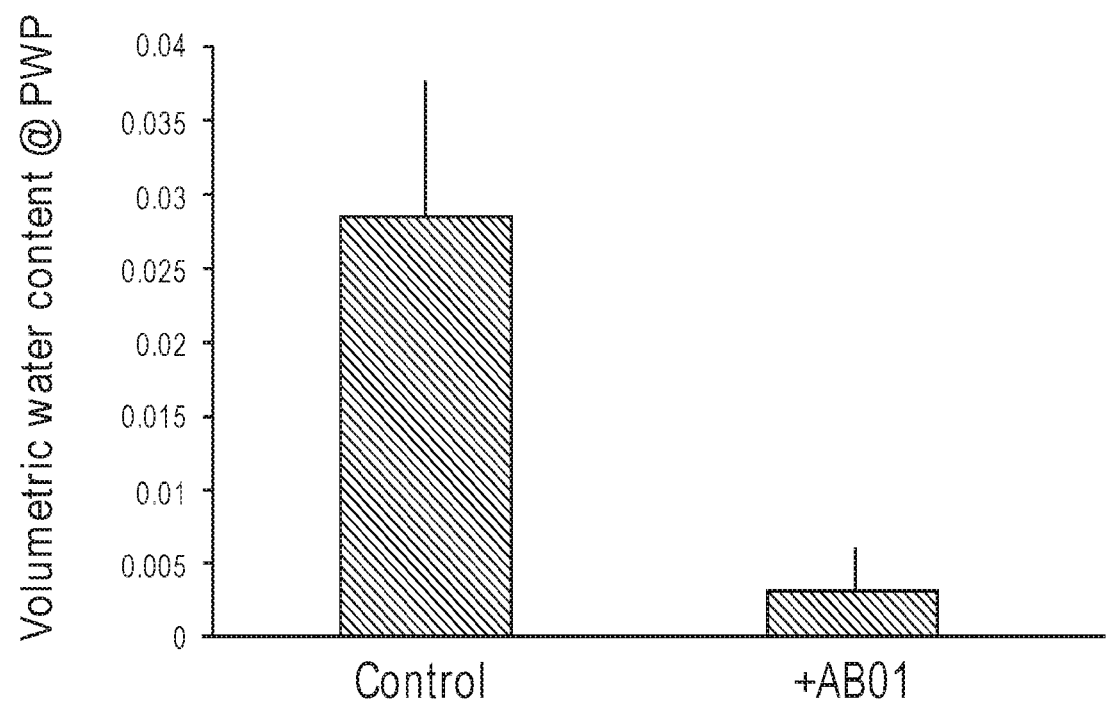
FIG. 5 shows depressed permanent wilting point in hydraulic enhanced (AB01-treated) plants.
Figure 6:
FIG. 6 shows improved silk tissue hydration in the hydraulic enhanced (75 μg/seed AB01-treated) plant (right) as compared to a control plant, left.
Figure 7:
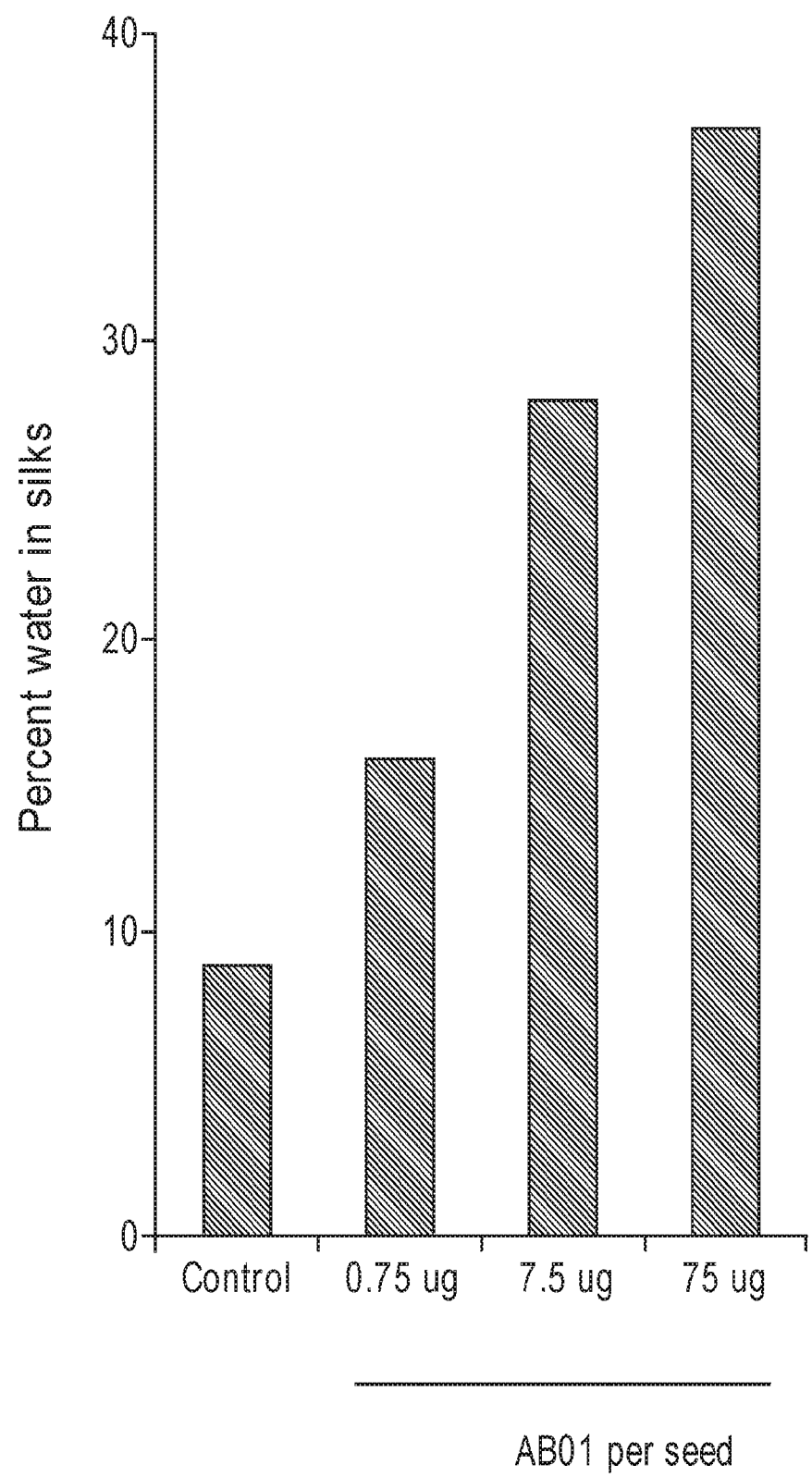

This experiment showed that hydraulic enhancement chemistry lowered the PWP of treated plants. PWP was measured by recording the volumetric water content of soil over time and monitoring the wilting of a given plant. The PWP of a set of untreated corn hybrid Dekalb 68-05 and a set of AB01-treated Dekalb 68-05 were measured. It was found that the PWP of the untreated corn was 0.027 ($m^3/m^3$), while the PWP of the AB01-treated corn was 0.003 ($m^3/m^3$) (FIG. 5). Measure yield of corn In one experiment, the hydration of silks in greenhouse-grown corn was measured. The relative hydration (water content) of silks can be used to determine of grain yield, where poorly hydrated silks result in poor pollen fertilization and kernel set. Corn (hybrid Dekalb 68-05) was grown with irrigation in the greenhouse. Plants were treated with varying doses of AB01 prior to tasselling as a seed treatment. Seven days after silking was complete, silks were photographed and then harvested by cutting at the tip of the ear. Differences in silk hydration were visible, with the highest treatment showing the highest hydration and the untreated control showing the lowest hydration (FIG. 6). Visual observations were verified by measuring the mass of the cut silks. The mass of silks increased with AB01 concentration applied (FIG. 7).

Measurement of Cavitation Rates

Figure 8:
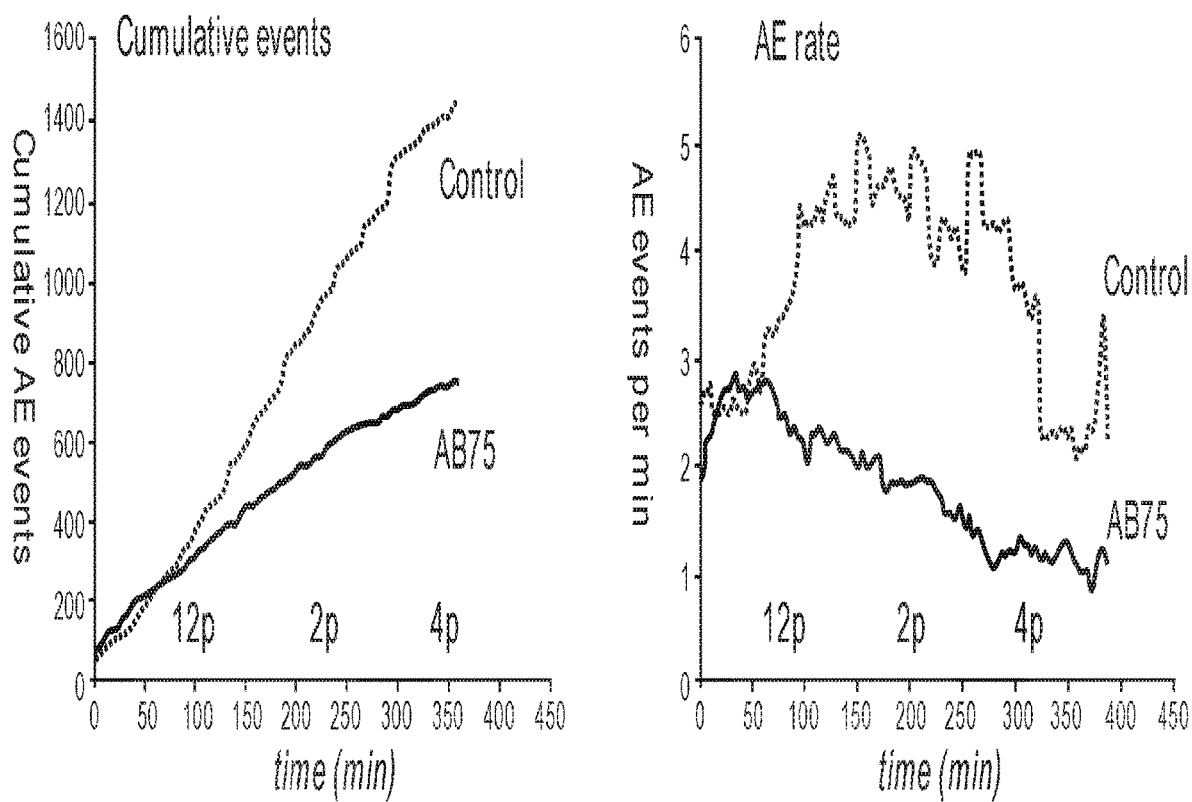

Another physiological outcome of hydraulic enhancement can be more efficient fluid flow in the xylem of the plant. In this experiment, it was shown that hydraulic enhanced plants reduced rates of cavitation. Cavitation in the xylem was measured by ultrasonic acoustic emission (UAE). The formation and destruction of vapor bubbles creating ultrasonic events was recorded using a microphone attached to the xylem. A Physical Acoustics USB-based system (1283 USB AE node, 18-bit A/D, 20 MHz) with 150 kHz resonant sensors (PK15I, 26 dB integrated preamplifiers) was used to measure UAE rates of untreated and AB01-treated plants using. UAE events was monitored over a 6 hour period in greenhouse-grown corn (hybrid Dekalb 68-05) and showed that hydraulic enhanced (AB01-treated) plants had a lower cumulative number of UAE events and a lower rate of UAE events, indicating less cavitation and more efficient fluid flow in the xylem (FIG. 8).

Field Trial of AB Compounds

Hydraulic enhanced plants showed higher harvest yields in field trials. The field performance of hydraulic enhanced plants in both environments that have abiotic stress (e.g., drought, heat stress) as well as unstressed, high yielding environments was tested.

Figure 9:
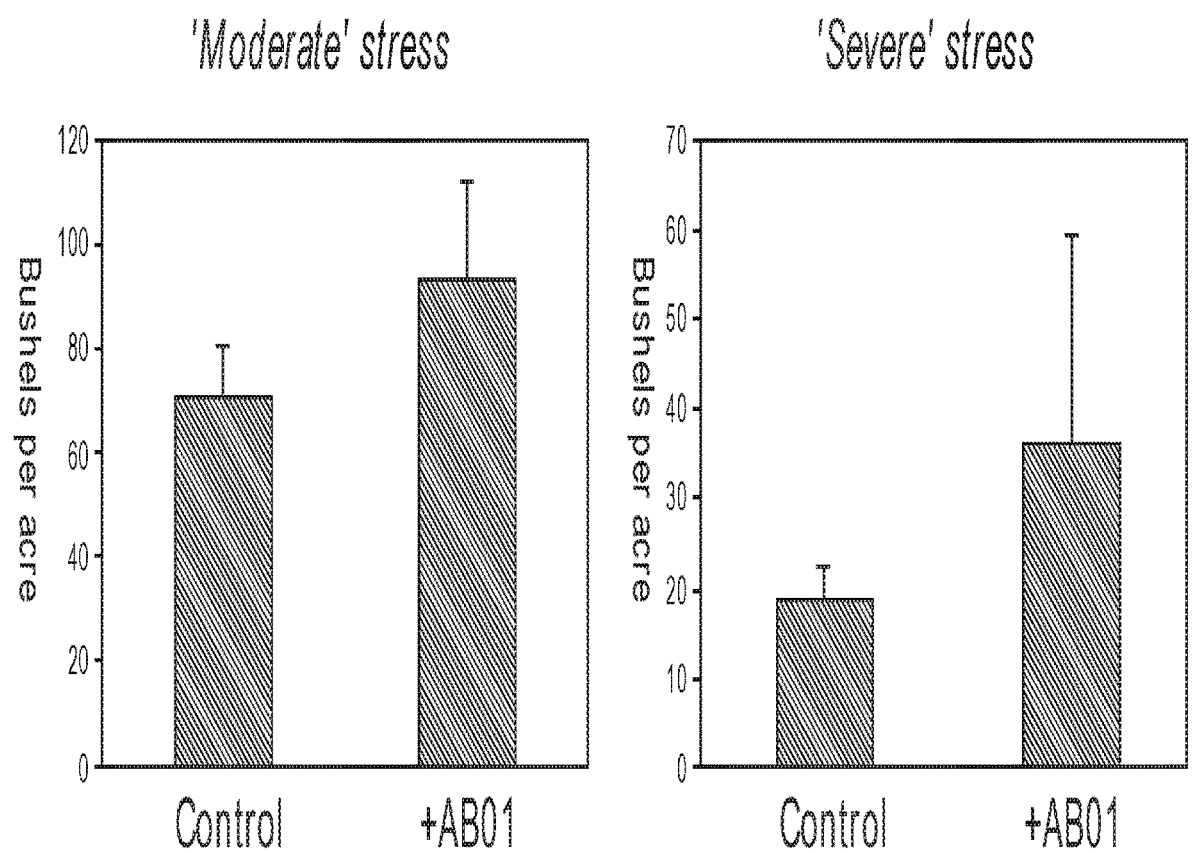

Two 'managed stress trials' were performed from June to November in Fresno County, Calif. Each trial consisted of three replicate plots each for treated and untreated states. Pioneer hybrid P2088AM was planted at a density of 33,000 plants per acre (30" rows). The field was irrigated with a subsurface drip tape (except during reproductive stages, as described below), and no precipitation was recorded during the trial period. AB01 treated plots were sprayed with a 2 g/ac dose at the tasseling (VT) stage. Two trials were performed, one imposing 'moderate' stress via reduction of irrigation, and another imposing 'severe' stress. In both trials, irrigation was provided to match measured evapotranspiration from emergence to the late vegetative stages. In the 'moderate stress' trial, irrigation was reduced by 50% at 10 days prior to tasseling (VT). Full irrigation was resumed 10 days after tasseling. The control plots averaged 70 bu/ac and AB01 treated plots averaged 93 bu/ac, a 21% increase (FIG. 9, left). In the 'severe stress' trial, irrigation was reduced by 90% at 10 days prior to tasseling (VT). Full irrigation was resumed 10 days after tasseling. The control plots averaged 19 bu/ac and AB01 treated plots averaged 37 bu/ac, a 91% increase in yield upon treatment (FIG. 9, right).

Figure 10:
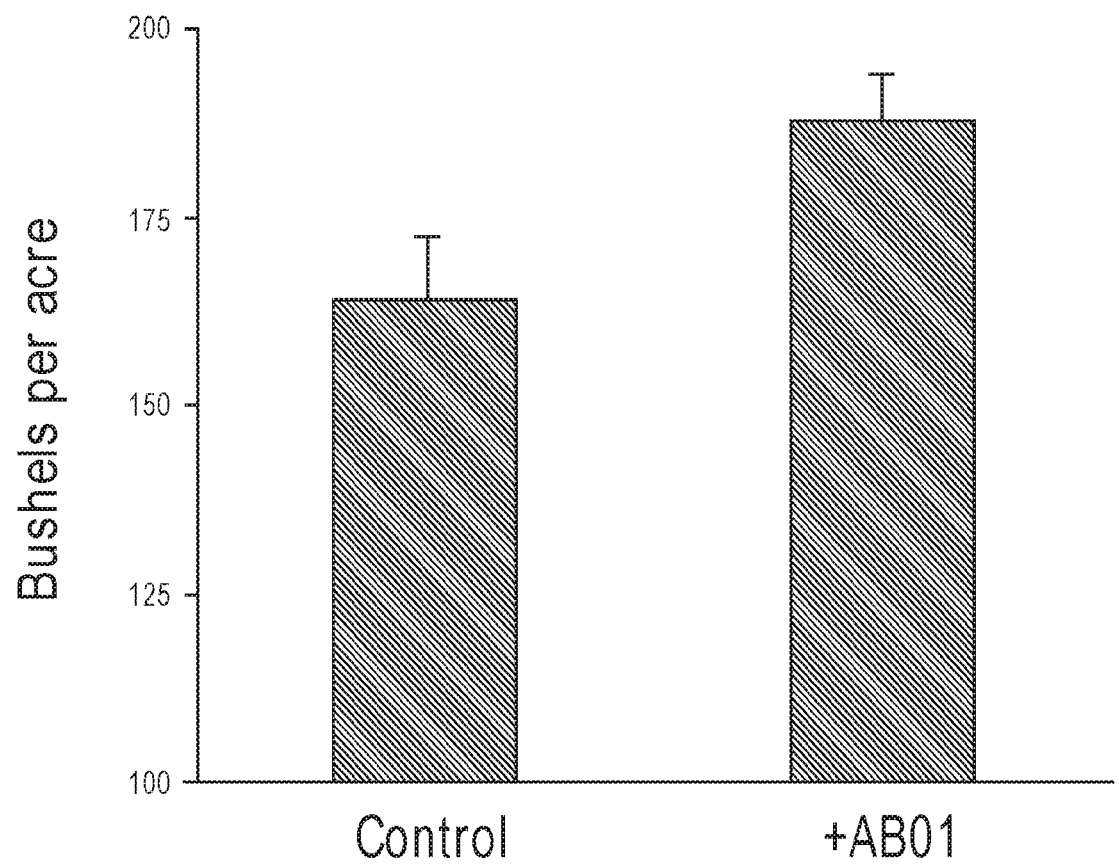

In another example of the performance of hydraulic enhanced plants in unstressed environments, an additional trial in Brondal, South Africa from December to April was performed. This trial consisted of 5 replicate plots each for control and treated conditions. In this trial, Pannar variety 6R-680 was planted at a density of 20,000 plants per acre and grown in dryland conditions. This site received excellent rainfall (29" measured) that was evenly distributed throughout the season. AB01 treated plots were sprayed with a 2 g/ac dose at the tasseling (VT) stage, as in the previous trials. Growing conditions and yields were considered excellent, with plants at no time displaying symptoms of stress. The control plots averaged 164 bu/ac and AB01 treated plots averaged 188 bu/ac, a 15% increase in yield upon treatment (FIG. 10).

Measurement of Hydraulic Enhancement of AB Compounds/Strigolactones

Figure 11:
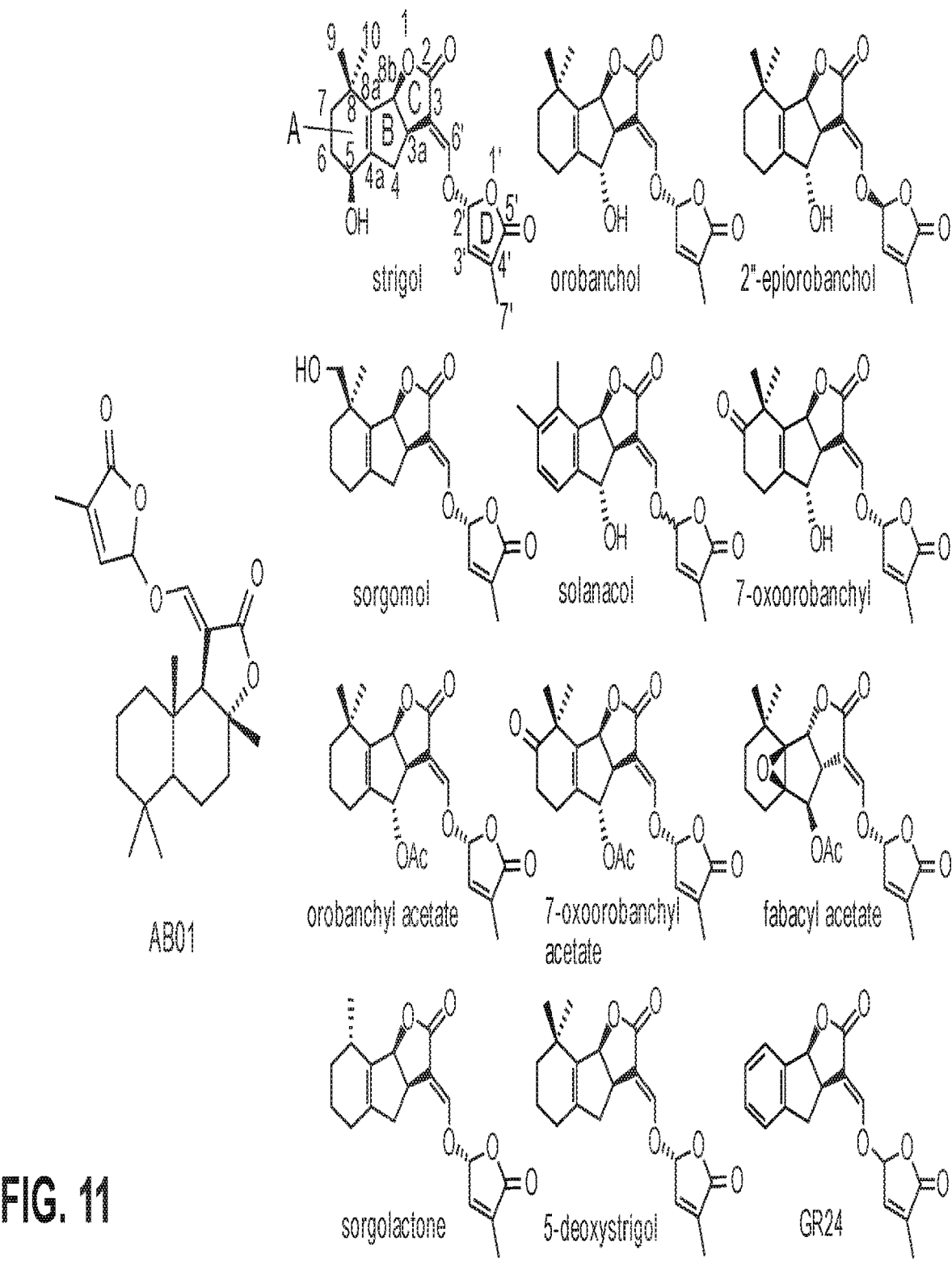
Figure 12:
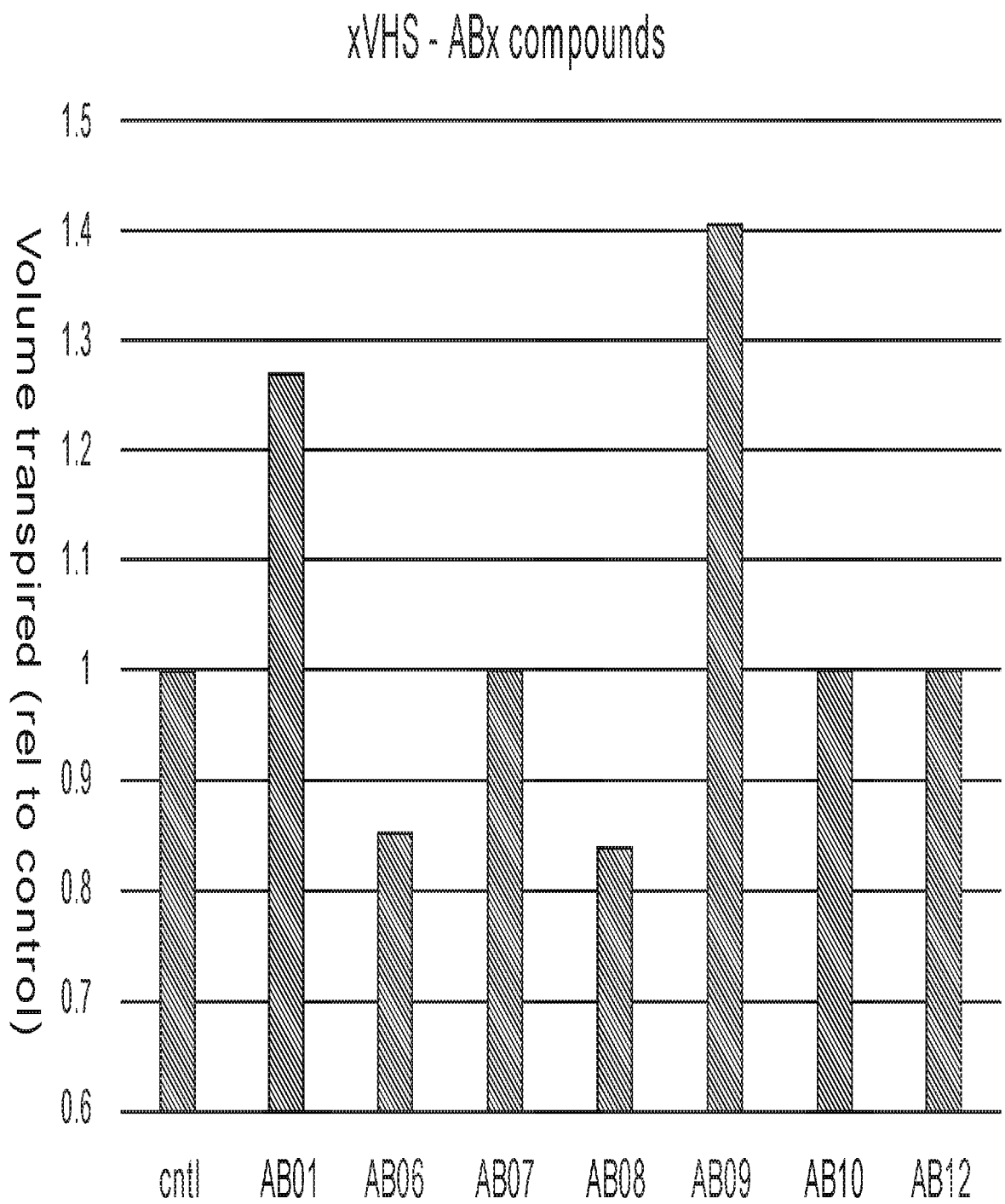

As described above, the addition of AB01 to corn resulted in hydraulic enhancement of the treated plants, with increased yield in field trials. A variety of strigolactones (FIG. 11) were synthesized and tested to determine their ability to induce hydraulic enhancement. AB01 and AB09 were found to be able to induce hydraulic enhancement (FIG. 12).

For example, the application of the compound AB09 (2-methyl-3-((4-methyl-5-oxo-2,5-dihydrofuran-2-yl)oxy)-4H-pyran-4-one) and its derivatives (FIG. 13) resulted in hydraulic enhancement of crop plants. Addition of 10Ong AB09 to the xVHS assay results in a 40% increase in transpiration, confirming the ability of AB09 to induce hydraulic enhancement (FIG. 12).

Inhibitors of Abscisic Acid Biosynthesis

Figure 14:
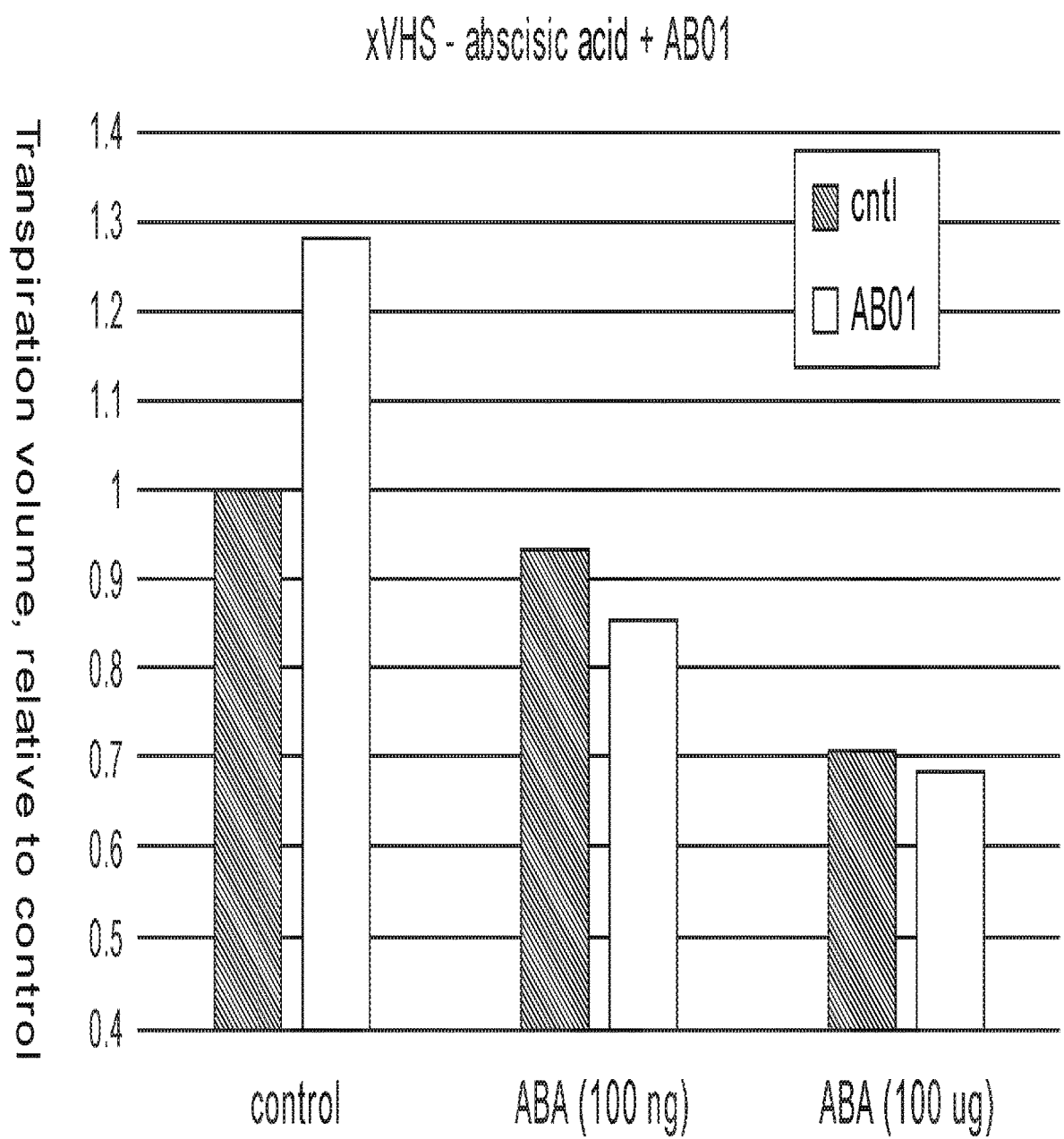
Figure 15:
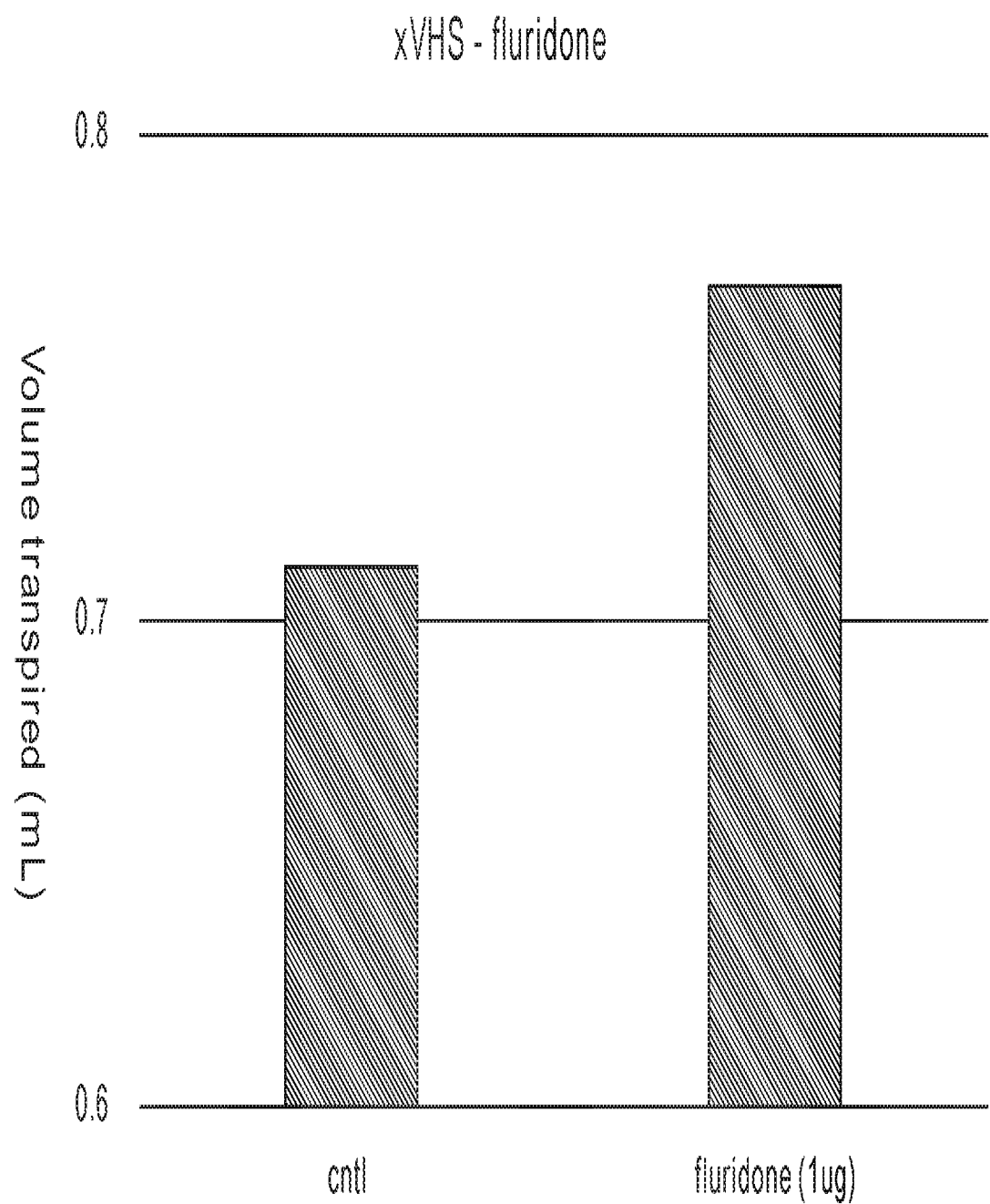

The addition of the plant growth regulator abscisic acid (ABA) was also shown to reduce the hydraulic enhancement in the xVHS assay (FIG. 14). Using this discovery, it could be reasoned that addition of inhibitors of ABA biosynthesis would result in increased hydraulic enhancement. In another experiment, fluridone was tested for its effect in hydraulic enhancement. Fluridone is an inhibitor of the phytoene desaturase, which is an upstream step in the synthesis of abscisic acid. And the addition of the herbicide fluridone was shown to increase hydraulic enhancement (FIG. 15).

Plant Growth Regulators

Figure 16:
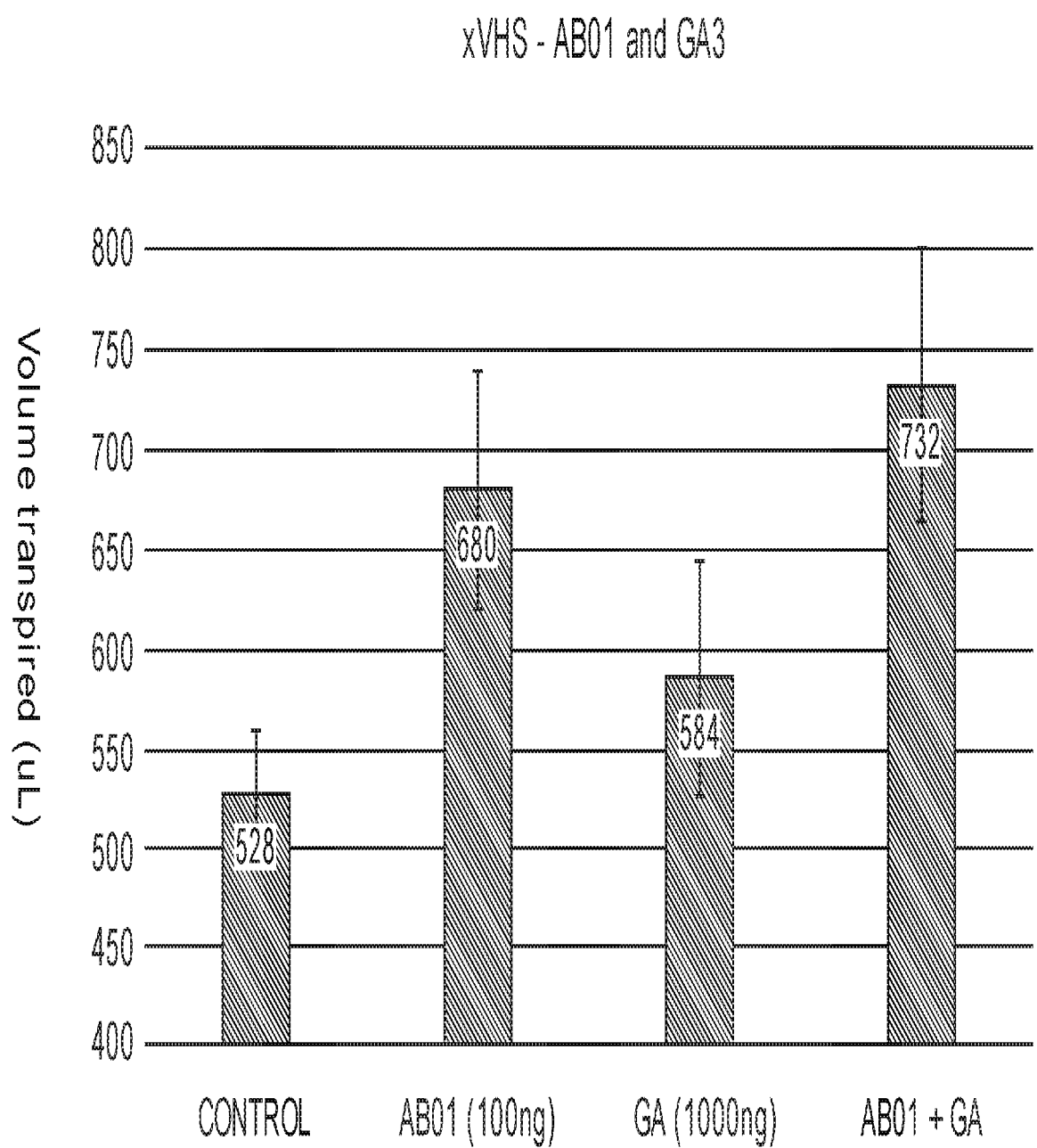
Figure 17:
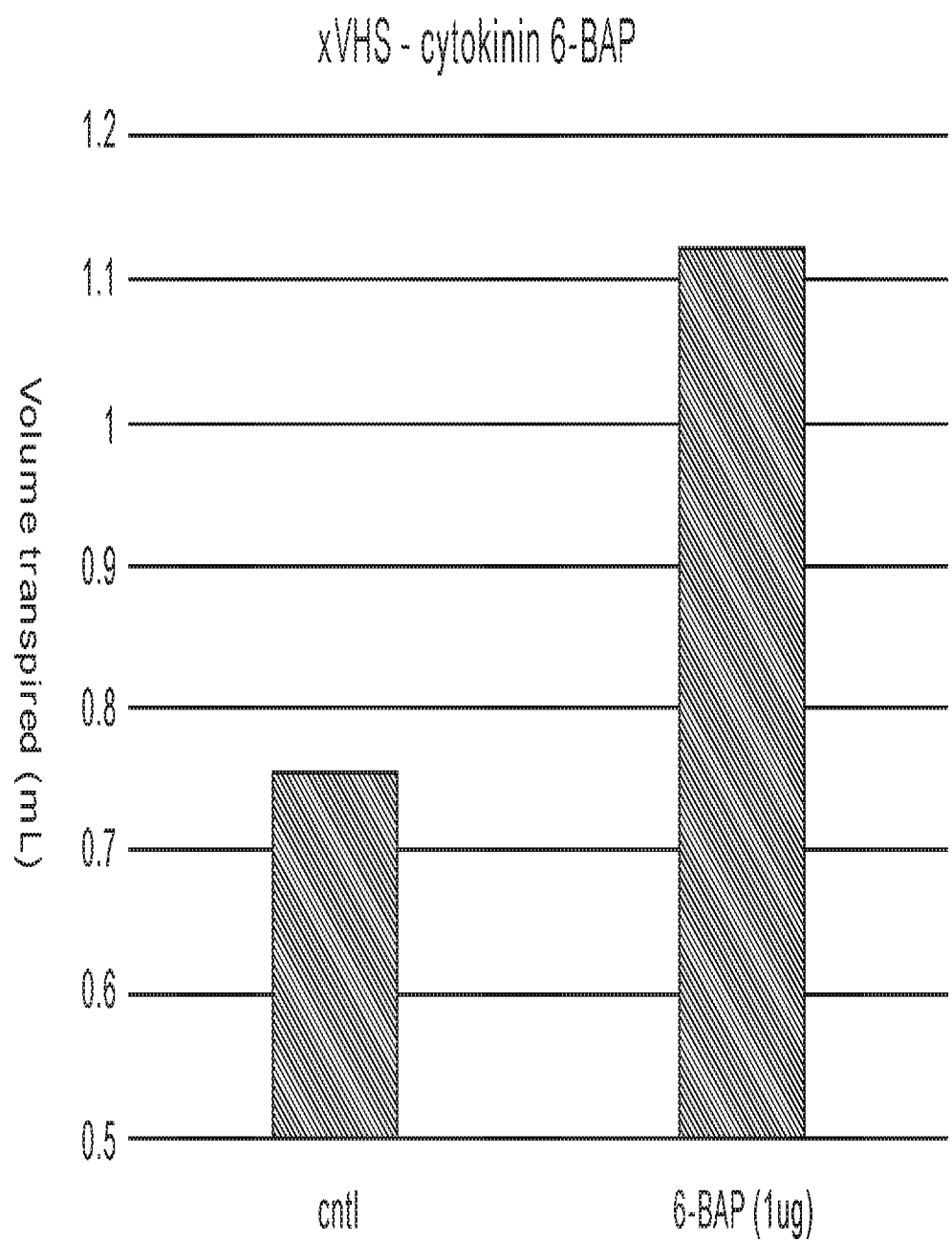

Specific combinations of plant growth regulators (PGRs) were used for hydraulic enhancement and increased harvest yield of crops. PGRs were tested to be co-applied with strigolactones and/or AB compounds (e.g., AB01). PGRs were also tested in the absence of strigolactones and/or AB compounds. It was found that PGRs elicit hydraulic enhancement in both experiments. PGRs were tested as a seed treatment, soil drench, granule formulation, or foliar spray. It was found that hydraulic enhancement was elicited by gibberellins, including GA1, GA3, GA4, GA7, GA0, ent-gibberellane, ent-kaurene, and their derivatives and chemical analogs (FIG. 16). It was also found that hydraulic enhancement can be achieved by the co-application of gibberellins (e.g., GA3) with AB compounds (e.g., AB01) (FIG. 16). In another experiment, the effect of hydraulic enhancement was also tested with cytokinins, including kinetin, zeatin, 6-benzylaminopurine (6-BAP), diphenylurea, thidiazuron, and their chemical derivatives and analogs. In this test, 1 µg 6-BAP was shown to elicit hydraulic enhancement of the tested plant (FIG. 17).

Synthesis of AB01

The synthesis of AB01 (MW: 374.47, C22H30O5) started from a readily available sesquiterpene, lactone, sclareolide. Sclareolide can be extracted from species of the *Salvia* plant and can be currently used in industrial production of perfumes. Sclareolide was condensed with a two-fold excess of methyl formate in the presence of lithium diisopropylamide. The isolated formyl lactone was then alkylated with chlorobutenolide to give a mixture of two diastereomers. A concise synthesis of chlorobutenolide is provided here. Resolution of stereomers was not necessary for downstream application.

Synthesis of formyl sclareolide: an oven-dried 100 mL 2-necked round bottom flask (2×14j) with stirbar, capped with a rubber septa and nitrogen bubbler was cooled under nitrogen flow. The flask was charged with sclareolide (1.50 g, 6.0 mmol, Sigma-Aldrich) and dissolved in dry THF (42 mL). The clear, colourless solution was cooled under inert gas to –0° C. using an ice water bath. LDA solution (3.60 mL, 7.20 mmol, 1.2 equivalents, 2.0M solution Sigma-Aldrich) was added dropwise via syringe to give a yellow-orange solution. Stirred at –78° C. for 30 minutes to ensure deprotonation. Methyl formate (0.74 mL, 12.00 mmol, 2.0 equivalents) was added neat via syringe. The pale yellow solution was left to stir overnight, warming to room temperature. The orange solution was quenched with distilled water (25 mL) and diluted with ethyl acetate (25 mL). The organic layer was separated and the aqueous layer extracted with ethyl acetate (3×25 mL). Combined organics were washed with 1N HCl (2×25 mL), brine (1×25 mL) and dried with $Na_2SO_4$. Filtration and concentration provided a golden oil (2.28 g). Purified by flash chromatography (silica gel, gradient 2-20% ethyl acetate:hexane) to provide a white solid (1.57 g) in 94% yield. Rf=0.18 in 10% ethyl acetate:hexane.

Synthesis of chlorobutenolide: A 1000 mL 3-necked (19j, 34j, 19j) round bottom flask was equipped with an oversized stirbar, nitrogen bubbler (19j), reducing adapter (19j to 34j) topped with a pressure equalizing dropping funnel capped with 19j rubber septa (34j) and rubber septa (19j). The assembled glassware was flushed under nitrogen and flame-dried under nitrogen purge. $CH_2Cl_2$ was charged to the flask (212 mL, anhydrous) and dropping funnel (106 mL). At room temperature, $TiCl_4$ (16.5 mL, 150 mmol) was added to the flask to give a clear, colourless solution. The titanium tetrachloride solution was cooled in an ice water bath and the dropping funnel charged with ethyl pyruvate (16.7 mL, 150 mmol) and vinyl acetate (13.8 mL, 150 mmol). The carbonyl solution in $CH_2Cl_2$ was added dropwise to the titanium tetrachloride solution over two hours, generating a bright yellow-orange suspension. When addition is complete, the suspension was further stirred for two hours at 0° C. (ice water bath). The clear orange-red solution was quenched with deionized water (140 mL) (caution: exothermic with vigourous gas production). $CH_2Cl_2$ separated and the aqueous layer extracted with $CH_2Cl_2$ (2×100 mL). Combined $CH_2Cl_2$ extracts were washed with deionized water (1×100 mL), brine (1×100 mL) and dried with $Na_2SO_4$. Filtered to give a clear golden yellow solution, concentrated to give a bright yellow oil (30.55 g, 85%). The yellow oil darkens on standing and decomposes releasing acrid fumes; these deformulation products complicate downstream purification. Can be stored cold in the refrigerator and can be used directly in the following step without purification.

A 1000 mL round bottom flask containing the crude aldol product (30.55 g, 128 mmol) was equipped with an oversized stirbar and taken up in absolute ethanol (345 mL) to give a yellow solution. To the stirred solution was added glacial acetic acid (17 mL) and concentrated HCl (17 mL). A reflux condenser was fitted to the flask and the solution heated to reflux for 4 hours. At this time, deionized water (430 mL) was added and the ethanol removed by fractional distillation until distillation rate slows and internal temperature rises to approximately 90° C. and volume of distillate is approximately 135% of initially added ethanol. The condenser was returned to reflux set up and the deep golden reaction mixture heated at reflux for 45 minutes. The cooled reaction mixture was extracted with ethyl acetate (3×150 mL). Combined extracts were washed with brine (1×100 mL) and dried $Na_2SO_4$. Filtered to give a golden solution, concentrated to give an orange oil (15.19 g). The crude orange oil was subjected to bulb-to-bulb distillation, collecting material at 120-135° C./8 mbar. The pale yellow oil (9.47 g, 65%) slowly solidified on standing.

A 25 mL 19j rbf was capped with a take-off head (2 necked, 2×19j), capped with a 19 j glass stopper and 19j reflux condenser. The flask was charged with $CH_2Cl_2$ (5 mL), $SOCl_2$ (1 mL, 14 mmol, 1.4 equiv) and a drop of DMF, then heated to reflux. A golden solution of hydroxybutenolide (1.15 g, 10 mmol) in $CH_2Cl_2$ (5 mL) was added dropwise to the refluxing vapours at such a rate to maintain reflux with immediate gas evolution. After two hours of reflux, the reaction mixture was cooled to rt, diluted with $CH_2Cl_2$ (20 mL) and poured into saturated $NaHCO_3$ (~50 mL) containing ice and rapidly stirred to destroy excess $SOCl_2$. When gas evolution has ceased the $CH_2Cl_2$ layer was separated and the aqueous extracted with $CH_2Cl_2$ (2×20 mL). Combined $CH_2Cl_2$ extracts were washed with brine (1×50 mL) and dried with freshly pulverized $MgSO_4$. The clear orange solution was filtered and concentrated to give a thin red liquid (1.106 g). The crude liquid was subjected to bulb-to-bulb distillation, collecting a clear colourless distillate (0.73 g, 53%) at 120-122° C./5 mbar.

Synthesis of AB01: a 100 mL round bottom flask containing the formyl sclareolide (1.57 g, 5.64 mmol) was flushed under nitrogen and dissolved in DMF (15 mL, anhydrous, Sigma-Aldrich) at room temperature. The clear yellow solution was treated with potassium carbonate (858 mg, 6.2 mmol, 1.1 equivalents) under nitrogen flow to give a yellow-white suspension. To the suspension was added dropwise via syringe a clear golden solution of chlorobutenolide (5.52 mmol, 1.2 equivalents) in DMF (5 mL, anhydrous). Addition of the chlorobutenolide solution caused a color change of the reaction mixture from yellow to orange to brown. Left to stir under nitrogen at room temperature for 24 hours. The dark suspension was diluted with distilled water (50 mL) and ethyl acetate (50 mL). Organic layer separated and the aqueous layer extracted with ethyl acetate (3×40 mL). The combined organics were washed with saturated $NaHCO_3$ (1×50 mL), distilled water (1×50 mL), brine (1×50 mL) and dried $K_2CO_3$. Filtration and concentration gave a viscous brown oil (2.63 g) that solidifies on standing. Purified by flash chromatography (silica gel, gradient 6-50% ethyl acetate:hexane) to provide a white solid (1.67 g) in 80% yield. Rf=0.18 in 25% ethyl acetate:hexane. The material tenaciously retained ethyl acetate and required prolonged drying under vacuum to remove trace solvate.

Synthesis of AB06

AB06 was synthesized from commercially available allyl alcohol and chlorobutenolide prepared by methods described above. The alkylation of allyl alcohol with chlorobutenolide was achieved using dichloromethane as solvate with pyridine as base. Purification was achieved by column chromatography and re-crystallization.

Synthesis of AB07

AB07 was synthesized from commercially available cinnamyl alcohol and chlorobutenolide prepared by methods described above. The alkylation of cinnamyl alcohol with chlorobutenolide was achieved using dichloromethane as solvate with pyridine as base. Purification was achieved by column chromatography and re-crystallization.

Synthesis of AB08

AB08 was synthesized from commercially available phenol and chlorobutenolide prepared by methods described above. The alkylation of phenol with chlorobutenolide was achieved using dichloromethane as solvate with pyridine as base. Purification was achieved by column chromatography and re-crystallization.

Synthesis of AB09

AB09 was synthesized from commercially available maltol and chlorobutenolide prepared by methods described above. The alkylation of maltol with chlorobutenolide was achieved under various conditions. The use of dichloromethane solvate with pyridine as base or the use of N,N'-dimethylformamide (DMF) with potassium carbonate as base was preferred. Purification was achieved by column chromatography and re-crystallization.

Synthesis of AB09 Derivatives

Figure 13:
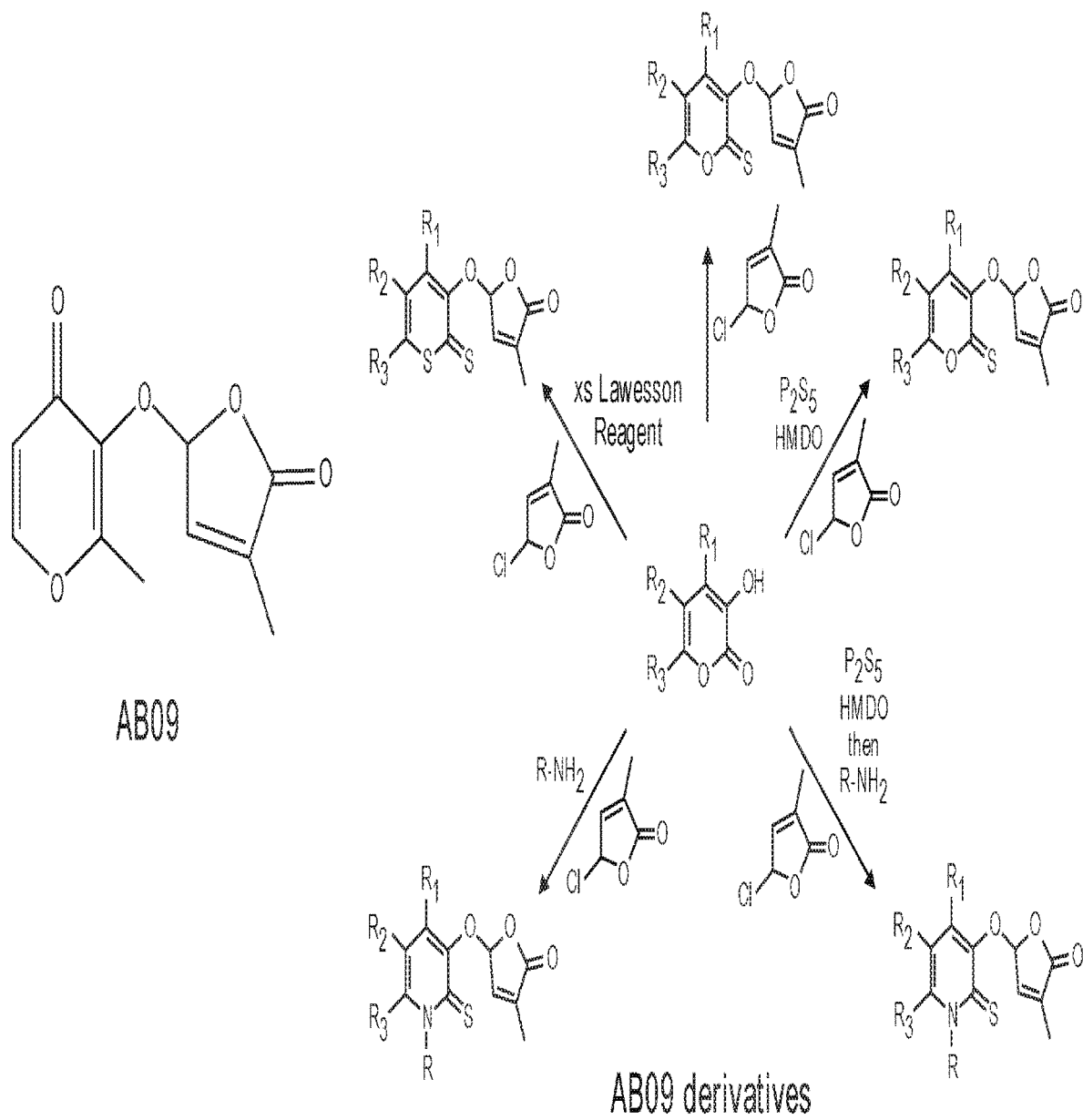

As shown in FIG. 13, derivatives of the AB09 family is provided using the methods described herein.

Using the parent compound of 3-hydroxy-4-pyrone ($R_1=R_2=R_3=H$) direct alkylation with chlorobutenolide under conditions described provides the class of 4-pyrone derivatives of the AB09 family.

Functional group interchange of the keto group of 3-hydroxy-4-pyrone to a 3-hydroxy-4-thiopyrone is achieved with the thionation reagent combination of phosphorus pentasulfide (P4S5) with hexamethyldisiloxane (HMDO). Alkylation with chlorobutenolide under conditions described provides the class of 4-thiopyrone derivatives of the AB09 family.

Reaction of the parent 3-hydroxy-4-pyrone with excess amine in a suitable solvate under acidic conditions leads to exchange of the ring oxygen of the pyrone with nitrogen providing access to 4-pyridones. Alkylation with chlorobutenolide under conditions described provides the class of 4-pyridone derivatives of the AB09 family.

Conversion of the keto to thioketo using P4S5/HMDO as described, followed by reaction with excess amine to facilitate ring oxygen to nitrogen exchange gives access to 3-hydroxy-4-thiopyridones. Alkylation with chlorobutenolide under conditions described provides the class of 4-thiopyridone derivatives of the AB09 family.

Exhaustive thionation of 4-pyrone using Lawesson's reagent exchanges both the keto and ring oxygen to sulfur providing access to 3-hydroxy-thiopyran-4-thiones. Alkylation with chlorobutenolide under conditions described provides the class of thiopyran-4-thione derivatives of the AB09 family.

One skilled in the art of organic synthesis can envisage the use of known 4-pyrone class of compounds as starting materials, such as but not limited to:
Kojic acid ($R_1=R_3=H$, $R_2=CH_2OH$)
Chlorokojic acid ($R_1=R_3=H$, $R_2=CH_2Cl$)
Comenic acid ($R_1=R_3=H$, $R_2=CO_2H$)
Meconic acid ($R_1=R_2=CO_2H$, $R_3=H$)
Pyromeconic acid ($R_1=R_2=R_3=H$)
Maltol ($R_1=CH_3$, $R_2=R_3=H$)
Allomaltol ($R_1=R_3=H$, $R_2=CH_3$)
Bromomaltol ($R_1=CH_3$, $R_2=H$, $R_3=Br$)
Ethylmaltol ($R_1=CH_2CH_3$, $R_2=R_3=H$)
mono- and di- and trialkylated 4-pyrones ($R_1=R_2=R_3=$alkyl or H)
mono- and di- and trihalogenated 4-pyrones ($R_1=R_2=R_3=$I, Br, Cl or F or H)

Using the parent compound of 3-hydroxy-2-pyrone ($R_1=R_2=R_3=H$) direct alkylation with chlorobutenolide under conditions described provides the class of 2-pyrone isomeric derivatives of the AB09 family.

Functional group interchange of the keto group of 3-hydroxy-2-pyrone to a 3-hydroxy-2-thiopyrone is achieved with the thionation reagent combination of phosphorus pentasulfide ($P_4S_5$) with hexamethyldisiloxane (HMDO). Alkylation with chlorobutenolide under conditions described provides the class of 2-thiopyrone isomeric derivatives of the AB09 family.

Reaction of the parent 3-hydroxy-2-pyrone with excess amine in a suitable solvate under acidic conditions leads to exchange of the ring oxygen of the pyrone with nitrogen providing access to 2-pyridones. Alkylation with chlorobutenolide under conditions described provides the class of 2-pyridone isomeric derivatives of the AB09 family.

Conversion of the keto to thioketo using $P_4S_5$/HMDO as described, followed by reaction with excess amine to facilitate ring oxygen to nitrogen exchange gives access to 3-hydroxy-2-thiopyridones. Alkylation with chlorobutenolide under conditions described provides the class of 2-thiopyridone isomeric derivatives of the AB09 family.

Exhaustive thionation of 2-pyrone using Lawesson's reagent exchanges both the keto and ring oxygen to sulfur providing access to 3-hydroxy-thiopyran-2-thiones. Alkylation with chlorobutenolide under conditions described provides the class of thiopyran-2-thione isomeric derivatives of the AB09 family.

One skilled in the art of organic synthesis can envisage the use of known 2-pyrone class of compounds as starting materials, such as but not limited to:
4-hydroxy-6-methyl-2-pyrone ($R_1=OH$, $R_2=H$, $R_3=CH_3$)
coumalic acid ($R_1=R_3=H$, $R_2=CO_2H$)
mono- and di- and trialkylated 2-pyrones ($R_1=R_2=R_3=$alkyl or H)

mono- and di- and trihalogenated 2-pyrones ($R_1=R_2=R_3=$I, Br, Cl or F or H)

Synthesis of AB10

AB10 was synthesized from commercially available sclareolide that was formylated with lithium diisopropylamide (LDA) and methyl formation at cryogenic temperatures. The resulting formyl sclareolide was then alkylated with bromophthalide in N,N'-dimethylformamide (DMF) solvate with potassium carbonate as base. Purification was achieved by column chromatography and re-crystallization.

Synthesis of AB12

AB12 was synthesized from commercially available para-toluenesulfonyl chloride and hydroxybutenolide prepared by methods described above. The sulfonylation of hydroxybutenolide with para-toluenesulfonlyl chloride was achieved using chloroform as solvate with pyridine as base. Purification was achieved by column chromatography and re-crystallization.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed. It is intended that the following claims define the scope of the disclosure and that methods and structures within the scope of these claims and their equivalents be covered thereby.

What is claimed is:

1. A method for treating a cultivated plant, comprising contacting the cultivated plant, a seed thereof, or a surrounding soil thereof with a compound of Formula (I):

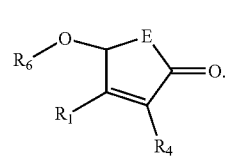

Formula (I)

or a salt thereof or a solvate thereof,
wherein:
each E is independently O, S, or —NR$_7$;
R$_1$, R$_4$, and each R$_7$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl;
R$_2$ and R$_3$ are each independently H, amino, halo, substituted or unsubstituted alkyl, substituted or unsubstituted aryl, substituted or unsubstituted heteroalkyl, substituted or unsubstituted arylalkyl, substituted or unsubstituted heteroaryl, substituted or unsubstituted heteroarylalkyl, substituted or unsubstituted cycloalkyl, or substituted or unsubstituted heterocycloalkyl; or R$_2$ and R$_3$ together form a bond, or form a substituted or unsubstituted aryl, and wherein R$_6$ has a structure of:

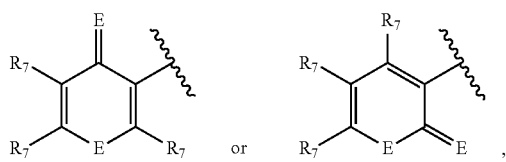

wherein

indicates a single bond.

2. The method of claim 1, wherein the compound has a structure of:

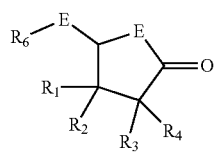

Formula (II)

or a salt thereof or a solvate thereof.

3. The method of claim 2, wherein R$_1$ and R$_4$ are each independently H or alkyl.

4. The method of claim 2, wherein E is O or —NR$_7$.

5. The method of claim 2, wherein the compound has a structure of:

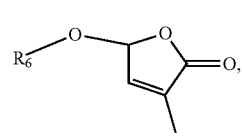

Formula (III)

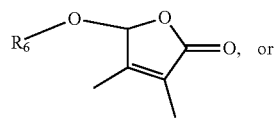

Formula (IV)

or

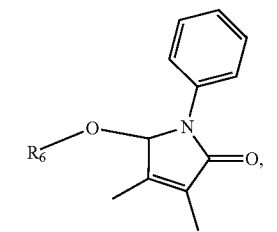

Formula (V)

or a salt thereof or a solvate thereof.

6. The method of claim 1, wherein R$_7$ is each independently H or alkyl.

7. The method of claim 6, wherein $R_6$ has a structure of:

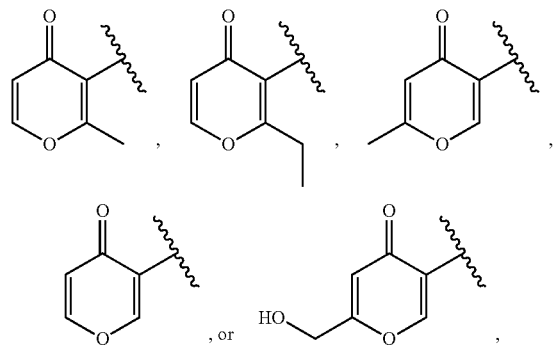

or a salt thereof or a solvate thereof.

8. The method of claim 7, wherein the compound has a structure of:

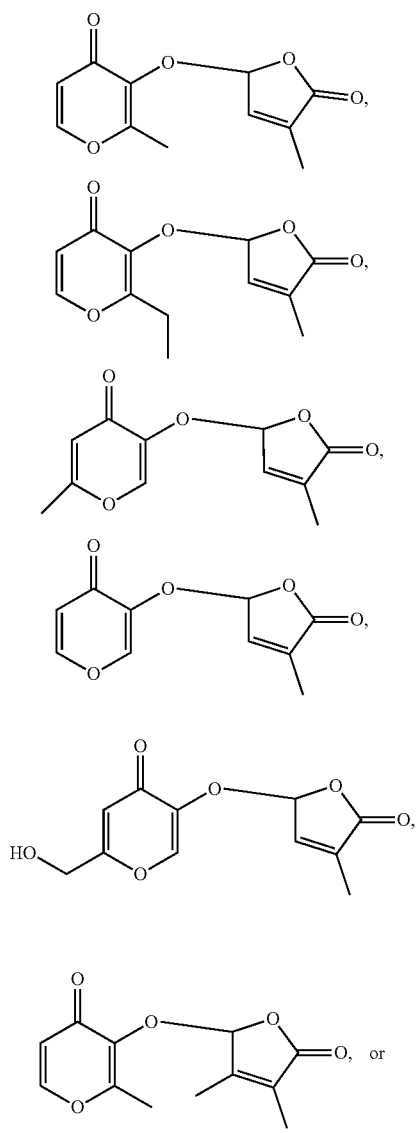

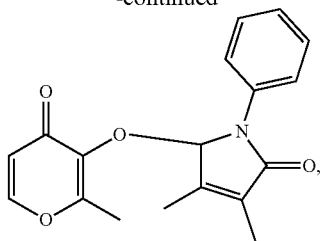

or a salt thereof or a solvate thereof.

9. The method of claim 1, wherein a yield of the cultivated plant is increased as compared to a substantially identical but otherwise an untreated cultivated plant.

10. The method of claim 9, wherein the yield of the cultivated plant is increased by at least about 10% as compared to the substantially identical but otherwise an untreated cultivated plant.

11. The method of claim 1, wherein the cultivated plant comprises a corn.

12. The method of claim 11, wherein the yield of the cultivated plant is measured by an average kernel mass (w/w), an average ear volume (v/v), an average relative hydration of silks (w/w), an average mass of silks (w/w), or any combination thereof.

13. The method of claim 1, wherein the contacting increases a transpiration of the cultivated plant as compared to a substantially identical but otherwise an untreated cultivated plant.

14. The method of claim 13, wherein the transpiration is measured as peak stomatal conductance.

15. The method of claim 14, wherein the transpiration of the cultivated plant is increased by at least about 10% as compared to the substantially identical but otherwise an untreated cultivated plant.

16. The method of claim 13, wherein the transpiration is measured as a canopy temperature.

17. The method of claim 16, wherein the canopy temperature of the cultivated plant is decreased by at least about 0.1° C. as compared to the substantially identical but otherwise an untreated cultivated plant.

18. The method of claim 13, wherein the transpiration is measured as a transpired water volume.

19. The method of claim 18, wherein the transpired water volume of the cultivated plant is increased by at least about 0.1 mL as compared to a substantially identical but otherwise an untreated cultivated plant.

20. The method of claim 1, wherein the contacting decreases a permanent wilting point of the cultivated plant as compared to a substantially identical but otherwise an untreated cultivated plant.

21. The method of claim 20, wherein the permanent wilting point of the cultivated plant is measured as volumetric water content of soil ($m^3/m^3$).

22. The method of claim 21, wherein the permanent wilting point is decreased by at least about 0.005 m³/m³ as compared to the substantially identical but otherwise an untreated cultivated plant.

23. The method of claim 1, wherein the cultivated plant is soybean, corn, rice, tomato, alfalfa, wheat, green algae or any combination thereof.

24. The method of claim 1, wherein the contacting comprises applying the compound, salt, or solvate as a spray.

25. The method of claim 1, wherein the contacting comprises applying the compound, salt, or solvate to a flower, leaf, or root of the cultivated plant.

26. The method of claim 1, wherein the contacting comprises applying an insecticide, a fungicide, or an herbicide with the compound, salt, or solvate.

27. The method of claim 1, wherein the compound has a structure of:

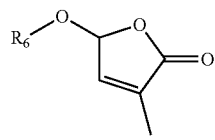

or a salt thereof or a solvate thereof.

28. The method of claim 1, wherein $R_6$ has a structure of:

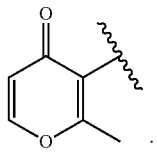 [SMILES: *c1c(C)occc1=O]

29. The method of claim 1, wherein $R_6$ has a structure of:

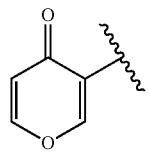

30. The method of claim 1, wherein the compound has a structure of:

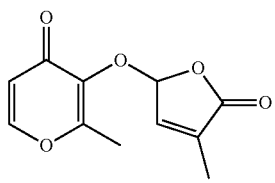 [SMILES: CC1=CC(Oc2c(C)occc2=O)OC1=O]

or a salt thereof or a solvate thereof.

31. The method of claim 1, wherein the compound of has a structure of:

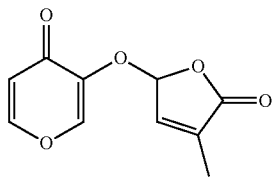

or a salt thereof or a solvate thereof.

* * * * *